US008389239B2

(12) United States Patent
Chen et al.

(10) Patent No.: US 8,389,239 B2
(45) Date of Patent: *Mar. 5, 2013

(54) ENHANCED EXPRESSION AND STABILITY REGIONS

(75) Inventors: Gang Chen, Yorktown Heights, NY (US); Robert Babb, Nanuet, NY (US); James P. Fandl, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 173 days.

This patent is subject to a terminal disclaimer.

(21) Appl. No.: 12/793,898

(22) Filed: Jun. 4, 2010

(65) Prior Publication Data

US 2010/0291626 A1 Nov. 18, 2010

Related U.S. Application Data

(63) Continuation of application No. 12/132,846, filed on Jun. 4, 2008, now Pat. No. 7,771,997.

(60) Provisional application No. 60/933,213, filed on Jun. 4, 2007.

(51) Int. Cl.
*C12P 21/02* (2006.01)

(52) U.S. Cl. ........ 435/69.1; 435/353; 435/354; 435/358; 435/366

(58) Field of Classification Search .......................... None
See application file for complete search history.

(56) References Cited

U.S. PATENT DOCUMENTS 6,689,606 B2 2/2004 Antoniou et al.

OTHER PUBLICATIONS

Mielke, C et al. (1996) Anatomy of Highly Expresssing Chromosomal Sites Targeted by Retroviral Vectors. Biochemistry 35:2239-2252.
Koduri, R.K. et al. (2001) An efficient homologous recombination vector pTV(I) contains a hot spot for increased recombinant protein expression in Chinese hamster ovary cells. Gene 280:87-95.
Kito, M. et al. (2002) Construction of engineered CHO strains for high-level production of recombinant proteins. Appl. Micorbiol. Biotechnol. 60:442-448.
Fukushige, S. and B. Sauer. (1992) Genomic targeting with a positive-selection lox integration vector allows highly reproducible gene expression in mammalian cells. PNAS 89:7905-7909.
Kwaks, T.H.J. and A.P. Otte. (2006) Employing epigenetics to augment the expression of therapeutic proteins in mammalian cells. Trends in Biotechnology 2 24(3):137-142.
Aldrich, T.L., Viaje, A., Morris, A.E. 2003. EASE Vectors for Rapid Stable Expression of Recombinant Antibodies. Biotechnol. Prog. 19:1433-1438.

*Primary Examiner* — Jim Ketter
(74) *Attorney, Agent, or Firm* — Joseph Zahner; Tor Smeland; Valeta Gregg

(57) ABSTRACT

Expression-enhancing nucleotide sequences for expression in eukaryotic systems are provided that allow for enhanced and stable expression of recombinant proteins in eukaryotic cells. Enhanced expression and stability regions (EESYRs) are provided for expression of a gene of interest in a eukaryotic cell. Chromosomal loci, sequences, and vectors are provided for enhanced and stable expression of genes in eukaryotic cells.

20 Claims, 13 Drawing Sheets

Fig. 3A

```
EESYR          5032 TT-------------CCTGAGTTCCGCCAA-CGCCTAGTGACATCCTGTG---------- 5067  SEQ ID NO:13
Rat Ch3 trim   5008 TTTATC-----TTTCCCTGGGGACAGCCAA-AGCCTGGTGGCATCCTCTGTGAAGTGTTC 5061  SEQ ID NO:14
M Mus Ch2 trim 6021 TTTATC-----TTTCCCTGGGGACCGCCAA-AGCCTGGTGGCATACTGTACATTCTG--- 6071  SEQ ID NO:15
H. Sap. Ch20 tr 5972 AGAAACACAACTTCTCCCAGGGAGAGTCAAGAGAGCAGTGTCATTTCCTATAAAATGTCC 6031  SEQ ID NO:16
                    **   *     * ***  *     *** ***       *

EESYR          5068 --------CACACCCT------AAGGTGGCCTTTGTGTGGC------ACTGGCTTGGGTG 5107  SEQ ID NO:13
Rat Ch3 trim   5062 ATTCAAGACAGGCTCTGTCTTAAAGGTGGCCTTCGCATGGCGCTGGCACTGGCCGGGGCA 5121  SEQ ID NO:14
M Mus Ch2 trim 6072 --------TACACTGTTCATTCAAAACAGGCTCTGTCTTAAA-----GATGGTCTGAGCG 6118  SEQ ID NO:15
H. Sap. Ch20 tr 6032 A--AGGCCAATCCCAGGTCCCGGTGTCAGCCCTTGCGTGTGGC----ACTGGCACCAGCA 6085  SEQ ID NO:16
                         *          *       *   *       ***    *

EESYR          5108 GTCGGGAAAGG-CATTTTCAGCTTGTT-GCAGAACTGCCACAGTAGCATGCTGGGT-CCG 5164  SEQ ID NO:13
Rat Ch3 trim   5122 GTCAGGAGAGGGTATTTTTAGCTTCTTTGCAGAATGGCCTCAGGAGCGTGCTGAGT-CTG 5180  SEQ ID NO:14
M Mus Ch2 trim 6119 GTCAGAAAAGGGTATTGTTAACTTGTTTGCAAAACTGCCTCAGGAGAGTGCTGAGT-GCS 6177  SEQ ID NO:15
H. Sap. Ch20 tr 6086 GCCAGAAAGGT-TACTTGTGACTTGTTTTCAGTGCTTTCCTGGGAGTGTCCTGAAAGCTG 6144  SEQ ID NO:16
                    *   *  *     *     *  ** ** **     *  **  *   *    *

EESYR          5165 TGAAAGTTTCTGCCCGTTAACAAGAAGTCTCTACTACTTGTGACCTCACCA-----GTGA 5219  SEQ ID NO:13
Rat Ch3 trim   5181 TGAAAGTTGCTGCCAGTTAAGGAGAAGTCTCTACCACTCGTGACCTCACCA-----TTGA 5235  SEQ ID NO:14
M Mus Ch2 trim 6178 TGAAAGTTGCTGCCCGTTAAGGAGAAGTCTCTACTACTTGTGATCTCACCA-----TCGA 6232  SEQ ID NO:15
H. Sap. Ch20 tr 6145 GCAGTGTTTCTGCCTCGTCAGAAGAGGCCTCATTCATTTGGGGTTGTACCAGCAACTTAA 6204  SEQ ID NO:16
                     *  *** *****  **   *  *** ****   *   ****        *

EESYR          5220 AAATTTCTTTAATTG------TCTCCTGGTGTTC-TGGGTTTTG--------CATTTTGT 5265  SEQ ID NO:13
Rat Ch3 trim   5236 AAATTTCTTTAATTG------TCTCCTCGTGTTC-TGGGCTTTG--------CAGTTTTGT 5281  SEQ ID NO:14
M Mus Ch2 trim 6233 AAATTTCTTTAATTG------TCTCCTGGTGTTC-TGGGTTTTG--------CAGTTTTGT 6278  SEQ ID NO:15
H. Sap. Ch20 tr 6205 AAAGTTTTTTTTTTT--CTTCCCTTCCAGTGTTAATAGATTTTGAAAGAGGCATTTTTGT 6264  SEQ ID NO:16
                    ***  **  ***  **           ***  * ***** ** *  ***   **  *****

EESYR          5266 TTCTAAGGATACATTCCTGGGTGATGTCATGAAGTCCCCAAAGACACAGTG-GGGCTGTG 5324  SEQ ID NO:13
Rat Ch3 trim   5282 TCCTAAGGATACATTCTTGGGTGATGTCACGAAGTCCCCAAAGACACAGTG-GGGCTGTG 5340  SEQ ID NO:14
M Mus Ch2 trim 6279 TTCTAAGGATACATTCTTGGGTGATGTCACAAAGTCCCCAAAGACACGGTG-GGGCTGTG 6337  SEQ ID NO:15
H. Sap. Ch20 tr 6265 TTCTAATTACAAATTCCTGGGTGATGTCATTAAGCCCTCAAACACCCGGTCGAGGCGGCA 6324  SEQ ID NO:16
                    * **** *  *  *** ************  *** ** **** ** *** ** ***  *

EESYR          5325 TTGGATTGGGAAAGAT-------------GATTTATCTGG-GGTGTCAAAAGGAAAAGAAG 5371  SEQ ID NO:13
Rat Ch3 trim   5341 TTAGATCGGGACAGACAATATTGCTGAGGATTTATCTGAAGGTGTCAAAAGGAGAAGAAG 5400  SEQ ID NO:14
M Mus Ch2 trim 6338 TTAGATGGGGAAAGACAGT-CTGCTGAGGATTTATCTGGAACTGTCAGAAGGAAAAGAAG 6396  SEQ ID NO:15
H. Sap. Ch20 tr 6325 CTGAATGGGGAAAGACAATA-TGCTAACAAGTTATCTGAGGGTGTCAGAAAGAAATGATG 6383  SEQ ID NO:16
                      * ** **** ***        * ******   *****  **  ** *  *

EESYR          5372 GGAAACAGG-CACTTGGGA-AAATGTCCTCCCGCCCACCCGAATTTTGGCTT-GGCAACC 5428  SEQ ID NO:13
Rat Ch3 trim   5401 GGAAACAGGGCACTCAGGG-AAATGGCCTCTAGTCT----GAGTTCTGGCTC-AGCAACA 5454  SEQ ID NO:14
M Mus Ch2 trim 6397 GTAAATGGGGCACTTGGGA-AAGTGCCTCTAGTTT----GACTTCTGGCTT-AGCAAAG 6450  SEQ ID NO:15
H. Sap. Ch20 tr 6384 AAAAACAGTACAGTTGGGGGAAATGTTTTCCAGCCT----GCTTTCTGGTTTTTAGCGACT 6439  SEQ ID NO:16
                    ***  *  ** **  **  ** **   **  *

EESYR          5429 GT-GGTGGAGGAGCAAGAAACACGTGGACGTTTGA-GGAGGCAT-GGGGTCCTAGGAGGA 5485  SEQ ID NO:13
Rat Ch3 trim   5455 GA-GGTGGGAGATAAGGCACACAGTGGTTAGAAGGAGTCATCAGGGGTTCTGGGAGGA 5513  SEQ ID NO:14
M Mus Ch2 trim 6451 GT-TGTGGGGAGATAAGGCATACACAGTAGTTAGCAGGAGGCAACAGGGTCCTGGGAGGA 6509  SEQ ID NO:15
H. Sap. Ch20 tr 6440 GCATGGGAAGAGATAAGACACACATGGCTTTTATAAGGAGCCATCGGGATCTCTAGGGCA 6499  SEQ ID NO:16
                     *  *   *      *** * **    *  **   ****   ** *      * ***

EESYR          5486 CAGGAAGCAGAAGGAGAGAGCTGGGCTGACAGCCTGCAGGCATTGCACAGTTTC---AGAA 5543  SEQ ID NO:13
Rat Ch3 trim   5514 CAGGAGGCAGGAG-----AGGCAGGGCTGACAGTGTGCAATCATTGTGTAGTCTC--CCAA 5567  SEQ ID NO:14
M Mus Ch2 trim 6510 CCGCGAGGCAGAAGGAG-AGGCTGGGCTGACAGCATGCAATCATTGCATAGTCTC--CAAA 6566  SEQ ID NO:15
H. Sap. Ch20 tr 6500 CATGAGGCAGGAGAAAAGAATTGGGCTGAAAGCATCCAATCATCACATATTCACGGAGAA 6559  SEQ ID NO:16
                    *  ** **** **       *******   * *  **   ** * * ***

EESYR          5544 GGAGATTACAGCATGACTGAG-------TTTTTAGGGATCCAACAGGGACCTG---GGTAG 5594  SEQ ID NO:13
Rat Ch3 trim   5568 GGAGATTACAACATGGCTGAA------TTTTCAGGGGTCCAACGGAGACTGT---AGTGG 5618  SEQ ID NO:14
M Mus Ch2 trim 6567 GGAGATTGCAACATGGCTGAG------TTTTTCAGAGGTCCTACAGAGCCCGT---GGTAG 6617  SEQ ID NO:15
H. Sap. Ch20 tr 6560 AGAGATTACAATATAGCAGAGGAAAGCTCTTCAGGGCTCCTACAGGGACCTTTGGGACAA 6619  SEQ ID NO:16
                    ******  **  **  *  **        **   **   ** *  ** **     *

EESYR          5595 AGATTCTGTGGGCTCTGAGGCAACTTGACCTCAGCCAGATGGTATTTGAATAACCTGCTC 5654  SEQ ID NO:13
Rat Ch3 trim   5619 AGATTCTGTGGGTTCTGAGCAACTTGACTTCAGCCAGATGGCATTTGAATAAC------ 5672  SEQ ID NO:14
M Mus Ch2 trim 6618 AGATTCTGTGGGTTCTGAGCAACTTGACTTTAGCCAGATGGTATTTGAGTAATCTGGG- 6676  SEQ ID NO:15
H. Sap. Ch20 tr 6620 AGATTCAGTGGGCTTTGGACAGCCTTGACTTCAACTAGATGGTATTTGAATAATCTGCT- 6678  SEQ ID NO:16
                    ****** ****** * ** *  ** * * *   ******** ******** ***
```

Fig. 3B

```
EESYR           5655 TTAGAGGGAAAACAGACATAGCAAACAGAGCCACGTTTAGTGATGAAACTCTCACTTTGC 5714  SEQ ID NO:17
Rat Ch3 trim    5673 -------------AGCTCCAGCAAGCACAGCCACATTTAGGGATGAAACTCTCACTTTGA 5719  SEQ ID NO:18
M Mus Ch2 trim  6677 --AGAGAGAAAACAGCTACAGCAAACAGGGCCACATTTAGTGACGAAACTCTCACTTTGA 6734  SEQ ID NO:19
H. Sap. Ch20 tr 6679 --GGAGAGAAAACAGATATAGCACACACTGTCACATTTAGCGTTGAAACTCTCGGTTTGA 6736  SEQ ID NO:20
                           **   ****  **  * ***  ***** *  *********  ****

EESYR           5715 CTG---AGTCATGTGCGGCCATGCCCAGGGGTCAGGCTGACACTCAACTCAAAAACAAGT 5771  SEQ ID NO:17
Rat Ch3 trim    5720 CTGT-GAGTCACGTGTAGCTGTGTCCCGAGGTCAGGCTGGCCCTCAGCTCAAAAACAAGT 5778  SEQ ID NO:18
M Mus Ch2 trim  6735 CTGTTGAGTCATTTGCAG-TGGGCCCTGAGGTCAGGCTGGCCCTCAGCTCAAAAACAAGC 6793  SEQ ID NO:19
H. Sap. Ch20 tr 6737 CTAT-GAGTAATGTTCAGCCATGCCCAAGGGTCAGGCCTACACTCA-CTCAGAAACAAGT 6794  SEQ ID NO:20
                      **    ***  *    *      *   ** ********   ****  ****  *******

EESYR           5772 GAGAAATTGAAG-----------ACAATCCGTGGTGGCAGCTACTGGAA-GGGCCACCAC 5819  SEQ ID NO:17
Rat Ch3 trim    5779 GAGGGATTGAAGCAATTACTCAGATAATTCACAGCCACAGCTACGGGGA-GGGCCGC--- 5834  SEQ ID NO:18
M Mus Ch2 trim  6794 GAGGAACTGAAGCAATTACTCAGATAATCCACAGCCACAGCCACTGGAAAGGGCCAC--- 6850  SEQ ID NO:19
H. Sap. Ch20 tr 6795 GGGGAATTGAAGCAATTATTCAGATAATCCATAGACATAGCTACTGGCCAGTGCTGC--- 6851  SEQ ID NO:20
                     *  *  * *****           * ***  *     *** ** **   * **  *

EESYR           5820 ATCCCCAGAAAGAGT------GGAGCTGCTAAAAAGCCAT---------TTGTGATAGGCA 5865  SEQ ID NO:17
Rat Ch3 trim    5835 ATCCCCAGAAACATC------GGGGTTACTATAAAGCTA-----------GTGGTGGTCA 5877  SEQ ID NO:18
M Mus Ch2 trim  6851 ATCCCCAGAGACAGCACAGCAGGGGTGGGGTGGGCTATGAGAAAGTTAGTGATTGTAG    6910  SEQ ID NO:19
H. Sap. Ch20 tr 6852 -ACCCCTGATTTAGCCCA---GAAACAGTAATGCTATTATAAGCT-GTTGGTGATTTGTG 6906  SEQ ID NO:20
                      **** **  *                *        *             * **   *

EESYR           5866 CAGTTATCTTGAATGCATGGAGCAGAG---ATTACGGAAAAATCGAGAATGTTAATGAGG 5922  SEQ ID NO:17
Rat Ch3 trim    5878 CAGTTATCTTGAATGTATGGAGCAGAGGAGATTACAGAAAAACCTAGAATGTTAATGAGG 5937  SEQ ID NO:18
M Mus Ch2 trim  6911 CAGTTATCTAGAATGTGCGGAGCAGAGGAGGTTACACAAAAACCTAGAATG--------- 6961  SEQ ID NO:19
H. Sap. Ch20 tr 6907 GAGCAATCTTGAATTTATTAAGGAAAGGAGATTATAGAAAAATCCAGAATGCCAATG-GG 6965  SEQ ID NO:20
                     **  **** ****   ** **   ***  *****  ******
```

ENHANCED EXPRESSION AND STABILITY REGIONS

CROSS-REFERENCE TO RELATED APPLICATIONS

This application is a continuation of U.S. non-provisional application Ser. No. 12/132,846, now U.S. Pat. No. 7,771,997, filed 4 Jun. 2008, which claims benefit under 35 USC 119(e) of U.S. Provisional application No. 60/933,213, filed 4 Jun. 2007, which application is herein specifically incorporated by reference in its entirety.

BACKGROUND

1. Field of the Invention

The invention provides for expressing recombinant proteins in eukaryotic cells. In particular, the invention includes methods and compositions for improved expression of proteins in eukaryotic cells by employing expression-enhancing nucleotide sequences. The invention includes enhanced expression and stability region (EESYR) sequences that facilitate enhanced and stable expression of recombinant proteins in eukaryotic cells, and methods of using such sequences.

2. Description of Related Art

The development of expression systems is an important goal for providing a reliable and efficient source of a given protein for research and therapeutic use. Recombinant protein expression in mammalian cells is often preferred for manufacturing therapeutic proteins due to, for example, the ability of mammalian expression systems to appropriately post-translationally modify recombinant proteins.

Several vectors are available for expression in mammalian hosts, each containing various combinations of cis- and, in some cases, trans-regulatory elements to achieve high levels of recombinant protein with short incubation times. Despite the availability of numerous such vectors, the expression of a recombinant protein achieved in mammalian systems is often unacceptably low or otherwise unsatisfactory. Moreover, developing a cell line that reliably expresses sufficiently high levels of a desired protein often requires time consuming cloning and amplification steps. Accordingly, there is a need in the art for improved mammalian expression systems.

BRIEF SUMMARY

In one aspect, an isolated nucleotide sequence comprising an expression-enhancing sequence selected from a sequence of SEQ ID NO:1-6, or an expression-enhancing fragment thereof, is provided.

In one embodiment, the expression-enhancing sequence comprises an expression-enhancing sequence of SEQ ID NO:5 located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In another embodiment, an expression-enhancing sequence is provided that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5.

In another embodiment, the recombination recognition site is positioned as described above, providing that the expression-enhancing sequence comprises a sequence that is at least 90% identical, more preferably at least 95% identical, most preferably at least 99% identical, to the expression-enhancing sequence of SEQ ID NO:5 or an expression-enhancing fragment thereof.

In one embodiment, the expression-enhancing sequence further comprises at least one recombinase recognition site comprising a sequence independently selected from a loxp site, a lox 511 site, a lox 2272 site, and a frt site. In one embodiment, the recombinase recognition site is within the expression-enhancing sequence. In another embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence. In a specific embodiment, two recombinase recognition sites of opposite orientation are present within the expression-enhancing sequence. In another embodiment, three recombinase recognition sites are present within the expression-enhancing sequence.

In one aspect, an isolated nucleotide sequence is provided that comprises an expression-enhancing sequence that is at least 80% identical, preferably at least 90% identical, more preferably at least 95% identical, most preferably at least 99% identical to an expression-enhancing sequence of SEQ ID NO:1-6 or an expression-enhancing fragment thereof. In one embodiment, the expression-enhancing sequence displays the recited identity to a sequence of SEQ ID NO:5 as described above.

In one aspect, an isolated eukaryotic cell is provided that comprises an expression-enhancing sequence selected from SEQ ID NO:1-6 or an expression-enhancing fragment thereof. In one embodiment, the expression-enhancing sequence comprises an expression enhancing sequence of SEQ ID NO:5 as described above.

In one embodiment, the eukaryotic cell is a mouse, rat, hamster, or human cell. In a specific embodiment, the eukaryotic cell is a CHO cell.

In one embodiment, the eukaryotic cell further comprises at least one recombinase recognition sequence within the expression-enhancing sequence. In a specific embodiment, the at least one recombinase recognition sequence is independently selected from a loxp site, a lox 511 site, a lox 2272 site, and a frt site. In one embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence. In a specific embodiment, two recombinase recognition sites are of opposite orientation and are present within the expression-enhancing sequence. In another embodiment, three recombinase recognition sequences are present, and one of the three recombinase recognition sequences is in an orientation opposite to the two remaining recombinase recognition sequences.

In one embodiment, the recombinase recognition site in the expression-enhancing sequence of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In another embodiment, the recombinase recognition site in in a sequence that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5. In a specific embodiment, the recombinase recognition site is located within nucleotides 6400-6500 of SEQ ID NO:5. In another specific embodiment, the recombinase recognition site is inserted before, after, or within the "act" triplet of nucleotides 6471 to 6473 of SEQ ID NO:5 in an expression-enhancing sequence of SEQ ID NO:5.

In another specific embodiment, the recombination recognition site is positioned as described above, with the caveat that the expression-enhancing sequence comprises a sequence that is at least 90% identical, more preferably at least 95% identical, most preferably at least 99% identical, to nucleotides 5218 through 6048 of SEQ ID NO:5 or an expression-enhancing fragment thereof.

In a specific embodiment, the cell is a CHO cell and the recombinase recognition site is inserted in the CHO cell genome at or within the "act" triplet of nucleotides 6,471 to 6,473 of SEQ ID NO:5.

In one embodiment, a first GOI is inserted within the expression-enhancing sequence of SEQ ID NO:5 as described above, and the first GOI is optionally operably linked to a promoter, wherein the promoter-linked GOI (or the GOI) is flanked 5' by a first recombinase recognition site and 3' by a second recombinase recognition site. In another embodiment, a second GOI is inserted 3' of the second recombinase recognition site, and the second GOI is flanked 3' by a third recombinase recognition site.

In a specific embodiment, the GOI is operably linked to a promoter capable of driving expression of the GOI, wherein the promoter comprises a eukaryotic promoter that is regulatable by an activator or inhibitor. In another specific embodiment, the eukaryotic promoter is operably linked to a prokaryotic operator, and the eukaryotic cell optionally further comprises a prokaryotic repressor protein.

In another embodiment, one or more selectable markers are included between the first and the second and/or the second and the third recombinase recognition sites. In a specific embodiment, the first and/or the second genes of interest and/or the one or more selectable markers are operably linked to a promoter, wherein the promoter may be the same or different. In a specific embodiment, the promoter comprises a eukaryotic promoter (such as, for example, a CMV promoter), optionally controlled by a prokaryotic operator (such as, for example, a tet operator). In a specific embodiment, the cell further comprises a gene encoding a prokaryotic repressor (such as, for example, a tet repressor).

In another embodiment, the cell further comprises a gene capable of expressing a recombinase. In a specific embodiment, the recombinase is a Cre recombinase.

In one aspect, an isolated eukaryotic cell is provided that comprises an expression-enhancing sequence that is at least 80%, more preferably at least 90%, more preferably at least 95%, most preferably at least 99% identical to an expression-enhancing sequence of SEQ ID NO:1-6 or an expression-enhancing fragment thereof. In a specific embodiment, expression-enhancing sequence is a sequence within SEQ ID NO:5 as described above.

In one aspect, a eukaryotic host cell is provided, comprising an expression-enhancing sequence selected from SEQ ID NO:1-6 or an expression-enhancing fragment thereof, comprising a first recombinase recognition site followed by a first eukaryotic promoter, a first marker gene, a second eukaryotic promoter, a second marker gene, a second recombinase recognition site, a third eukaryotic promoter, a third marker gene, and a third recombinase recognition site. In one embodiment, the expression-enhancing sequence is within SEQ ID NO:5 as described above.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a puromycin resistance gene. In another embodiment, the second and third marker genes encode two different fluorescent proteins. In one embodiment, the two different fluorescent proteins are selected from *Discosoma* coral (DsRed), green fluorescent protein (GFP), enhanced green fluorescent protein (eGFP), cyano fluorescent protein (CFP), enhanced cyano fluorescent protein (eCFP), and yellow fluorescent protein (YFP). In a specific embodiment, the two different fluorescent proteins are eCFP and DsRed.

In one embodiment, the first, second, and third promoters are the same. In another embodiment, the first, second, and third promoters are different. In another embodiment, the first promoter is different from the second and third promoters, and the second and third promoters are the same. In a specific embodiment, the first promoter is an SV40 late promoter, and the second an third promoters are each a human CMV promoter.

In one aspect, a eukaryotic host cell is provided, comprising an expression-enhancing sequence selected from SEQ ID NO:1-6, or an expression-enhancing fragment thereof, at least one recombinase recognition site within the expression-enhancing sequence, and at least one gene of interest (GOI) within the expression-enhancing sequence. In one embodiment, the expression-enhancing sequence is a sequence within SEQ ID NO:5, as described above.

In one embodiment, the cell comprises a first recombinase recognition site followed by a first promoter operably linked to a first GOI. In another embodiment, the first GOI is followed by a second recombinase recognition site. In another embodiment, the second recombinase recognition site is followed by a second promoter operably linked to a second GOI. In another embodiment, the second GOI is followed by a third recombinase recognition site. In another embodiment, at least one marker is operably linked to a third promoter and is located between the second recombinase recognition site and the second promoter. In one embodiment, the first recombinase recognition site is oriented in an opposite orientation to the second and third recombinase recognition sites. In one embodiment the first and second promoters are eukaryotic promoters operably linked to a prokaryotic operator. In one embodiment, the first and second promoters are CMV promoters operably linked to tet operator sequences. In another embodiment, the cell further comprises a gene capable of expressing a prokaryotic repressor. In one embodiment, the prokaryotic repressor is a tet repressor. In one embodiment, the cell comprises a gene capable of expressing a Cre recombinase.

In one embodiment, a first and a second marker gene are located between the second recombinase recognition site and the second promoter, and an IRES is between the first and second marker genes. In another embodiment, the first codon (ATG) of the first marker gene is immediately 5' to the second recombinase recognition site, and the second codon of the first marker gene is immediately 3' to the second recombinase recognition site. In another embodiment, the first marker gene contains an intron and the second recombinase recognition site is located within the intron such that the amino-terminal half of the first marker gene and the 5' half of the intron are located 5' of the second recombinase recognition site and the 3' half of the intron and carboxy-terminal half of the first marker gene are immediately 3' to the second recombinase recognition site.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a hygromycin resistance gene. In another embodiment, the second marker gene encodes a fluorescent protein. In one embodiment, the fluorescent protein is selected from DsRed, GFP, eGFP, CFP, eCFP, and YFP.

In one embodiment, the first, second, and third promoters are the same. In another embodiment, the first, second, and third promoters are different. In another embodiment, the third promoter is different from the first and second promoters, and the first and second promoters are the same. In a specific embodiment, the third promoter is an SV40 late promoter, and the first and second promoters are each a human CMV promoter.

In one embodiment, the first and second promoters are operably linked to a prokaryotic operator. In a specific embodiment, the operator is a tet operator.

In one embodiment, the host cell line has an exogenously added gene encoding a recombinase integrated into its genome, operably linked to a promoter. In a specific embodiment, the recombinase is Cre recombinase. In another embodiment, the host cell has a gene encoding a regulatory protein integrated into its genome, operably linked to a promoter. In a specific embodiment, the regulatory protein is a tet repressor protein.

In one embodiment, the first GOI and the second GOI encode a light chain, or fragment thereof, of an antibody or a heavy chain, or fragment thereof, of an antibody. In a specific embodiment, the first GOI encodes a light chain of an antibody and the second GOI encodes a heavy chain of an antibody.

In one aspect, a method is provided for making a protein of interest, comprising: (a) providing a host cell that comprises an expression-enhancing sequence selected from a sequence of SEQ ID NO:1-6; (b) introducing into the host cell, within the expression-enhancing sequence, a gene of interest (GOI) operably linked to a promoter; (c) maintaining the host cell of (a) under conditions that allow the GOI to express a protein of interest; and, (c) recovering the protein of interest.

In one embodiment, the cell is a CHO cell and the nucleotide sequence is an expression-enhancing sequence of SEQ ID NO:5 as described above.

In one embodiment, the GOI is introduced into the cell employing a targeting vector for homologous recombination, wherein the targeting vector comprises a 5' homology arm homologous to a sequence present in at least one of SEQ ID NO:1-6, a GOI, and a 3' homology arm homologous to a sequence present in at least one of SEQ ID NO:1-6. In another embodiment, the construct further comprises two, three, four, or five or more genes of interest. In another embodiment, one or more of the genes of interest are operably linked to a promoter.

In another embodiment, the GOI is introduced employing an integrase technology, for example, integrase technology employing att sites such as Invitrogen's Gateway™ and Multisite Gateway™ cloning systems which employ bacteriophage lambda att site recombination.

In another embodiment, the expression-enhancing sequence comprises one or more recombinase recognition sites as described above, and the GOI is introduced into the expression-enhancing sequence through the action of a recombinase that recognizes the recombinase recognition site.

In one embodiment, the expression-enhancing sequence comprises two recombinase recognition sites.

In one embodiment, the expression-enhancing sequence comprises a first, a second, and a third recombinase recognition site. In one embodiment, the first, second, and third recombinase recognition sites are different. In another embodiment, the first, second, and third recombinase recognition sites are not in the same orientation. In a specific embodiment, the first site is 5' to the second site, and the second site is 5' to the third site. In another specific embodiment, the second and third sites are in opposite orientation with respect to the first site.

In another embodiment, a first and a second GOI are introduced into the expression-enhancing sequence. In one embodiment, the first GOI is introduced between the first and the second recombinase recognition sites, and the second GOI is introduced between the second and the third recombinase recognition sites. In a specific embodiment, the recombinase recognition sites are independently selected from a loxp site, a lox 511 site, a lox 2272 site, and a frt site.

In another embodiment, the first GOI flanked by recombinase recognition sites on a first vector and the second GOI flanked by recombinase recognition sites on a second vector are introduced into a cell comprising an expression-enhancing sequence that comprises three recombinase recognition sites in a single step.

In one embodiment, the GOI is operably linked to a eukaryotic promoter. In another embodiment, the eukaryotic promoter is operably linked to a prokaryotic operator. In a specific embodiment, the eukaryotic promoter is a CMV promoter and the prokaryotic operator is a tet operator.

In another embodiment, the cell comprises a gene capable of expressing a prokaryotic repressor. In a specific embodiment, the prokaryotic repressor is a tet repressor.

In another embodiment, the cell comprises a gene capable of expressing a recombinase. In a specific embodiment, the recombinase is a Cre recombinase.

In one aspect, a eukaryotic cell is provided, wherein the eukaryotic cell comprises at least one expression-enhancing sequence of SEQ ID NO:1-6 and at least one exogenously added gene within the expression-enhancing sequence. In one embodiment, the exogenously added gene is operably linked to an exogenously added promoter.

In one embodiment, the expression-enhancing sequence is a sequence of SEQ ID NO:5, and the at least one exogenously added gene integrated or inserted within the expression-enhancing sequence is a human gene. In a specific embodiment, the eukaryotic cell is a CHO cell, the exogenously added gene is a human gene, and the human gene is operably linked to an exogenously added eukaryotic promoter.

In one aspect, a targeting vector for homologous recombination is provided, wherein the targeting vector comprises a 5' homology arm, a GOI, and a 3' homology arm, wherein each homology arm is homologous to a sequence within one of SEQ ID NO:1-6. In one embodiment, the 5' and 3' homology arms are homologous to sequences within SEQ ID NO:5. In one embodiment, the targeting vector comprises two, three, four, or five or more genes of interest. In one embodiment, the GOI is operably linked to a promoter. In another embodiment, each of the two, three, four, or five or more genes of interest are each operably linked to a promoter.

In one aspect, an expression vector is provided, comprising an expression-enhancing nucleotide sequence selected from SEQ ID NO: 1-6 or an expression-enhancing fragment thereof. In one embodiment, the expression-enhancing sequence is within SEQ ID NO:5 as described above.

In one embodiment, the vector further comprises a promoter. In a specific embodiment, the promoter is a human CMV promoter.

In one embodiment, the vector further comprises a cloning site for an expressible gene of interest (GOI). In one embodiment, the nucleotide sequence selected from SEQ ID NO: 1-6 or expression-enhancing fragment thereof is located 3' with respect to the cloning site for the expressible GOI. In another embodiment, the nucleotide sequence selected from SEQ ID NO: 1-6 or expression-enhancing fragment thereof is located 5' with respect to the cloning site for the expressible GOI.

In a specific embodiment, the vector comprises a nucleotide sequence selected from SEQ ID NO:1-6 or an expression-enhancing fragment, a human CMV promoter, a GOI, and a termination sequence, wherein the nucleotide sequence selected from SEQ ID NO: 1-6, or the expression-enhancing fragment thereof, is located 5' with respect to the CMV promoter. In a specific embodiment, the vector further comprises an intron selected from a CMV-MIE intron and a rabbit β-globin intron.

In one aspect, an expression vector is provided, comprising an expression-enhancing nucleotide sequence that is at least 80% identical, preferably at least 90% identical, more preferably at least 95% identical, most preferably at least 99% identical to a sequence selected from SEQ ID NO:1-6 or an expression-enhancing fragment thereof.

In one aspect, a method is provided for making a protein of interest, comprising: (a) introducing into a host cell an expression vector comprising an expression-enhancing sequence selected from a sequence within SEQ ID NO:1-6 and a GOI that encodes for a protein of interest, wherein the GOI is operably linked to a promoter and operably linked to the expression-enhancing sequence; (b) culturing the host cell of (a) under conditions that allow expression of the GOI; and (c) recovering the protein of interest.

In one embodiment, the enhanced expression and stability region sequence is an expression-enhancing sequence of SEQ ID NO:1-6. In one embodiment, the expression-enhancing sequence is within SEQ ID NO:5 as described above.

In one embodiment, the recombinant protein is selected from the group consisting of a subunit of an immunoglobulin or fragment thereof and a receptor or ligand-binding fragment thereof. In a specific embodiment, the recombinant protein is selected from the group consisting of an antibody light chain or antigen-specific fragment thereof, and an antibody heavy chain or antigen-specific fragment thereof.

In any of the aspects and embodiments described above, the expression-enhancing sequence can be placed in the indicated orientation as indicated in SEQ ID NO:1-6, or in the reverse of the orientation indicated in SEQ ID NO:1-6.

Any of the aspects and embodiments of the invention can be used in conjunction with any other aspect or embodiment of the invention, unless otherwise specified or apparent from the context.

Other objects and advantages will become apparent from a review of the ensuing detailed description.

BRIEF DESCRIPTION OF THE FIGURES

FIGS. 3A and 3B show an alignment of Chinese hamster ovary (CHO), mouse, human, and rat EESYR sequences for a fragment of SEQ ID NO:5.

DETAILED DESCRIPTION

Figure 1:
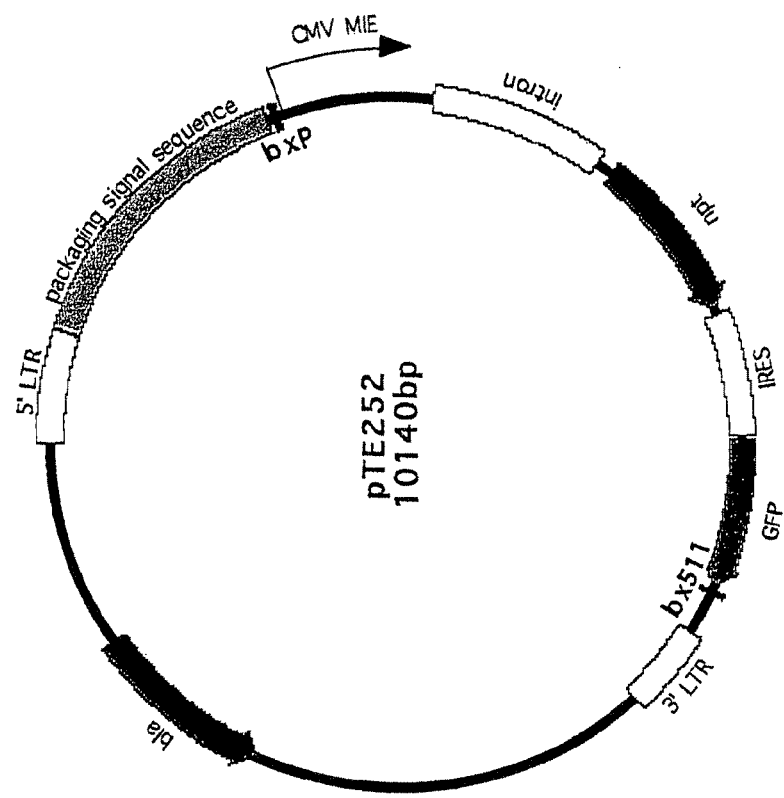
FIG. 1. Schematic diagram of a retroviral construct, pTE252, used for the introduction of nucleic acid construct into a cell genome. LTR: long terminal repeat; LoxP: Cre recombinase recognition sequence: ATAACTTCGTATAATGTATGCTACGAAGTTGT (SEQ ID NO:7); Lox511: a mutation of LoxP sequences: ATAACTTCGTATAATG-TATACTATACGAAGTTAG (SEQ ID NO:8); the Lox511 sequence is recognized by Cre recombinase but the Lox511 site does not recombine with a LoxP site. GFP: Green fluorescent protein; CMV MIE: human cytomegalovirus major immediate early promoter; npt: neomycin phosphotransferase; bla: beta lactamase; IRES: internal ribosomal entry site.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, or otherwise specified, all technical and scientific terms used herein have the same meaning as commonly understood by one of ordinary skill in the art to which this invention belongs.

Although any methods and materials similar or equivalent to those described herein can be used in the practice or testing of the present invention, particular methods and materials are now described. All publications mentioned herein are incorporated herein by reference in their entirety.

gene from another locus in the hamster genome), a gene from any other species (e.g., a human gene), a chimeric gene (e.g., human/mouse), or any other gene not found in nature to exist within the CHO EESYR.

Percent identity, when describing an EESYR, is meant to include homologous sequences that display the recited identity along regions of contiguous homology, but the presence of gaps, deletions, or insertions that have no homolog in the compared sequence are not taken into account in calculating percent identity. In explaining the usage of "percent identity" in this context, the following sequence comparison (SEQ ID NO:9-SEQ ID NO:12) will be referred to:

```
EESYR       5595 AGATTCTGTGGGCTCTGAGGCAACTTGACCTCAGCCAGATGGTATTTGAATAACCTGCTC 5654

Rat Ch3     5619 AGATTCTGTGGGTTCTGAGACAACTTGACTTCAGCCAGATGGCATTTGAATAAC------ 5672

M Mus Ch2   6618 AGATTCTGTGGGTTCTGAGACAACTTGACTTTAGCCAGATGGTATTTGAGTAATCTGGG- 6676

H. Sap. Ch20 6620 AGATTCAGTGGGCTTTGGGACAGCTTGACTTCAACTAGATGGTATTTGAATAATCTGCT- 6678
                  ****** ***** * ** * ** ****** * * * ****** ****** ***
```

Definitions

DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. An EESYR is operably linked to a GOI where it is functionally related to the gene of interest, for example, where its presence results in enhanced expression of the GOI.

The term "enhanced" when used to describe enhanced expression includes an enhancement of at least about 1.5-fold to at least about 2-fold enhancement in expression over what is typically observed by random integration into a genome, for example, as compared to a pool of random integrants of a single copy of the same expression construct. Fold-expression enhancement observed employing the sequences of the invention is in comparison to an expression level of the same gene, measured under substantially the same conditions, in the absence of a sequence of the invention. As used herein, the phrase "expression-enhancing" is used interchangeably with "enhanced expression and stability" when referring to a region or sequence. An "enhanced expression and stability region," also referred to herein as an "EESYR," is a region or sequence that exhibits more efficient recombination, insert stability, and higher level expression than is typically observed by random integration into a genome.

Enhanced recombination efficiency includes an enhancement of the ability of a locus to recombine (for example, employing recombinase-recognition sites). Enhancement refers to an efficiency over random recombination, which is typically 0.1%. A preferred enhanced recombination efficiency is about 10-fold over random, or about 1%. Unless specified, the claimed invention is not limited to a specific recombination efficiency.

Where the phrase "exogenously added gene" or "exogenously added GOI" is employed with reference to a EESYR, the phrase refers to any gene not present within the EESYR as the EESYR is found in nature. For example, an "exogenously added gene" within a CHO EESYR (e.g., an EESYR comprising a sequence of SEQ ID NO:5), can be a hamster gene not found within the CHO EESYR in nature (i.e., a hamster in which the "EESYR" 5595-5654 sequence is SEQ ID NO:9, the "Rat Ch3" 5619-5672 sequence is SEQ ID NO:10, the "M Mus Ch2" 6618-6676 sequence is SEQ ID NO:11, and the "H. Sap. Ch20" 6620-6678 sequence is SEQ ID NO:12. As used herein, a "percent identity" determination between the "EESYR" sequence above (for a CHO cell ESSYR or fragment thereof) with a rat homolog ("Rat Ch3") would not include a comparison of CHO sequences 5649 through 5654, since the rat homolog has no homologous sequence to compare in an alignment (i.e., the CHO EESYR has an insertion at that point, or the rat homolog has a gap or deletion, as the case may be). Thus, in the comparison above, the percent identity comparison would extend from the "AGATTC" at the 5' end to the "AATAAC" at the 3' end. In that event, the rat homolog differs only in that it has a "T" at CHO EESYR position 5607, and "A" at CHO EESYR position 5614, a "T" at CHO EESYR position 524, and a "C" at CHO EESYR position 5637. Since the comparison is over 54 contiguous bases in a 60 base pair stretch, with only four differences (which are not gaps, deletions, or insertions), there is over 90% identity between the two sequences (CHO and rat) from CHO EESYR position 5595 to CHO EESYR position 5654 (because "percent identity" does not include penalties for gaps, deletions, and insertions).

General Description

The invention is based at least in part on the discovery that there are sequences in a genome that exhibit more efficient recombination, insert stability, and higher level expression than other regions or sequences in the genome. The invention is also based at least in part on the finding that when such expression-enhancing sequences are identified, a suitable gene or construct can be exogenously added in or near the sequences and that the exogenously added gene can be advantageously expressed. Such sequences, termed enhanced expression and stability regions ("EESYRs"), can be engineered to include recombinase recognition sites for placement of genes of interest to create cell lines that are capable of expressing proteins of interest. EESYRs can also be included as in expression constructs such as, for example, expression vectors. Expression vectors comprising EESYRs can be used to express proteins transiently, or can be integrated into a genome by random or targeted recombination such as, for example, homologous recombination or recombination mediated by recombinases that recognize specific recombination sites (e.g., Cre-lox-mediated recombination). Expression vectors comprising EESYRs can also be used to assess efficacy of other DNA sequences, for example, cis-acting regulatory sequences.

The CHO EESYR described in detail herein was identified by random integration of DNA comprising lox sites into a CHO cell genome, followed by selection to identify sequences where expression was enhanced. Random integration and introduction of the lox site was achieved using a retroviral construct. Selection and screening were achieved using drug resistance markers and detectable labels (e.g., fluorescent proteins with FACS screening), employing recombination methods that used site-specific recombination (e.g., lox sites and Cre recombinase). Selection continued until at least a 1.5- to 2-fold enhanced expression over expression observed when randomly integrating an expression construct into the CHO cell genome. Following identification of the EESYR, recombinase recognition sites (in the example provided, lox sites) were maintained in the EESYR for introducing expression cassettes that comprise an expressible GOI, along with any other desirable elements such as, for example, promoters, enhancers, markers, operators, etc.

Figure 2:
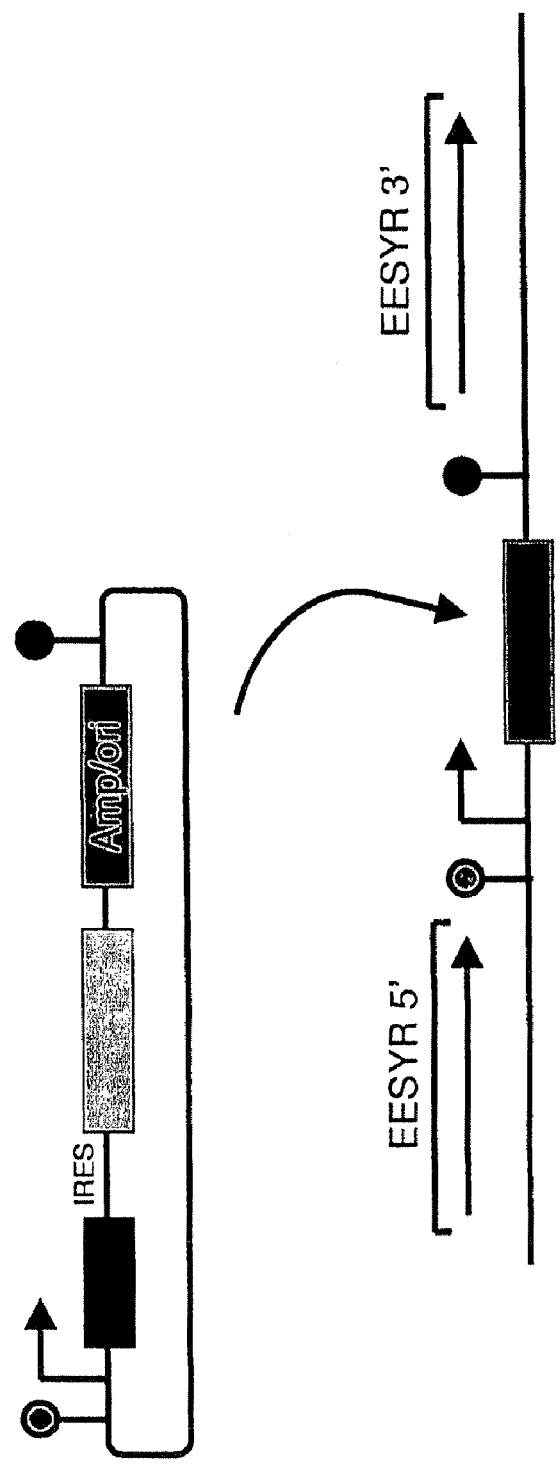
FIG. 2 illustrates a plasmid construct used to identify an EESYR.

An illustration of a plasmid construct used in identifying an EESYR disclosed in this application is shown in FIG. 2. The plasmid rescue construct comprises an expression cassette driven by a promoter, wherein the cassette is flanked on the 5' and 3' ends with recombinase recognition sites (represented by ball-and-stick in FIG. 2). Insertion within an EESYR locus is shown, wherein the insertion results in the plasmid rescue construct replacing an expression cassette that comprises a promoter and a marker, wherein the expression cassette within the EESYR locus is flanked on its 5' and 3' ends by recombinase recognition sites (see FIG. 2).

Compositions and methods are provided for stably integrating a nucleic acid sequence into a eukaryotic cell, wherein the nucleic acid sequence is capable of enhanced expression by virtue of being integrated in or near an EESYR. Cells are provided that contain a recombinase recognition sequence within or near an EESYR, convenient for inserting a GOI, in order to achieve expression of a protein of interest from the GOI. Compositions and methods are also provided for using EESYRs in connection with expression constructs, for example, expression vectors, and for adding an exogenous EESYR into a eukaryotic cell of interest.

Physical and Functional Characterization of an EESYR

The nucleic acid sequences referred to as EESYRs were empirically identified by sequences upstream and downstream of the integration site of a nucleic acid construct (comprising an expression cassette) of a cell line expressing a reporter protein at a high level. The EESYR nucleic acid sequences of the invention provide sequences with a new functionality associated with enhanced expression of a nucleic acid (for example, an exogenous nucleic acid comprising a GOI) that appear to function differently from that previously described for cis-acting elements such as promoters, enhancers, locus control regions, scaffold attachment regions or matrix attachment regions. EESYRs do not appear to have any open reading frames (ORFs), making it unlikely that EESYRs encode novel trans-activator proteins. Transfection experiments demonstrated that EESYR sequences display some characteristics of cis-acting elements. EESYR activity is not detected in transient transfection assays; EESYR sequences also appear to be distinct from promoter and enhancer elements, which are detected with these methods.

Although EESYR sequences described in detail herein were isolated from the genome of two cell lines, EESYR sequences from these two cell lines are the same. EESYR activity was identified in a 6.472 kb fragment of CHO genomic DNA 5' with respect to a unique integration site of a retroviral vector comprising a DsRed reporter encoding sequence and in a 7.045 kb fragment of CHO genomic DNA 3' with respect to the integration site. Expression vectors comprising the isolated 6.472 kb region and the isolated 7.045 kb region and shorter fragments thereof were able to confer upon CHO cells transfected with them high levels of expression of recombinant proteins.

The invention encompasses expression vectors comprising reverse orientated EESYR fragments. Reverse orientated EESYR fragments were also capable of conferring upon CHO cells transfected with them high levels of expression of recombinant proteins.

Other combinations of the fragments described herein can also be developed. Examples of other combinations of the fragments described herein that can also be developed include sequences that include multiple copies of the EESYR disclosed herein, or sequences derived by combining the disclosed EESYR with other nucleotide sequences to achieve optimal combinations of regulatory elements. Such combinations can be contiguously linked or arranged to provide optimal spacing of the EESYR fragments (e.g., by the introduction of spacer nucleotides between the fragments). Regulatory elements can also be arranged to provide optimal spacing of an EESYR with respect to the regulatory elements.

The EESYR sequences disclosed herein were isolated from CHO cells. Homologous expression-enhancing elements are expected to exist in cells from other mammalian species (such as, for examples, humans; see FIG. 3) as well as in cell lines derived from other tissue types, and can be isolated by techniques that are well-known in the art, for example, by cross-species hybridization or PCR-based techniques. In addition, changes can be made in the nucleotide sequence set forth in SEQ ID NOs:1-6 by site-directed or random mutagenesis techniques that are well known in the art. The resulting EESYR variants can then be tested for EESYR activity as described herein. DNAs that are at least about 80% identical, preferably at least about 90% identical, more preferably at least about 95% identical, most preferably least about 99% identical in nucleotide sequence to SEQ ID NOs:1-6 or fragments thereof having EESYR activity are isolatable by routine experimentation, and are expected to exhibit EESYR activity. For fragments of EESYR, percent identity refers to that portion of the reference native sequence that is found in the EESYR fragment. Accordingly, homologs of EESYR and variants of EESYR are also encompassed by embodiments of the invention. FIGS. 3A and B show an alignment of mouse, human, and rat sequences with varying homology to a fragment of SEQ ID NO:5.

Cell populations expressing enhanced levels of a protein of interest can be developed using the methods provided herein. The absolute level of expression will vary with the specific protein, depending on how efficiently the protein is processed by the cell. Cell pools developed with EESYR are stable over time, and can be treated as stable cell lines for most purposes. Cloning steps can be delayed until later in the process of development than is customary for recombinant proteins.

EESYRs and Expression-Enhancing Fragments Thereof

Figure 4:
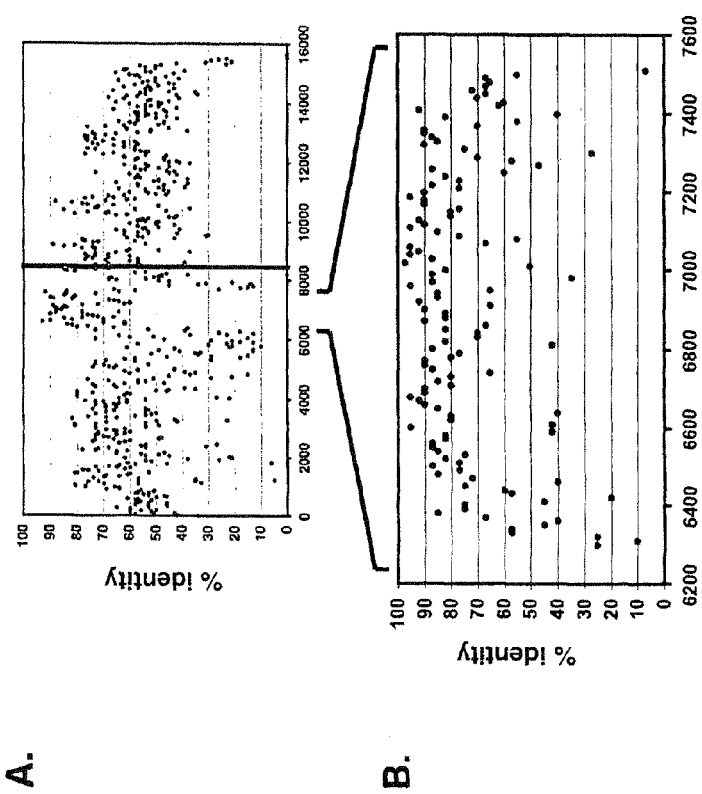
FIG. 4 shows an alignment of SEQ ID NO:5 with mouse, human, and rat sequences.

The EESYR genomic locus is conserved among human, mouse and rat genomes. FIG. 4 shows percent identity among EESYR sequences. EESYR sequences, homologous to the 13.515 kb of cloned CHO EESYR DNA of SEQ ID NO:5, were identified among the published human, rat and mouse genomes using BLAST. Sequences were aligned to determine the percent homology using MacVector (9.0). Twenty-five by increments of the alignment are graphed as the percent identity among CHO, human, mouse and rat EESYR sequences for each consecutive 25 bp segment. As shown in FIG. 4, the vertical line marks the location of site-specific recombination events to express recombinant protein genes of interest. Percent identity of EESYR sequences adjacent to a site-specific recombination location in an EESYR is shown in panel B of FIG. 4. Ten base pair increments of the aligned sequences corresponding to nt 5022-6110 of a CHO cell EESYR sequence (nucleotides 5022 through 6110 of SEQ ID NO:5) are graphed as the percent identity among CHO, human, mouse and rat EESYR sequences for each consecutive 10 by segment. Sequences were aligned using MacVector™ 9.0. As shown in panel B, a significant identity of sequence is present in this fragment of the EESYR cloned from CHO cells. It should be noted that the comparison of FIG. 4 indicates a length of about 1400 bases, whereas the sequence of SEQ ID NO:5 contains 13,515 bases. The FIG. 4 bases appear to extend over a longer stretch due to the existence of gaps. Nucleotide spans recited are those corresponding to numbering in SEQ ID NO:5 unless otherwise indicated. The span of nucleotides from about 6200 to about 7600 as shown in FIG. 4B corresponds to nucleotides of SEQ ID NO:5 numbered about 5,200 to about 6,000.

Accordingly, the invention also includes an expression-enhancing fragment of a nucleotide sequence of SEQ ID NO:5, wherein the expression-enhancing fragment includes the nucleotide sequence indicated by positions about residues 5022 through about 6110 of SEQ ID NO:5, or about 5218 through about 6048 of SEQ ID NO:5; or about 6200 through about 7600, about 6500 to about 7400, or about 6400 to about 6500 shown in panel B of FIG. 4. The invention also encompasses an expression-enhancing fragment of a nucleotide sequence that is at least 80% identical, preferably at least 90% identical, more preferably at least 95% identical, most preferably at least 99% identical to the nucleotide sequence indicated by positions about 6200 through about 7600, or about 6500 through about 7400, or about 6400 through about 6500 shown in panel B of FIG. 4. The invention includes vectors comprising such a fragment, including for transient or stable transfection. The invention also includes a eukaryotic cell comprising such a fragment wherein the fragment is exogenous and is integrated into the cell genome, and cells comprising such a fragment having at least one recombinase recognition site that is within, immediately 5', or immediately 3' to the fragment.

In one embodiment, the expression-enhancing fragment of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485.

Figure 5:
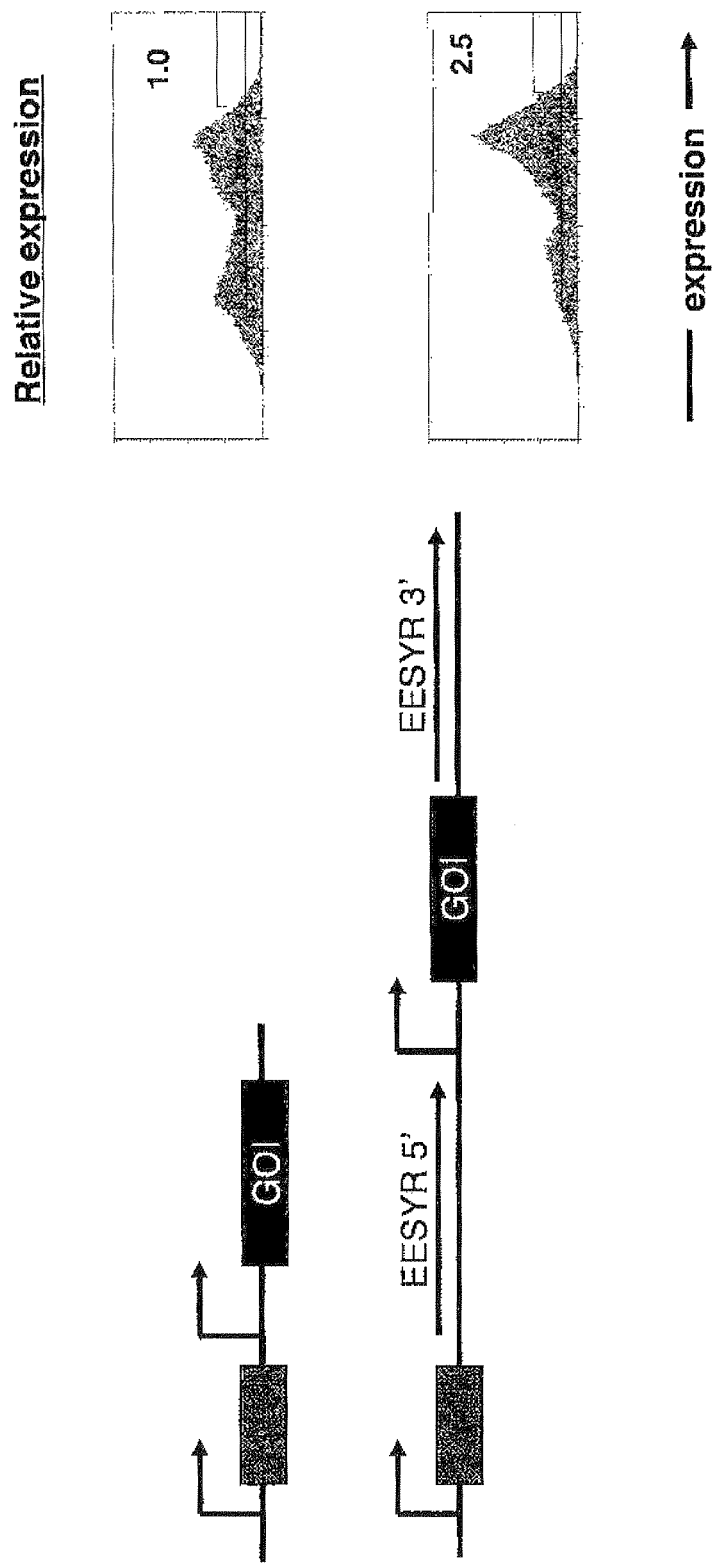
FIG. 5 illustrates that an EESYR, operably linked to a gene of interest (GOI), exhibits enhanced expression over a GOI that is not operably linked to an EESYR. For each plot, major ticks on the y-axis represent 0, 300, 600, 900, and 1200; major ticks on the x-axis represent $10^0$, $10^1$, $10^2$, $10^3$, and $10^4$.

In one embodiment, the EESYR is employed to enhance the expression of a GOI, as illustrated in FIG. 5. FIG. 5 shows a GOI operably linked with a promoter (with an upstream marker having its own promoter) integrated in a non-EESYR position in a CHO cell genome, and a FACS readout showing the distribution of expression in a stably transfected population of cells. In comparison, a GOI operably linked to a promoter integrated at an EESYR position in a CHO cell genome is shown, and a FACS readout showing the distribution of expression in a stably transfected population of cells is also shown. In this embodiment, the GOI expressed within the EESYR locus shows an enhanced expression of about two-fold in comparison to the GOI expressed at a non-EESYR locus.

In various embodiments, expression of a GOI can be enhanced by placing the GOI within an EESYR, 5' to an EESYR, or 3' to an EESYR. The precise distance between the GOI and the EESYR, where the GOI is either 5' or 3' to the EESYR, should be such that the EESYR is operably linked to the GOI. An EESYR is operably linked to the 001 where expression of the GOI—at the selected distance from the EESYR (in the 5' or 3' direction)—retains the ability to enhance expression of the GOI over, for example, expression typically observed due to a random integration event. In various embodiments, enhancement is at least about 1.5-fold to about 2-fold or more. Preferably, enhancement in expression as compared to a random integration, or random expression, is about 2-fold or more.

Figure 6:
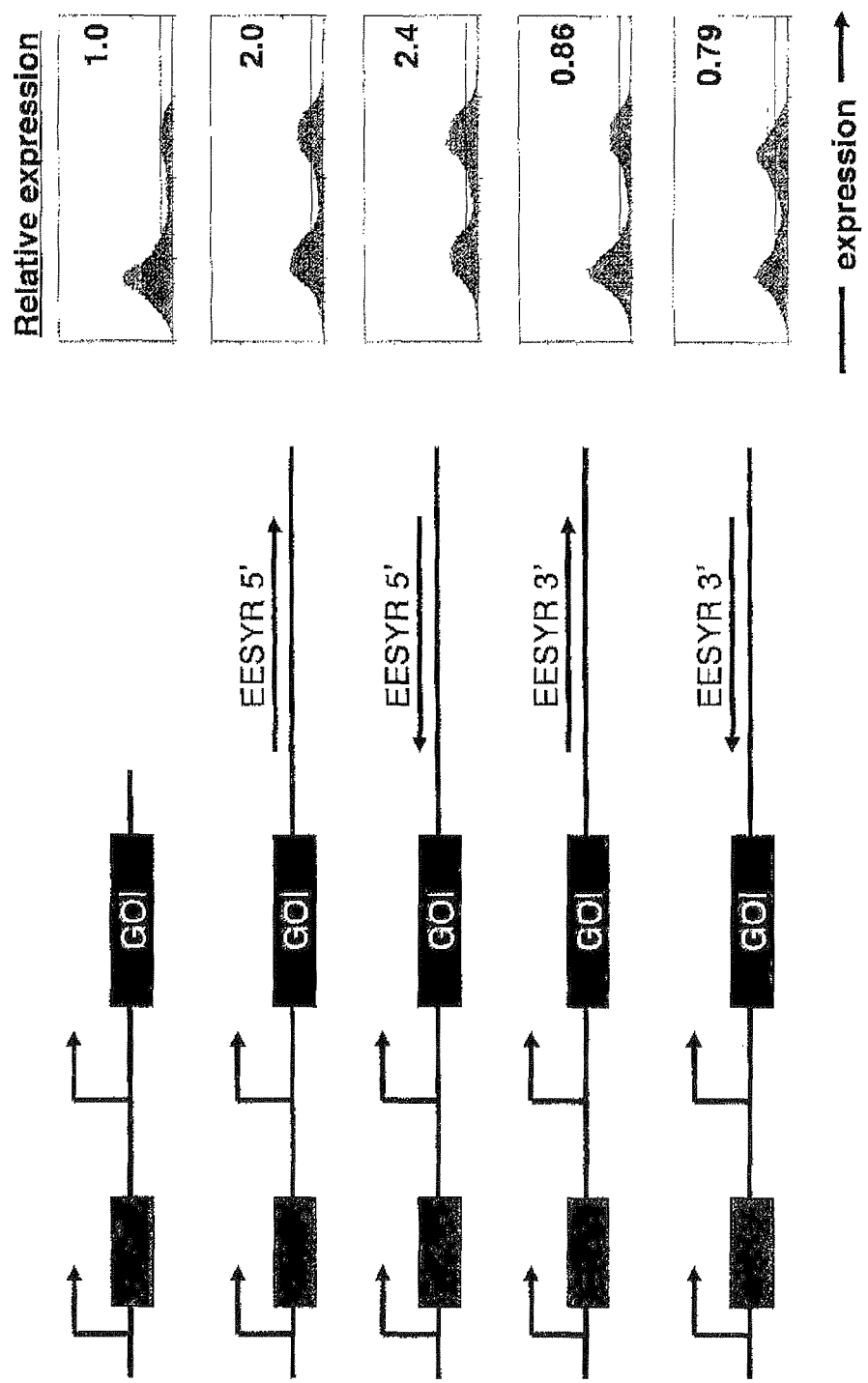
FIG. 6 shows EESYRs compared in their relative ability to enhance expression of an operably linked GOI. For each plot, y-axis major ticks represent Counts of 0, 500, 1,000, 1,500, and 2,000; x-axis major ticks represent FITC of 100, 101, 102, 103, and 104.

FIG. 6 shows an embodiment wherein SEQ ID NO:1 ("EESYR 5') and SEQ ID NO:2 ("EESYR 3'") are compared in their relative ability to enhance expression of an operably linked GOI, wherein the GOI is operably linked to a promoter as well (a marker and a promoter operably linked to the marker are shown 5' to the GOI promoter). Orientation of the EESYR is shown by the direction of the arrow beneath the term "EESYR." The constructs are randomly integrated into a CHO cell genome. Expression is relative to the randomly integrated construct that does not comprise any EESYR. FACS readouts showing relative expression are shown on the right. In FIG. 6, the first EESYR construct employs SEQ ID NO:1; the second EESYR construct employs SEQ ID NO:3; the third EESYR construct is SEQ ID NO:2; the fourth EESYR construct is SEQ ID NO:4. As shown in the figure, SEQ ID NO:3 displays a 2.4-fold enhancement in expression, and SEQ ID NO:1 displays a 2-fold enhancement of expression.

Figure 7:
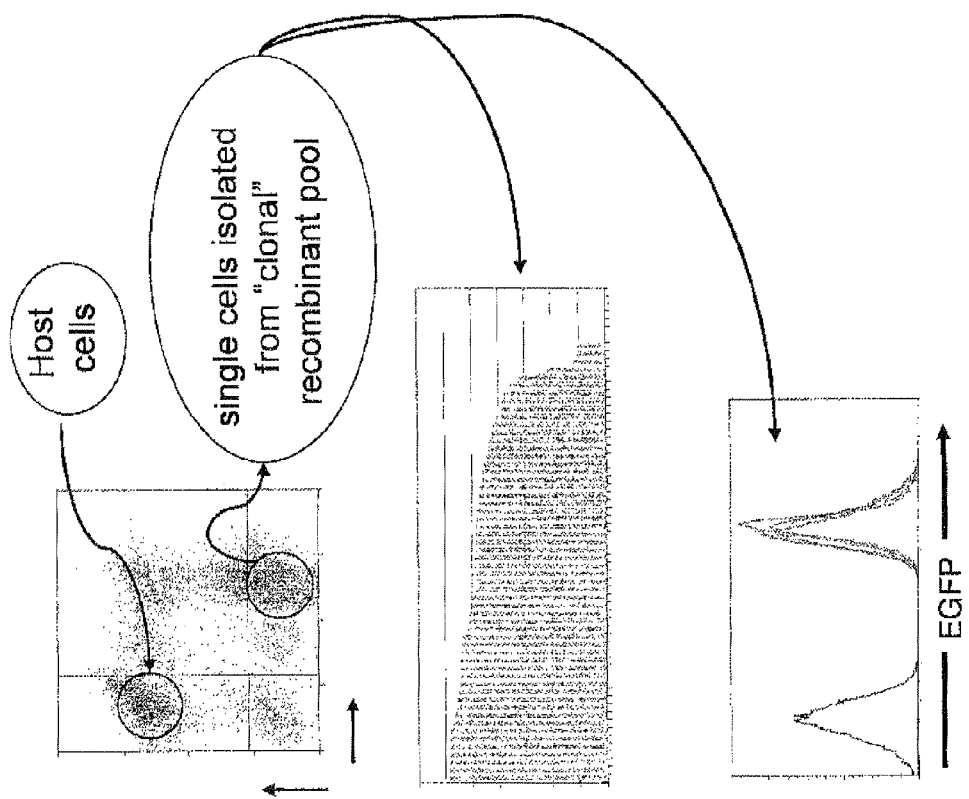
FIG. 7 illustrates clonal characteristics of cells with respect to EESYR functionality. For the top plot, major tick labels on both the y- and x-axes of the top plot represent 100, 101, 102, 103, and 104; quadrant identifiers are R10 and R11 (top, left to right) and R12 and R13 (bottom, left to right). For the middle plot, which shows 96-well plate ELISA results of sorted single cells, the y-axis of the center plot represents Titer (µg/ml), with major tick labels of 0, 2, 4, 6, 8, 10, 12, and 14; whereas the x-axis represents Clone Number (in triplicate) from 1 to 63. For the bottom plot, which shows clone stability after three months without selection, y-axis major ticks represent increments of 100 from 0 to 1000. For the bottom plot, the left peak is for "Host," whereas the right peak is for "Recombinant clones."

EESYR recombinant cell pools display clonal characteristics. FIG. 7 illustrates clonal characteristics of EESYR recombinant pools. In the two-color FACS plot representing a dual parameter histogram of cells labeled with red or green markers (red cells are host CHO cells; green cells are recombinants expressing a GOI), EESYR recombinant pools show clustering in the plot that reflects substantially identical growth and expression, flow cytometry profile, and Southern analysis (not shown). A histogram of ELISAs of single cells demonstrate uniform expression in all clones. Clonal stability is also high after three months without selection.

Figure 8:
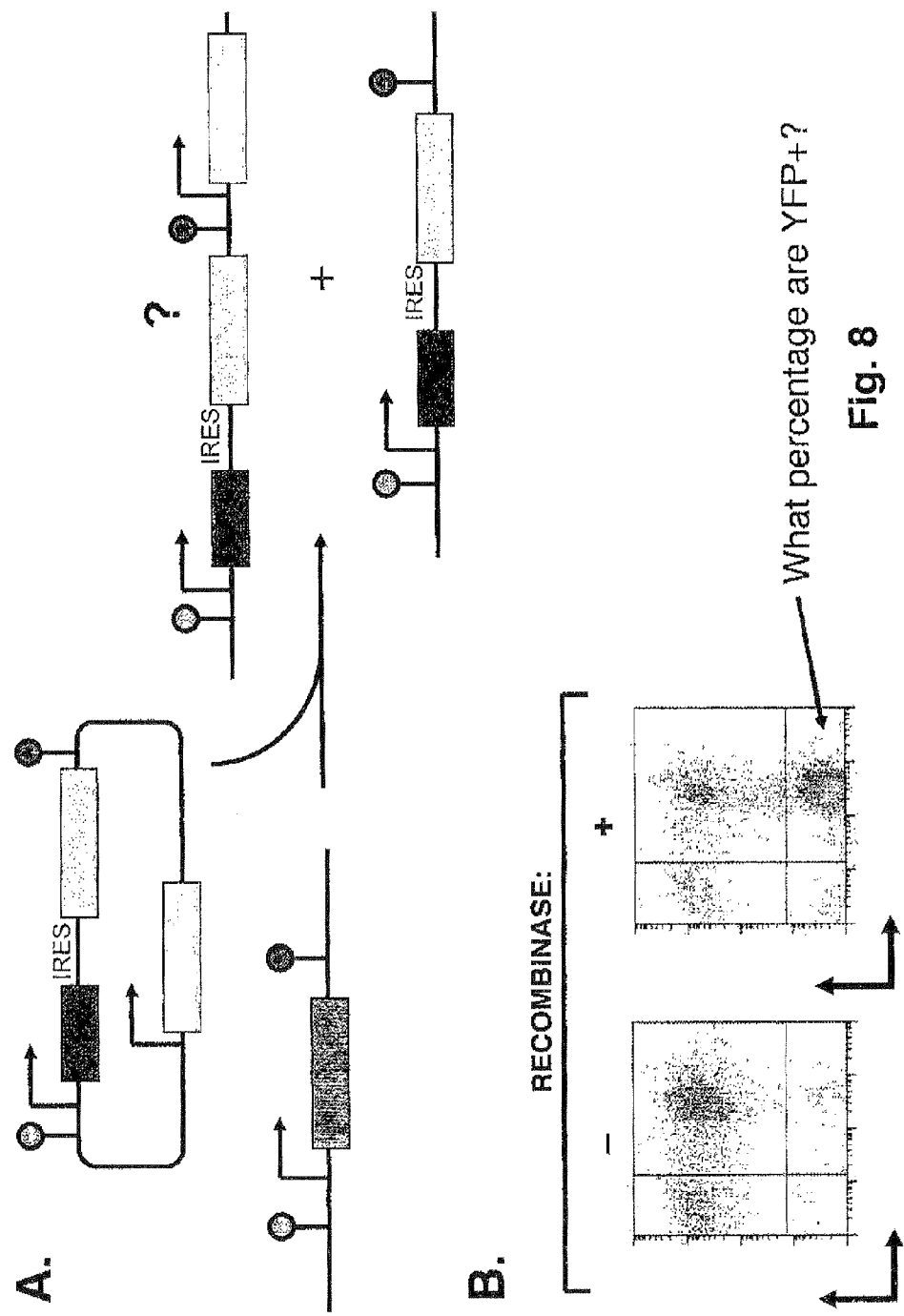
FIG. 8 illustrates that EESYR cells undergo specific and efficient recombination. In Panel B, y- and x-axes major ticks represent 100, 101, 102, 103, and 104; for each plot, quadrants are (left to right, top) R2 and R3, and (left to right, bottom) R4 and R5.

EESYR recombinants undergo specific and efficient recombination, as shown in FIG. 8. Panel A shows two markers separated by an IRES and flanked by recombinase recognition sites, and a third marker not flanked by recombinase recognition sites as a random integration control. When recombined at an EESYR locus comprising a marker flanked by two recombinase recognition sites, recombination is specific. Panel B shows little random integration in the absence of recombinase, but efficient and site-specific integration in the presence of recombinase.

Figure 9:
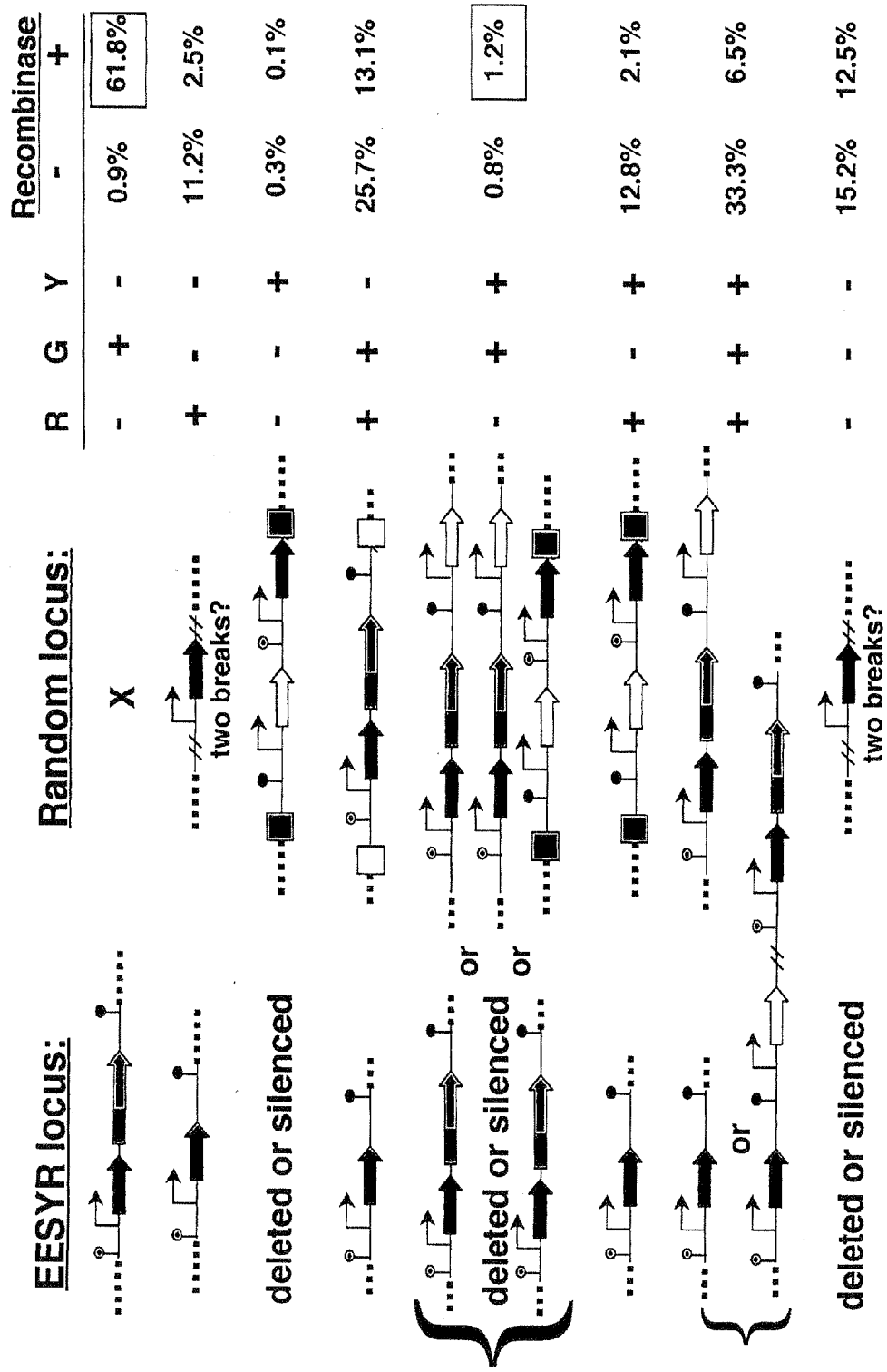
FIG. 9 illustrates the rarity of random integration events in EESYR cells.

Random integration using site specific recombination at an EESYR is rare (see FIG. 9). FIG. 9 shows that when random integration events are visualized, such events represent only a tiny fraction of integration events.

Figure 10:
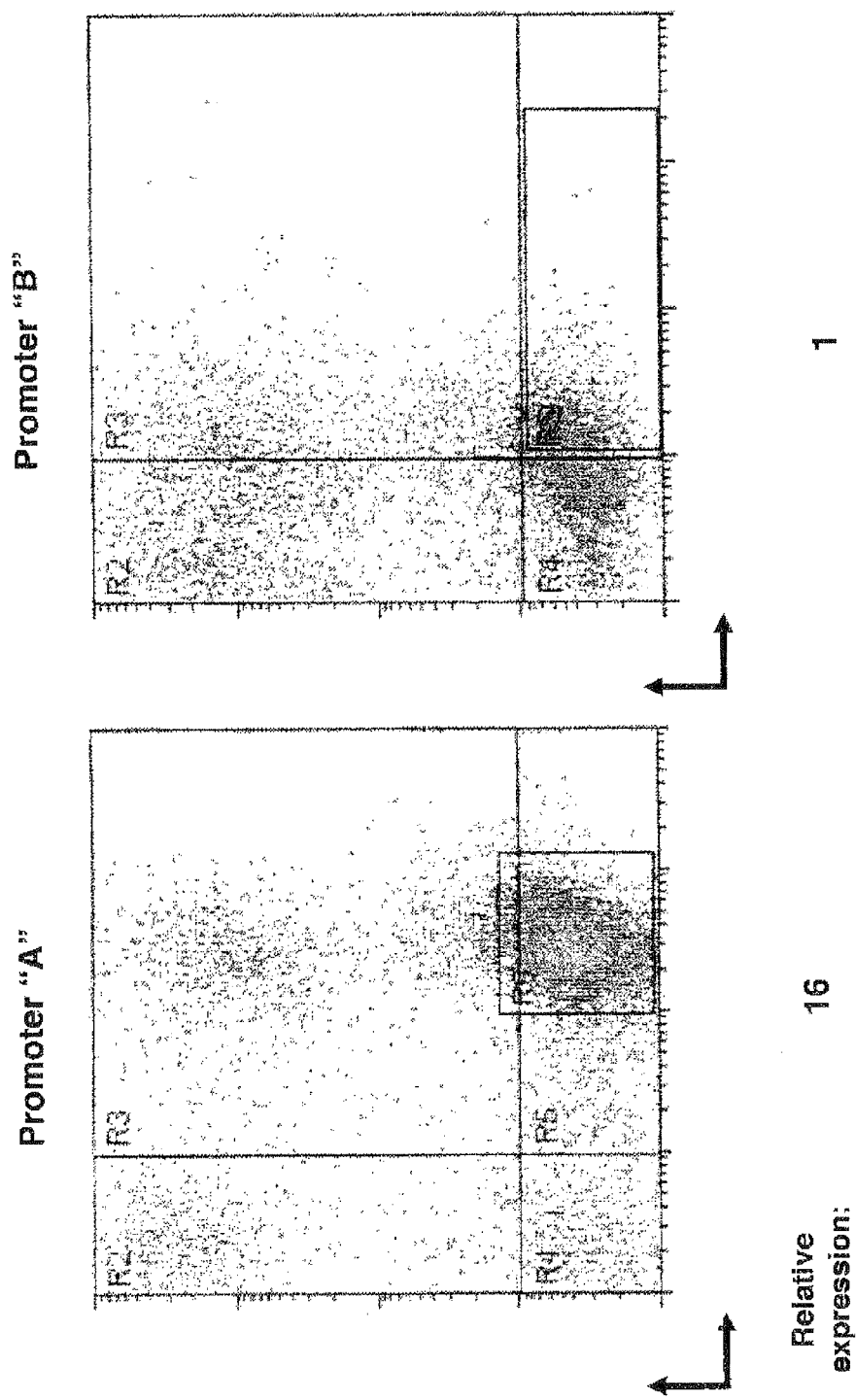
FIG. 10 illustrates testing of cis-acting elements employing EESYR sequences. Major ticks of the y- and x-axes represent 100, 101, 102, 103, and 104.
Figure 11:
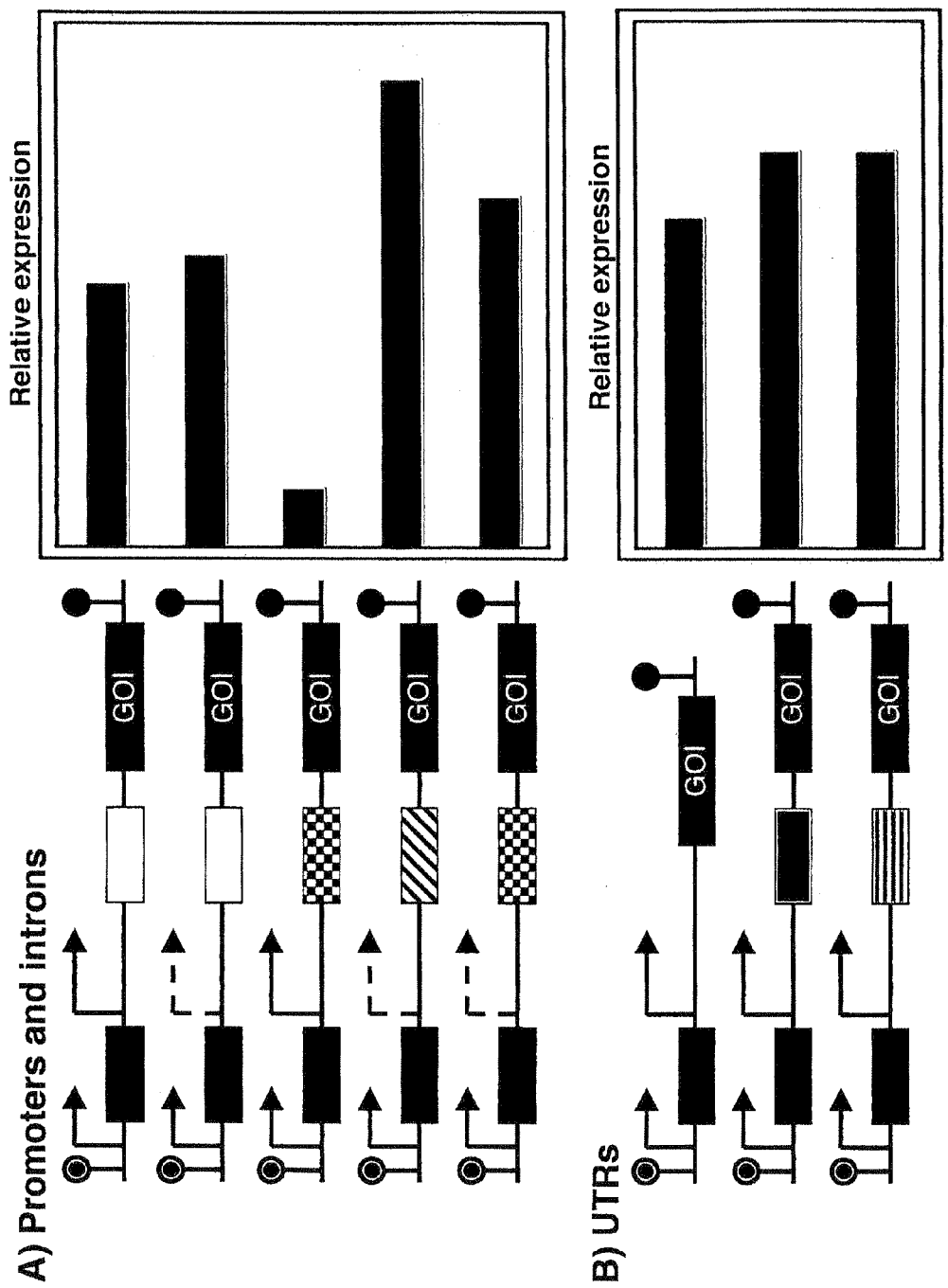
FIG. 11 illustrates testing promoters, introns, and UTRs using an EESYR system.

In another embodiment, EESYR cis-acting elements can be assessed using the methods and compositions of the invention. As shown in FIG. 10, EESYR recombinant cells, allows comparison of cis-acting elements equivalently. Because EESYR recombinants behave as a clonal population, differences in gene expression as the result of, for example, the presence or absence of suspected cis-acting elements, can be directly compared. Isogenic cell lines allow direct comparison of cis-acting elements. Using an EESYR system, cis-acting elements, such as, for example, promoters, introns, and UTRs, are preferably located between recombination sites. Expression optimization can also be achieved, including, for example, expression cassette orientation and codon optimization. By way of example, FIG. 11 shows cassettes flanked with recombination recognition sites that contain a promoter, a marker, various cis-elements (here, introns in panel A; UTRs in panel B), and a GOI were integrated at an EESYR (SEQ ID NO: 1 at the 5' end, SEQ ID NO:2 at the 3' end). Relative expression of the GOI is shown on the right.

Figure 12:
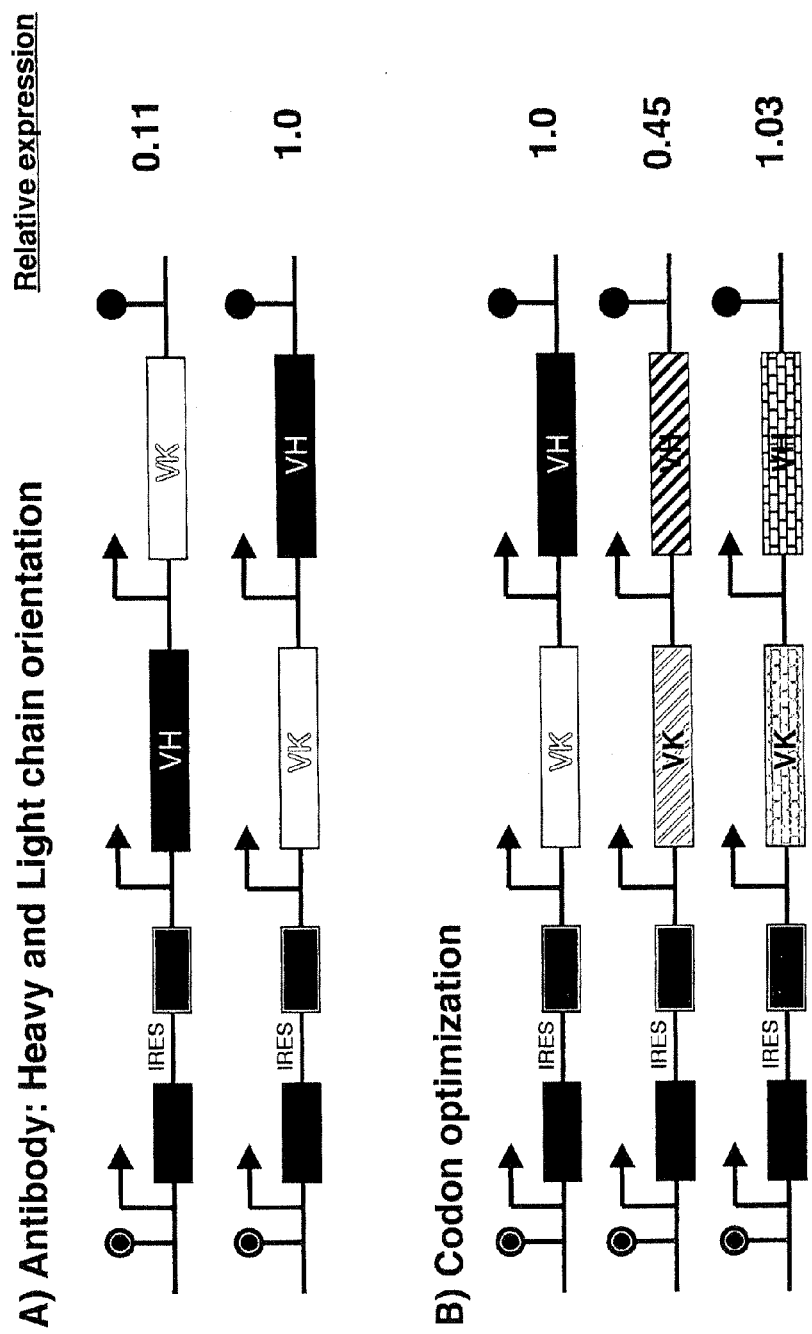
FIG. 12 illustrates optimizing protein expression using an EESYR system.

FIG. 12 shows an example of how protein optimization can be achieved using the methods and compositions of the invention. FIG. 12 confirms that optional placement of a cDNA for a light chain antibody gene is 5' to the a cDNA for a heavy chain antibody gene.

Proteins of Interest

A nucleic acid sequence encoding a protein of interest can be conveniently integrated into a cell comprising an EESYR having a recombinase recognition site through, for example, a recombinase-mediated cassette exchange (RMCE) process. Any protein of interest suitable for expression in eukaryotic cells can be used. For example, the protein of interest can be an antibody or fragment thereof, a chimeric antibody or fragment thereof, an ScFv or fragment thereof, an Fc-tagged protein or fragment thereof, a growth factor or a fragment thereof, a cytokine or a fragment thereof, or an extracellular domain of a cell surface receptor or fragment thereof.

Nucleic Acid Constructs

Recombinant expression vectors can comprise synthetic or cDNA-derived DNA fragments encoding a protein, operably linked to a suitable transcriptional and/or translational regulatory element derived from mammalian, viral or insect genes. Such regulatory elements include transcriptional promoters, enhancers, sequences encoding suitable mRNA ribosomal binding sites, and sequences that control the termination of transcription and translation, as described in detail below. Mammalian expression vectors can also comprise nontranscribed elements such as an origin of replication, other 5' or 3' flanking nontranscribed sequences, and 5' or 3' nontranslated sequences such as splice donor and acceptor sites. A selectable marker gene to facilitate recognition of transfectants may also be incorporated.

Transcriptional and translational control sequences in expression vectors useful for transfecting vertebrate cells may be provided by viral sources. For example, commonly used promoters and enhancers are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the recombinant protein is to be expressed.

DNA sequences derived from the SV40 viral genome, for example, the SV40 origin, early and late promoter, enhancer, splice, and polyadenylation sites may be used to provide other genetic elements useful for expression of a heterologous DNA sequence. Early and late promoters are particularly useful because both are obtained easily from the SV40 virus as a fragment that also comprises the SV40 viral origin of replication (Fiers et al., Nature 273:113, 1978). Smaller or larger SV40 fragments may also be used. Typically, the approximately 250 by sequence extending from the Hind III site toward the BglI site located in the SV40 origin of replication is included.

Bicistronic expression vectors used for the expression of multiple transcripts have been described previously (Kim S. K. and Wold B. J., Cell 42:129, 1985; Kaufman et al. 1991, supra) and can be used in combination with an EESYR sequence of the invention. Other types of expression vectors will also be useful, for example, those described in U.S. Pat. No. 4,634,665 (Axel et al.) and U.S. Pat. No. 4,656,134 (Ringold et al.).

Host Cells and Transfection

The eukaryotic host cells used in the methods of the invention are mammalian host cells, including, for example, CHO cells and mouse cells. In a preferred embodiment, the invention provides a nucleic acid sequence that encodes an EESYR sequence from a CHO cell. An integration site, for example, a recombinase recognition site, can be placed within an EESYR, or 5' or 3' to the EESYR sequence. One example of a suitable integration site is a lox p site. Another example of a suitable integration site is two recombinase recognition sites, for example, a lox p site and a lox 5511 site. In one embodiment, the EESYR sequence is located on chromosome 6 of a CHO cell genome. In specific embodiments, the EESYR sequence is located within a sequence selected from the group consisting of nucleic acids comprising nucleotides 1-6473 and 4607-6473 of SEQ ID NO: 1; and 1-7045, 1-3115, 1-2245, 1-1935, and 1-465 of SEQ ID NO:2.

The invention includes a mammalian host cell transfected with an expression vector of the invention. While any mammalian cell may be used, the host cell is preferably a CHO cell.

Transfected host cells include cells that have been transfected with expression vectors that comprise a sequence encoding a protein or polypeptide. Expressed proteins will preferably be secreted into the culture medium, depending on the nucleic acid sequence selected, but may be retained in the cell or deposited in the cell membrane. Various mammalian cell culture systems can be employed to express recombinant proteins. Examples of suitable mammalian host cell lines include the COS-7 lines of monkey kidney cells, described by Gluzman (1981) Cell 23:175, and other cell lines capable of expressing an appropriate vector including, for example, CV-1/EBNA (ATCC CRL 10478), L cells, C127, 3T3, CHO, HeLa and BHK cell lines. Other cell lines developed for specific selection or amplification schemes will also be useful with the methods and compositions provided herein. A preferred cell line is the CHO cell line designated K1. In order to achieve the goal of high volume production of recombinant proteins, the host cell line should be pre-adapted to bioreactor medium in the appropriate case.

Several transfection protocols are known in the art, and are reviewed in Kaufman (1988) Meth. Enzymology 185:537. The transfection protocol chosen will depend on the host cell type and the nature of the GOI, and can be chosen based upon routine experimentation. The basic requirements of any such protocol are first to introduce DNA encoding the protein of interest into a suitable host cell, and then to identify and isolate host cells which have incorporated the heterologous DNA in a relatively stable, expressible manner.

One commonly used method of introducing heterologous DNA into a cell is calcium phosphate precipitation, for example, as described by Wigler et al. (Proc. Natl. Acad. Sci. USA 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., (1980) Proc. Natl. Acad. Sci. USA 77:2163) is another useful method of introducing heterologous DNA. Protoplast fusion protocols frequently yield multiple copies of the plasmid DNA integrated into the mammalian host cell genome, and this technique requires the selection and amplification marker to be on the same plasmid as the GOI.

Electroporation can also be used to introduce DNA directly into the cytoplasm of a host cell, for example, as described by Potter et al. (Proc. Natl. Acad. Sci. USA 81:7161, 1988) or Shigekawa et al. (BioTechniques 6:742, 1988). Unlike protoplast fusion, electroporation does not require the selection marker and the GOI to be on the same plasmid.

More recently, several reagents useful for introducing heterologous DNA into a mammalian cell have been described. These include Lipofectin™ Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

A method for amplifying the GOI is also desirable for expression of the recombinant protein, and typically involves the use of a selection marker (reviewed in Kaufman supra). Resistance to cytotoxic drugs is the characteristic most frequently used as a selection marker, and can be the result of either a dominant trait (e.g., can be used independent of host cell type) or a recessive trait (e.g., useful in particular host cell types that are deficient in whatever activity is being selected for). Several amplifiable markers are suitable for use in the expression vectors of the invention (e.g., as described in Maniatis, Molecular Biology: A Laboratory Manual, Cold Spring Harbor Laboratory, NY, 1989; pgs 16.9-16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytotoxic agents (e.g., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifiable (Kaufman, R. J., supra,). Several suitable selection systems exist for mammalian hosts (Maniatis supra, pgs 16.9-16.15). Co-transfection protocols employing two dominant selectable markers have also been described (Okayama and Berg, Mol. Cell Biol 5:1136, 1985).

Useful regulatory elements, described previously or known in the art, can also be included in the nucleic acid constructs used to transfect mammalian cells. The transfection protocol chosen and the elements selected for use therein will depend on the type of host cell used. Those of skill in the art are aware of numerous different protocols and host cells, and can select an appropriate system for expression of a desired protein, based on the requirements of the cell culture system used.

Other features of the invention will become apparent in the course of the following descriptions of exemplary embodiments which are given for illustration of the invention and are not intended to be limiting thereof.

EXAMPLES

The following examples are put forth so as to provide those of ordinary skill in the art how to make and use the methods and compositions described herein, and are not intended to limit the scope of what the inventors regard as their invention. Efforts have been made to ensure accuracy with respect to numbers used (e.g., amount, temperature, etc.) but some experimental error and deviation should be accounted for. Unless indicated otherwise, parts are parts by weight, molecular weight is average molecular weight, temperature is in degrees Centigrade, and pressure is at or near atmospheric.

Example 1

Generation of RGC9 and RGC16 Cell Lines

CHO K1 cells ($1 \times 10^7$) were infected with pantropic retrovirus produced with plasmid pTE252 (FIG. 1), having a lox p site in it, at an MOI of less than 1 to generate a stable pool of cells with mostly one retroviral insertion per cell. Cells in the stable pool that expressed a marker protein at a high level were selected and expanded. Selection rounds were conducted to identify cell populations capable of enhanced expression. Thirty-six clones were isolated and expanded into 36 cell lines. Clones exhibiting the highest recombination efficiency were identified and cloned, wherein the clones each contained at least one recombinase recognition site in an enhanced expression locus. Eight cell populations with the best recombination efficiency were selected, and reassessed for enhanced protein expression. Two cell populations were selected and designated RGC9 and RGC16. Southern blot analysis of the cell populations from the original 36 cell lines that corresponded to these two cell lines showed that a single copy of a reporter construct was integrated into the CHO cell genome at the same locus in the case of both cell populations, and the location of integration was determined to be at the triplet "act" at nucleotide position 6,471 to 6,473 of SEQ ID NO:5. At least one of these two cell lines were employed in experiments described below.

Example 2

Expression of FcFP1 Protein in Serum-free Production Medium

RGC38 cells were derived from RGC9 cells and were adapted to grow in suspension in a serum-free production medium. RGC38 cells were used as host cells for the expression of FcFP1 protein (Fc fusion protein-1). RGC38 cells were transfected in a ten-centimeter plate with a FcFP1 expression vector, pTE851 and a Cre plasmid, pRG858. The FcFP1 plasmid has, in 5' to 3' direction, a LoxP site, a SV40 late promoter, a hygromycin resistant gene, an IRES, an eGFP, a CMV MIE promoter, a gene encoding a FcFP1 protein, and a Lox511 site. Cells were cultured in F12 medium with 400 µg/ml hygromycin for two weeks after transfection. Cells expressing eGFP but not DsRed were isolated using flow cytometry and designated as RS421-1. Isolated cells were essentially isogenic, though derived from different founder cells. RS421-1 cells were expanded in suspension cultures in serum-free production medium. FcP1 protein in conditioned medium of 3-day old cultures was examined in SDS-PAGE with Coomassie blue staining. FcF1 protein in the conditioned medium was abundant and could be seen without purification.

Example 3

Regulated Expression of FcFP1 Protein in Serum-free Production Medium

RGC49 cells were derived from RGC16, were adapted to grow in serum-free production medium, and contained a stably integrated tetR-YFP expression plasmid, pcDNA6/TR.

The tetR protein allows regulation of transcription from promoters that comprise a tet operator sequence by tetracycline or doxycycline. RGC49 cells were co-transfected with pTE851 and pRG858. The transfected cells were selected with 400 µg/ml hygromycin for two weeks. Cells expressing eGFP but not YFP were isolated using flow cytometry and designated as RS569-1. RS569-1 cells were expanded in suspension cultures in serum-free production medium in the presence or absence of doxycycline. FcP1 protein in conditioned medium of 3-day old cultures was examined by SDS-PAGE and Coomassie blue staining. The RS569-1 cells expressed FcFP1 protein similarly to RS421-1 upon in the presence of 1 µg/ml doxycycline in the culture medium. Very little FcFP1 protein was detected from the RS569-1 cells in the absence of doxycycline.

Example 4

Dual Lox Cell Line Construction

RGC23 cells were derived from RGC16, were adapted to grow in Sigma CHO SSM serum-free medium (Saint Louis, Mo.), and carried DsRed. RGC23 cells were transfected with a Cre plasmid, pRG858 and a eGFP and FcFP2 protein expression vector, pTE357. The FcFP2 vector has, in 5' to 3' direction, a LoxP site, a SV40 late promoter, a hygromycin resistant gene, a CMV MIE promoter, a gene encoding FcFP2 protein, an IRES, an eGFP, and a Lox511 site. Cells expressing both DsRed and eGFP were collected and a single cell was isolated. The isolated cell was expanded in culture, and the resulting cell line was designated RS398-2-6. RS398-2-6 was then transfected with pRG858 (Cre plasmid) and pRG1231, a eCFP expression plasmid. pRG1231 has, in 5' to 3' direction, a LoxP site, a CMV MIE promoter, a puromycin resistant gene, an IRES, an eCFP, and a Lox511 site. Cells expressing DsRed and eCFP but not eGFP were isolated by flow cytometry as a pool and designated as RS630.

Example 5

Antibody Heavy Chain and Light Chain Expression Using a Dual Lox Cell Line

RS630 cells were transfected with pTE828, a 15G1 antibody heavy chain and eGFP expression vector, pTE829, a 15G1 antibody light chain and eYFP expression vector, and pRG858. pTE828 has, in 5' to 3' direction, a LoxP site, a SV40 late promoter, a hygromycin resistant gene, an IRES, an eGFP, a CMV MIE promoter, the heavy chain gene of 15G1 antibody, and a Lox511 site. pTE829 has, in 5' to 3' direction, a LoxP site, a SV40 late promoter, a neomycin resistant gene, an IRES, an eYFP, a CMV MIE promoter, the light chain gene of 15G1 antibody, and a Lox511 site. The transfected cultures were selected with hygromycin and G418 at 400 µg/ml each for two weeks. Cells expressed both YFP and eGFP but neither dsRed nor eCFP were isolated by flow cytometry. The isolated cells were expanded in suspension culture in serum-free production medium and were designated as RS631 cells. Aliquots of conditioned medium from 3-day old culture were analyzed by SDS-PAGE. The antibody products from RS631 cells were readily detected by Coomassie blue staining.

Example 6

Use of a Third Lox Site (Lox2272) at EESYR to Create Dual Expression Cassette

Cells from any cell line carrying a DsRED gene flanked by a LoxP site and a Lox511 site at EESYR locus are transfected with pRG858 and a vector comprising, in 5' to 3' direction, a LoxP site, a first promoter, a YFP, a Lox2272 site, a second promoter, an eGFP, and a Lox511. Cells expressing eGFP and YFP, but not DsRed are isolated. Isolated cells are then transfected with pRG858, pRG1167 (a vector that has, in 5' to 3' direction, a LoxP site, a SV40 late promoter, a hygromycin resistant gene, a CMV MIE promoter, a DsRed and a Lox2272 site) or pRG1234 (a vector that has, in 5' to 3' direction, a Lox2272 site, a SV40 late promoter, a hygromycin resistant gene, a CMV MIE promoter, a DsRed and a Lox511 site). Cells capable of expressing either DsRED and eGFP but not YFP, or DsRED and YFP but not eGFP, are isolated.

Example 7

Antibody Expression from RGC38 Host Cells

RGC38 cells were transfected with pTE963 and pRG858. pTE963 has, in 5' to 3' direction, a LoxP site, a SV40 late promoter, a hygromycin resistant gene, an IRES, an eGFP, a CMV MIE promoter, the light chain gene of 15G1 antibody, a CMV MIE promoter, the heavy chain gene of 15G1 antibody, and a Lox511 site. The transfected cultures were selected with hygromycin at 400 µg/ml each for two weeks. Cells that expressed eGFP but not dsRed were isolated by flow cytometry. The isolated cells were expanded in suspension in serum-free production medium and were named as RS533 cells. For the production of 15G1 antibodies, RS533 cells were cultured in a bioreactor for 10 days. Aliquots of spent medium from day six to day ten were collected and their protein composition was analyzed by SDS-PAGE. The heavy chain and light chain peptide of the 15G1 antibody in the reactor spent medium were readily detected by Coomassie blue staining.

Example 8

Rescuing and Subcloning EESYR Sequences

A CHO cell line (designated RGC21) expressing high levels of a reporter gene, DsRed, was selected for isolation of EESYR sequences, since Southern blot analysis indicated that the high expression of DsRed expression observed for this cell line is driven by a single integration of an expression cassette encoding DsRed. Genomic sequences 5' to the expression cassette were rescued by transfecting RGC21 cells with linearized pTE494 plasmids, a vector that has, in 5' to 3' direction, a LoxP site, an ampicillin resistance gene, a bacterial origin of replication, a CMV MIE promoter, a neomycin phosphotransferase gene, an IRES, an eGFP and a Lox511 site. Cells expressing eGFP but not DsRed were isolated by flow cytometry as a pool. Genomic DNA was isolated, digested with XbaI restriction endonuclease, and self ligated to create pRG1106. Genomic sequences 3' to the expression cassette were rescued by transfecting RGC21 cells with circular pTE495 plasmids, a vector that has, in 5' to 3' direction, a LoxP site, a CMV MIE promoter, a neomycin phosphotransferase gene, an IRES, an eGFP, a bacterial origin of replication, an ampicillin resistance gene, and a Lox511 site. Cells expressing eGFP but not DsRed were isolated by flow cytometry as a pool. Genomic DNA was isolated, digested with MfeI restriction endonuclease, and self ligated to create pRG1099.

Example 9

Plasmid Construction for EESYR Analysis

EESYR sequences were excised from either pRG1106 or pRG1099 as AgeI fragments and inserted into the AgeI and NgoMIV sites of pTE575, a plasmid expressing FCFP2, to yield plasmid pTE809. The pTE575 plasmid has, in 5' to 3' direction, a SV40 late promoter, a hygromycin resistant gene, a CMV MIE promoter, and a gene encoding FCFP2 protein. In stably transfected CHO cells, pTE809 and pTE575 yielded 97.22% and 38.57% of cells expressing detectable levels of FCFP2 protein, respectively. The mean fluorescence of FcFP2 detected by an FITC conjugated antibody was 482.54 and 279.75 for cultures transfected with pTE809 and pTE575, respectively. Thus, the inclusion of EESYR in expression vectors increased the expression of FCFP2 protein in stable transfection.

The present invention may be embodied in other specific embodiments without departing from the spirit or essence thereof.

---

We claim:

1. An isolated cell comprising an expression-enhancing sequence comprising SEQ ID NO:5, a gene of interest (GOI) operably linked to the expression-enhancing sequence, and at least one recombinase recognition site immediately adjacent to the GOI.

2. The isolated cell of claim 1, wherein the GOI encodes a protein selected from an immunoglobulin or an antigen-binding fragment thereof, and a receptor or ligand-binding fragment thereof.

3. The isolated cell of claim 2, wherein the immunoglobulin is selected from an antibody light chain or antigen-binding fragment thereof, an antibody heavy chain or antigen-binding fragment thereof, or an Fc fusion protein.

4. The isolated cell of claim 1, wherein the at least one recombinase recognition site is selected from the group consisting of a LoxP site, a Lox511 site, a Lox2272, and a Frt site.

5. The isolated cell of claim 1, wherein the GOI is immediately adjacent and 5' of the recombinase recognition site, and further comprising a second recombinase recognition site immediately adjacent and 3' of the GOI.

6. The isolated cell of claim 5, further comprising a second GOI immediately adjacent and 3' of the second recombinase recognition site.

7. The isolated cell of claim 6, further comprising a third recombinase recognition site immediately adjacent and 3' of the second GOI.

8. The isolated cell of claim 7, further comprising at least one marker gene between the second recombinase recognition site and the second GOI.

9. The isolated cell of claim 8, wherein the at least one marker gene is selected from the group consisting of a drug resistance gene and an expression reporter gene.

10. The isolated cell of claim 9, further comprising a promoter operably linked to the first GOI and a promoter operably linked to the second GOI.

11. The isolated cell of claim 10, wherein the second and the third recombinase recognition sites are in an orientation opposite to the first recombinase recognition site.

12. The isolated cell of claim 11, wherein the first, second, and third recombinase recognition sites are different.

13. The isolated cell of claim 12, wherein the promoters are eukaryotic promoters, and the eukaryotic promoters are operably linked to a prokaryotic operator.

14. An isolated cell comprising an expression-enhancing sequence comprising SEQ ID NO:5, and at least one exogenous gene of interest (GOI) operably linked to the expression-enhancing sequence.

15. The isolated cell of claim 14, wherein the cell is a CHO cell, the at least one exogenous GOI is a human gene, and the human gene is operably linked to an exogenous promoter.

16. The isolated cell of claim 15, wherein the exogenous GOI and promoter are integrated at the triplet a-c-t at nucleotide position 6,471 to 6,473 of SEQ ID NO:5.

17. A method for making a protein of interest, comprising: (a) introducing into a host cell a nucleic acid construct comprising an expression-enhancing sequence comprising SEQ ID NO:5 and an exogenous gene of interest (GOI) that encodes for a protein of interest, wherein the GOI is operably linked to the expression-enhancing sequence; (b) culturing the host cell of (a) under conditions that allow expression of the GOI; and, (c) recovering the protein of interest.

18. The method of claim 17, wherein the GOI is operably linked to a promoter and integrated at the triplet a-c-t at nucleotide position 6,471 to 6,473 of SEQ ID NO:5.

19. The method of claim 18, wherein the cell is a CHO cell and the GOI is an immunoglobulin or an antigen-binding fragment thereof.

20. The method of claim 18, wherein the cell is a CHO cell and the GOI is a receptor or a ligand-binding fragment thereof.

* * * * *

SEQUENCE LISTING

<160> NUMBER OF SEQ ID NOS: 20

<210> SEQ ID NO 1
<211> LENGTH: 6473
<212> TYPE: DNA
<213> ORGANISM: Cricetulus griseus

<400> SEQUENCE: 1

```
tctagaaaca aaaccaaaaa tattaagtca ggcttggctt caggtgctgg ggtggagtgc      60
tgacaaaaat acacaaattc ctggctttct aaggcttttt cggggattca ggtattgggt     120
gatggtagaa taaaaatctg aaacataggt gatgtatctg ccatactgca tgggtgtgta     180
tgtgtgtgta tgtgtgtctg tgtgtgtgcc cagacagaaa taccatgaag gaaaaaaaca     240
cttcaaagac aggagagaag agtgacctgg gaaggactcc ccaatgagat gagaactgag     300
cacatgccag aggaggtgag gactgaacca ttcaacacaa gtggtgaata gtcctgcaga     360
cacagagagg gccagaagca ctcagaactc caggggggtca ggagtggttc tctggaggct     420
tctgcccttg gaggttcctg aggaggaggc ttccatattg aaaatgtagt tagtggccgt     480
ttccattagt acagtgacta gagagagctg agggaccact ggactgaggc ctagatgctc     540
agtcagatgg ccatgaaagc ctagacaagc acttccgggt ggaaaggaaa cagcaggtgt     600
gaggggtcag gggcaagtta gtgggagagg tcttccagat gaagtagcag gaacggagac     660
gcactggatg gccccacttg tcaaccagca aaagcttgga tcttgttcta agaggccagg     720
gacatgacaa gggtgatctc ggtttttaaa aggctttgtg ttacctaatc acttctatta     780
gtcagatact ttgtaacaca aatgagtact tggcctgtat tttagaaact tctgggatcc     840
tgaaaaaaca caatgacatt ctggctgcaa cacctggaga ctcccagcca ggccctggac     900
ccgggtccat tcatgcaaat actcagggac agattcttca ctaggtactg atgagctgtc     960
ttggatgcaa atgtggcctc ttcatttttac tacaagtcac catgagtcag gaggtgctgt    1020
ttgcacagtg tgactaagtg atggagtgtt gactgcagcc attcccggcc ccagcttgtg    1080
agagagatcc ttttaaattg aaagtaagct caaagttacc acgaagccac acatgtataa    1140
actgtgtgaa taatctgtgc acatacacaa accatgtgaa taatctgtgt acatgtataa    1200
actgtgtgaa taatctgtgt gcagcctttc cttacctact accttccagt gatcaggttt    1260
ggactgcctg tgtgctactg gaccctgaat gtccccaccg ctgtccctg tcttttacga    1320 ttctgacatt tttaataaat tcagcggctt cccctctgct ctgtgcctag ctataccttg    1380
gtactctgca ttttggtttc tgtgacattt ctctgtgact ctgctacatt ctcagatgac    1440
atgtgacaca gaaggtgttc cctctggaga catgtgatgt ccctgtcatt agtggaatca    1500
gatgccccca aactgttgtc cagtgtttgg gaaagtgaca cgtgaaggag gatcaggaaa    1560
```

```
agaggggtgg aaatcaagat gtgtctgagt atctcatgtc cctgagtggt ccaggctgct    1620
gacttcactc ccccaagtga gggaggccat ggtgagtaca cacacctcac acatactata    1680
tccaacacac acacacacac acacacacac acgcacgcac gcacgcacgc acgcacacat    1740
gcacacacac gaactacatt tcacaaacca catacgcata ttacaccccca aacgtatcac    1800 ctatacatac cacacataca caccccctcca cacatcacac acataccaca cccacacaca    1860
gcacacacat acataggcac acattcacac accacacata tacatttgtg tatgcataca    1920
tgcatacaca cacaggcaca cagacaccac acacatgcat tgtgtacgca cacatgcata    1980
cacacacata ggcacacatt gagcacacac atacatttgt gtacgcacac tacatagaca    2040
tatatgcatt tgtatatgca cacatgcatg cacacataca taggcacaca tagagcacac    2100
acatacattt gtgtatgcac acatgcacac accaatcaca tgggaagact caggttcttc    2160
actaaggttc acatgaactt agcagttcct ggttatctcg tgaaacttgg aagattgctg    2220
tggagaagag gaagcgttgg cttgagccct ggcagcaatt aaccccgccc agaagaagta    2280
ggtttaaaaa tgagagggtc tcaatgtgga acccgcaggg cgccagttca gagaagagac    2340
ctacccaagc caactgagag caaaggcaga gggatgaacc tgggatgtag tttgaacctc    2400
tgtaccagct gggcttcatg ctattttgtt atatctttat taaatattct tttagtttta    2460
tgtgcgtgaa taccttgctt gcataaatgt atgggcactg tatgtgttct tggtgccggt    2520
ggaggccagg agagggcatg gatcctccgg agctggcgtt tgagacagtt gtgacccaca    2580
gtgtggggtc tgggaactgg gtcttagtgt tccgcaagtg cagctggggc tcttaacctc    2640
tgagccatcc ctccagcttc aagaaactta ttttcttagg acatggggga agggatccag    2700
ggctttaggc ttgtttgttc agcaaatact cttttcgtgt attttgaatt ttatttatt    2760 ttacttttt gggatagaat cacattctgc agctcaggct gggcctgaac tcatcaaaat    2820
cctcctgtct cagtctacca ggtgataaga ttactgatgt gagcctggct ttgacaagca    2880
ctttagagtc cccagccctt ctggacactt gttccaagta taatatatat atatatatat    2940
atatatatat atatatatat atatattgtg tgtgtgtgtt tgtgtgtgta tgagacactt    3000
gctctaaggg tatcatatat atccttgatt tgcttttaat ttattttta attaaaaatg    3060 attagctaca tgtcacctgt atgcgtctgt atcatctata tatccttcct tccttctctc    3120
tctttctctc ttcttcttct caccccccaag catctatttt caaatccttg tgccgaggag    3180
atgccaagag tctcgttggg ggagatggtg agggggcgat acaggggaag agcaggagga    3240 aaggggggaca gactggtgtg ggtctttgga gagctcagga gaatagcagc gatcttccct    3300
gtccctggtg tcacctctta cagccaacac cattttgtgg cctggcagaa gagttgtcaa    3360
gctggtcgca ggtctgccac acaacccccaa tctggcccca agaaaaggca cctgtgtgtg    3420
actctggggt taaaggcgct gcctggtcgt ctccagctgg acttgaaact cccgttaat    3480 aaagagttct gcaaaataat acccgcagag tcacagtgcc aggttcccgt gctttcctga    3540
agcgccaggc acgggttccc taggaaatgg ggccttgctt gccaagctcc cacggcttgc    3600
cctgcaaacg gcctgaatga tctggcactc tgcgttgcca ctgggatgaa atggaaaaaa    3660
gaaaaagaag aagtgtctct ggaagcgggc gcgctcacac aaacccgcaa cgattgtgta    3720
aacactctcc attgagaatc tggagtgcgg ttgccctcta ctggggagct gaagacagct    3780
agtgggggcg gggggaggac cgtgctagca tccttccacg gtgctcgctg gctgtggtgc    3840
atgccgggaa ccgaaacgcg gaactaaagt caagtcttgc tttggtggaa ctgacaatca    3900
acgaaatcac ttcgattgtt ttcctctttt tactggaatt cttggatttg atagatgggg    3960
```

```
gaggatcaga gggggagggg aggggcgggg agacggaggg aggaggggag gaggggagga    4020
ggggaggagg ggaggagggg aagggatgga ggaaaatact aacttttcta attcaacatg    4080
acaaagattc ggagaaagtg caccgctagt gaccgggagg aggaatgccc tattgggcat    4140
tatattccct gtcgtctaat ggaatcaaac tcttggttcc agcaccaagg attctgagcc    4200
tatcctattc aagacagtaa ctacagccca cacggaagag gctatacaac tgaagaaata    4260
aaattttcac tttatttcat ttctgtgact gcatgttcac atgtagagag ccacctgtgt    4320
ctagggctg atgtgctggg cagtagagtt ctgagcccgt taactggaac aacccagaac     4380
tcccaccaca gttagagctt gctgagagag ggaggccctt ggtgagattt ctttgtgtat    4440
ttatttagag acagggtctc atactgtagt ccaagctagc ctccagctca cagaaattct    4500
cctgttccgg tttccaaagt actggagtta tgagtgtgtg ttaattgaac gctaagaatt    4560
tgctgattga agaaaacctc aagtgggttt ggctaatccc cacgacccca gaggctgagg    4620
caggaggaat gagagaattc aaggtttgcc agagccacag ggtgagctca atgtggagac    4680
tgtgagggtg agctcaatgt ggagactgtg agggtgagct caatgtggag actgtgaggg    4740
tgagctcaat gtggagactg tgaggtgag ctcaatgtgg agactgtgag ggtgagctca     4800
atgtggagac ctgtatcaag ataataatag tagtagtaac aatgcaggcg agggtgtggt    4860
tgagtggtag agcagttagt tgatttgaca tgcttgaggt ctcccggtcc atctgtggcc    4920
ctgcaacagg aagggaggga ggaagggggg gaacgagaga gaggaaagag agacagaagc    4980
taagataggg aatgagagag gaaggaagaa acgggaagaa attcagactc cttcctgagt    5040
tccgccaacg cctagtgaca tcctgtgcac accctaaggt ggcctttgtg tggcactggc    5100
ttgggtggtc gggaaaggca ttttcagctt gttgcagaac tgccacagta gcatgctggg    5160
tccgtgaaag tttctgcccg ttaacaagaa gtctctacta cttgtgacct caccagtgaa    5220
aatttcttta attgtctcct ggtgttctgg gttttgcatt tttgtttcta aggatacatt    5280
cctgggtgat gtcatgaagt ccccaaagac acagtgggc tgtgttggat tgggaaagat     5340
gatttatctg gggtgtcaaa aggaaaagaa gggaaacagg cacttgggaa aatgtcctcc    5400
cgcccacccg aattttggct tggcaaccgt ggtggaggag caagaaacac gtggacgttt    5460
gaggaggcat ggggtcctag gaggacagga agcagaagga gagagctggg ctgacagcct    5520
gcaggcattg cacagtttca gaaggagatt acagcatgac tgagtttta gggatccaac     5580
agggacctgg gtagagattc tgtgggctct gaggcaactt gacctcagcc agatggtatt    5640
tgaataacct gctcttagag ggaaaacaga catagcaaac agagccacgt ttagtgatga    5700
aactctcact ttgcctgagt catgtgcggc catgcccagg ggtcaggctg acactcaact    5760
caaaaacaag tgagaaattg aagacaatcc gtggtggcag ctactggaag ggccaccaca    5820
tccccagaaa gagtggagct gctaaaaagc catttgtgat aggcacagtt atcttgaatg    5880
catggagcag agattacgga aaaatcgaga atgttaatga ggcaacattc gagttgagtc    5940
attcagtgtg ggaaacccag acgcttccat ccctaaaag gaacatcttg ctctcagtca     6000
aaatggaaat aaaaattggg gcttgaattt ggcaaatgat tcagaactct gtgtaggtat    6060
tttcacacgc acagtggata attttcatgt tggagtttat ttgtgctaaa aggcagaaaa    6120
gggtaaaaag cacatcttaa gagttatgag gttctacgaa taaaataat gttacttaca     6180
gctattcctt aattagtacc cccttccacc tgtggtaatt tcctgagata gtcagtgggg    6240
aaaagatctc tccttctctt ctttctcccc ctccctcct ctccctccct ccctccctcc     6300
ctccctcctc tccctccctc cccctttcct tctttctttg ctccttctcc tctgcctcct    6360
```

```
tctcccttc  ttcttcattt  attctaagta  gcttttaaca  gcacaccaat  tacctgtgta      6420
taacgggaaa  acacaggctc  aagcagctta  gagaagattg  atctgtgttc  act            6473

<210> SEQ ID NO 2
<211> LENGTH: 7045
<212> TYPE: DNA
<213> ORGANISM: Cricetulus griseus

<400> SEQUENCE: 2
actagcgtgc  aattcagagg  tgggtgaaga  taaaaggcaa  acatttgagg  ccatttcctt       60
atttggcacg  gcacttagga  agtggaacat  gcctaatcta  ctggtttgta  ccacctttcc      120
ctataatgga  ctgtttggga  agctcctggg  caaccgattc  tggcatctca  ttggtcagag      180
gcctgttaaa  tggtactctt  atttgcaaag  aaggctgtaa  cttgtagctt  taaaagcctc      240
tcctcaagaa  agaagggaga  aaggatatgg  ctagacatat  ctaatagact  taaccactgt      300
gaaaagcctt  agtatgaatc  agatagaacc  tattttaac  tcagttttga  aaaaaataat       360
ctttatattt  atttgtgtgt  gtgtgtgtgt  gtgtgtgtgt  gtgtgtgtgt  gtgtgtgtgt      420
gaaccacatg  tagcaggtgc  tggaggaggc  cagaagaggg  caccagatct  cctggaactg      480
acaccacaca  tggttatgag  ctgcctgatg  tgggtgctgg  gaactgaact  ctcgtgttct      540
gcaagagcag  caactgttct  cttaactgat  gagccatctc  tccagccccc  cccataattt      600
taattgttca  ttttagtaaa  ttttattcat  aatcaattat  cacagtataa  aacaatgatt      660
ttatatatat  catatacata  tcaaggatga  cagtgagggg  gatatgtgtg  tgtgtgtgtg      720
tgtgtgtgtg  tgtgtgtgtg  tgtgttattt  gtgtgtgtgc  tttttaagaa  ggtgccatag      780
tcactgcatt  tctctgaagg  atttcaaagg  aatgagacat  gtctgtctgc  caggaaccct      840
atcttcctct  ttgggaatct  gacccaaatg  aggtattctg  aggaactgaa  tgaagagctc      900
aagtagcagt  gtcttaaacc  caaatgtgct  gtctagagaa  agtcaacgtc  atcagtgagc      960
tgaggagaga  tttactgagc  ggaagacaag  cgctctttga  tttaagtggc  tcgaacagtc     1020
acggctgtgg  agtggagcct  gtgctcaggt  ctgaggcagt  ctttgctagc  cagctgtgat     1080
gagcagtgaa  gaaagggtgg  agatggaggc  agggtgggag  cagggctatg  gttcagacta     1140
ggtatcgtga  gcacaccagc  tggttgactt  gtggtctgtg  ggtcaggcgt  tgtaaacgcc     1200
ctcagggtca  ggcagtcaca  ttgcttgaag  ctgaatgggt  gaggcaacac  agagagtgca     1260
aagaaggcaa  agtaccacct  cttccccgac  ccaggtcact  tctgggttat  agctgagact     1320
ccggacagca  tgcaaccagc  tggttagagc  ttcaggaaa   acttgatgtc  tgcatgttgc     1380
tatgaaatgt  gattcggtac  atctggagaa  aatttataat  gctggctcag  tcaagcactg     1440
aacaaaggta  ccttggcttt  gggagctaca  tgacattgac  ttgtaggcag  acttttttt      1500 ttctgcccgc  caattcccag  ataaccaata  tggaggctca  atattaatta  taaatgctcg     1560
gctgatagct  caggcttgtt  actagctaac  tcttccaact  taaatgaacc  catttctatt     1620
atctacattc  tgccacgtga  ctttaccttg  tacttcctgt  ttcctctcct  tgtctgactc     1680
tgcccttctg  cttcccagag  tccttagtct  ggttctcctg  cctaacctta  tcctgcccag     1740
ctgctgacca  agcatttata  attaatatta  agtctcccag  tgagactctc  atccagggag     1800 gacttggggtg  ctccccctc   ctcattgcca  tccgtgtctt  cctcttccct  cgcttccccc     1860
tcctcttcct  gctcttcctc  ctccacccct  cctttcatag  tattgatggc  aagggtgttc     1920
tagaatggag  gagtgcccat  aggcatgcaa  agaaaccagt  taggatgctc  tgtgagggga     1980
tgtaatcata  agcgatggac  acaattcaag  ccacagagtg  aagacggaag  gatgcactgt     2040
```

```
gctctagagc aacttctggg gcagaatcac agggtgagtt tctgacttga gggcgaagag    2100
gccacgagga agggagtgag tttgtctgag ctagaagcta cggcccacct cttggtagca    2160
gacctgccca caagcatgct tgttaatca tgtgggatct gattttcctc taaatctatg     2220
ttcaactctt aagaaaatgt gaattctcac attaaaattt agatatacgt cttttggtgg    2280 gggggggtgta aaaatccctc aagaatatgg atttctgggg gccggagaga tggctcagag    2340
gttaagagaa ctggttgctc ttctagacat tctgagttca attcccagca accacatggt    2400
ggctcacaac catctgtaat gcgacctggt gccatcttct gacatgcatg gatacatgca    2460
ggcagaaagc tgtatacata gtaaattgat aaatcttttt ttaaaaagag tatggattct    2520
gccgggtgtt ggtggcgcac gcctttaatc ccagcactct ggaggcagag gcaggtggat    2580
ctctgtgagt tcgagaccag cctggtctat aagagctagt tccaggacag cctccaaagc    2640
cacagagaaa ccctgtctcg aaaaaccaaa aaaaaaaaaa aaaaaaaaaa aaaaaaaga     2700 gtatggattc taagaaagcc gtaacagctg gagctgtgta cggagttcag cgtggtacta    2760
gaagaacaga cattcatgat gaaacaccccc aggattttta cttagtatct agtttccatt   2820
gttgttttga gaccggctct tatgctctcc aggctggcct caaactgctg atcttcccgc    2880
ctctacctct caagtcctgg gactacttgg ctcataaaac agttttttgtc gggctccctg   2940 aagttatggt tgtacaaacc gtgggggtca atatactcac ttgggcagag agagaaggtc    3000
tgaatcccag acaatgactg catctcagga cagttgggaa gaggacaatg gcagaaggac    3060
ttagaaaaga tagactggag ggtggaaaag cagcaggaac agagaaacaa acaggaagc    3120 ttgctatcca gggccactct ggagtcctgt ggcaagatgg aagcgggcta ggggaataca    3180
tttgtgctac tgtgtgtgtg tgtgtgtgtg tgtgtgtgtg tgtgtgtgat caatgcctat    3240
caatgttgaa ggggaaatat gtataccaca ttgattctgg gagcaattct cagtatctgg    3300
cctagagaaa ggaatggccc ctgcagaata gacagagtga atggtgccct ttatcatttg    3360
ctaaagtgaa ggagaaataa acatccttcc atagagtttc aggtaaatga accccacagt    3420
tcatctgtgc cgtggtggag gcctggccaa cagttaaaaa gattagacac ggacaaagtc    3480
tgaaggaaac acctcgaata ggaagaggag agccacctca ttctgtaact ttcctcaagg    3540
ggaagatgtt ccaagagtgg gaataaatgg tcaagggggg gatttttaat taggaaaacg    3600
atttcctgta tcacttgtga aactggaggt tgatttgggg cataggacaa tagatttgat    3660
gctttgcaaa aagctgtttc aaagcagaga aatggaatag agacaattat gtagcgagga    3720
gggagggtgg ggcgaagatg gagacagaga agtggaagct gactttaggg aagaggaaca    3780
tagaccacag gggcggggcg ggggcaggg gcggggggcg gggctcaaag gaggcagtgg      3840
gaacgttgct agtgttcgca gcgtaagcgt gaatgtgcaa gcgtcttttg ggtgtgtgac    3900
caggagtagc gtggctggct tgtgtgctgc ttgtaatccc agtctttgag gtttccacac    3960
tgttccacag tgggtgtgat ttccctcgg agagcatgag ggctctgctt tccccacatc     4020
ctccccagcg ttcgttggta tttgtttcca agatgttagt gggtgagaca agcctctct     4080 gttgatttgc ctttaacagg tgacaaaaaa agctcaacca ggagacattt ttgccttctt    4140
ggaaggtaat gctcccatgt agagcaatgg gacccatctc taaggtgagg ctactcttgc    4200
agtttgcacc cagctcttct gatgcaggaa ggaagttggt gggcaagcaa gactgtttgc    4260 ttccttgcgat ggacacattc tgcacacaaa ggctcaggag gggagaaggc tgtttgatgt   4320
ttagcactca ggaaggcccc tgatgcatct gtgattagct gtctccatct gtggagcaga    4380
cacggactaa ctaaaaacca gtgttttttaa attgtcaagc ctttaaggtg aggaaattga    4440
```

```
cttattgtgc tgggccatac gtagagcaag tgctctgcat tgggccaacc cccggctctg    4500
gtttctaggc accagaatgg cctagaacta actcacaatc ctcccattcc aggtctcagg    4560
tgctagaatg aaccactata ccagcctgcc tgcctgccta cctgccttcc taaattttaa    4620
atcatgggga gtaggggaga atacacttat cttagttagg gtttctattg ctgtgaagag    4680
acaccatgag catggcaact cttataaagg aaaacattta gttgggtggc agtttcagag    4740
gttttagtac attgtcatca tggctgggaa catgatggca tgcagacaga catggtgctg    4800
gagaaaggga tgagagtcct acatcttgca ggcaacagga cctcagctga gacactggct    4860
ggtaccctga gcataggaaa cctcacagcc caccctcaca gtgacatatt tccttcaaca    4920
aagccatacc tcctaatagt gccactccct atgagatgac agggccaatt acattcaaac    4980
tgctataaca ctttaaagta tttattttt attattgtaa attatgtatg tagctgggtg    5040
gtggcagccg aggtgcacgc ctttaatccc agcacttggg aggcagaggc agatggatct    5100
ctgtgagttc aagaccagcc tggtctataa gagctagttg caaggaagga tatacaaaga    5160
acagttctag gatagccttc aaagccacag agaagtgctg tcttgaaaac caaaaattgt    5220
gctgggacct gtctctgctt tggttgcttc ccactccccc agagctggac tcttggtcaa    5280
cactgaatca gctgcaaaat aaactcctgg attcctctct tgtaacagga gcccgaagtc    5340
aggcgcccac ttgtcttctc gcaggattgc catagactt tctgtgtgc ccaccattcc    5400 agactgaagt agagatggca gtggcagaga ctgggaaggc tgcaacgaaa acaggaagtt    5460
attgcaccct gggaatagtc tggaaatgaa gcttcaaaac ttgcttcatg ttcagttgta    5520
cacagactca ctcccaggtt gactcacacg tgtaaatatt cctgactatg tctgcactgc    5580
ttttatctga tgcttccttc ccaaaatgcc aagtgtacaa ggtgagggaa tcacccttgg    5640
attcagagcc cagggtcgtc ctccttaacc tggacttgtc tttctccggc agcctctgac    5700
accccctccc ccattttctc tatcagaagg tctgagcaga gttggggcac gctcatgtcc    5760
tgatacactc cttgtcttcc tgaagatcta acttctgacc cagaaagatg gctaaggtgg    5820
tgaagtgttt gacatgaaga cttggtctta agaactggag caggggaaaa aagtcggatg    5880
tggcagcatg tacccgaaat cccagaactg ggaggtaga gacggatgag tgcccggggc    5940
tagctggctg ctcagccagc ctagctgaat tgccaaattc caactcctat tgaaaaacct    6000
ttaccaaaca aacaaacaaa caataataa caacaacaac aacaacaaac taccccatac    6060
aaggtgggcg gctcttggct cttgaggaat gactcaccca aacccaaagc ttgccacagc    6120
tgttctctgg cctaaatggg gtggggtgg ggcagagaca gagacagaga gagacatgac    6180
ttcctgggct gggctgtgtg ctctaggcca ccaggaactt tcctgtcttg ctctctgtct    6240
ggcacagcca gagcaccagc acccagcagg tgcacacacc tccctccgtg cttcttgagc    6300
aaacacaggt gccttggtct gtctattgaa ccggagtaag ttcttgcaga tgtatgcatg    6360
gaaacaacat tgtcctggtt ttatttctac tgttgtgata aaaaccgggg aactccagga    6420
agcagctgag gcagaggcaa atgcaaggaa tgctgcctcc tagcttgctc cccatggctt    6480
gccgggcctg ctttctgcaa gcccttctct ccccattggc atgcctgaca tgaacagcgt    6540
ttgaaatgct ctcaaatgtc actttcaaag aaggcttctc tgatcttgct aactaaatca    6600
gaccatgttt caccgtgcat tatctttctg ctgtctgtct gtctgtctgt ctgtctatct    6660
gtctatcatc tatcaatcat ctatctatct atcttctatt tatctaccta tcattcaatc    6720
atctatcttc taactagtta tcattatttt atttgtttac ttacttttttt tatttgagac    6780 agtatttctc tgagtgacag ccttggctgt cctggaaccc attctgtaac caggctgtcc    6840
```

```
tcaaactcac agagatccaa ctgcctctgc ctctctggtg ctggggttaa agacgtgcac    6900
caccaacgcc ccgctctatc atctatttat gtacttatta ttcagtcatt atctatcctc    6960
taactatcca tcatctgtct atccatcatc tatctatcta tctatctatc tatctatcta    7020
tctatcatcc atctataatc aattg                                          7045

<210> SEQ ID NO 3
<211> LENGTH: 6473
<212> TYPE: DNA
<213> ORGANISM: Cricetulus griseus

<400> SEQUENCE: 3
agtgaacaca gatcaatctt ctctaagctg cttgagcctg tgttttcccg ttatacacag      60
gtaattggtg tgctgttaaa agctacttag aataaatgaa gaagaaaggg agaaggaggc     120
agaggagaag gagcaaagaa agaaggaaag ggggagggag ggagaggagg gagggaggga     180
gggagggagg gagaggaggg gaggggagga aagaagagaa ggagagatct tttcccact     240 gactatctca ggaaattacc acaggtggaa gggggtacta attaaggaat agctgtaagt     300
aacattattt ttattcgtag aacctcataa ctcttaagat gtgcttttta cccttttctg     360
ccttttagca caaataaact ccaacatgaa aattatccac tgtgcgtgtg aaaataccta     420
cacagagttc tgaatcattt gccaaattca agccccaatt tttatttcca tttttgactga    480 gagcaagatg ttccttttag gggatggaag cgtctgggtt tcccacactg aatgactcaa     540
ctcgaatgtt gcctcattaa cattctcgat ttttccgtaa tctctgctcc atgcattcaa     600
gataactgtg cctatcacaa atggcttttt agcagctcca ctctttctgg ggatgtggtg     660
gcccttccag tagctgccac cacggattgt cttcaatttc tcacttgttt ttgagttgag     720
tgtcagcctg accctgggc atggccgcac atgactcagg caaagtgaga gtttcatcac     780
taaacgtggc tctgttttgct atgtctgttt tccctctaag agcaggttat tcaaatacca     840
tctggctgag gtcaagttgc ctcagagccc acagaatctc tacccaggtc cctgttggat     900
ccctaaaaac tcagtcatgc tgtaatctcc ttctgaaact gtgcaatgcc tgcaggctgt     960
cagcccagct ctctccttct gcttcctgtc ctcctaggac cccatgcctc tcaaacgtc    1020 cacgtgtttc ttgctcctcc accacggttg ccaagccaaa attcgggtgg cgggaggac    1080 attttcccaa gtgcctgttt cccttctttt ccttttgaca ccccagataa atcatctttc    1140
ccaatccaac acagccccac tgtgtctttg gggacttcat gacatcaccc aggaatgtat    1200
ccttagaaac aaaaatgcaa aacccagaac accaggagaa aattaaagaa attttcactg    1260
gtgaggtcac aagtagtaga gacttcttgt taacgggcag aaactttcac ggacccagca    1320
tgctactgtg gcagttctgc aacaagctga aaatgccttt cccgaccacc caagccagtg    1380
ccacacaaag gccaccttag ggtgtgcaca ggatgtcact aggcgttggc ggaactcagg    1440
aaggagtctg aatttcttcc cgtttcttcc ttcctctctc attccctatc ttagcttctg    1500
tctctctttc ctctctctcg ttccccccct tcctccctcc cttcctgttg cagggccaca    1560
gatggaccgg gagacctcaa gcatgtcaaa tcaactaact gctctaccac tcaaccacac    1620
cctcgcctgc attgttacta ctactattat tatcttgata caggtctcca cattgagctc    1680
accctcacag tctccacatt gagctcaccc tcacagtctc cacattgagc tcaccctcac    1740
agtctccaca ttgagctcac cctcacagtc tccacattga gctcaccctc acagtctcca    1800
cattgagctc accctgtggc tctggcaaac cttgaattct ctcattcctc ctgcctcagc    1860
ctctggggtc gtggggatta gccaaaccca cttgaggttt tcttcaatca gcaaattctt    1920
```

```
agcgttcaat taacacacac tcataactcc agtactttgg aaaccggaac aggagaattt    1980
ctgtgagctg gaggctagct tggactacag tatgagaccc tgtctctaaa taaatacaca    2040
aagaaatctc accaagggcc tccctctctc agcaagctct aactgtggtg ggagttctgg    2100
gttgttccag ttaacgggct cagaactcta ctgcccagca catcagcccc tagacacagg    2160
tggctctcta catgtgaaca tgcagtcaca gaaatgaaat aaagtgaaaa ttttatttct    2220
tcagttgtat agcctcttcc gtgtgggctg tagttactgt cttgaatagg ataggctcag    2280
aatccttggt gctggaacca agagtttgat tccattagac gacagggaat ataatgccca    2340 ataggggcatt cctcctcccg gtcactagcg gtgcactttc tccgaatctt tgtcatgttg    2400
aattagaaaa gttagtattt tcctccatcc cttccctcc tccctcctc ccctcctccc    2460 ctcctccct cctccctccg tctccccgcc cctcccctcc ccctctgatc ctcccccatc    2520
tatcaaatcc aagaattcca gtaaaaagag gaaaacaatc gaagtgattt cgttgattgt    2580
cagttccacc aaagcaagac ttgactttag ttccgcgttt cggttcccgg catgcaccac    2640
agccagcgag caccgtggaa ggatgctagc acggtcctcc ccccgccccc actagctgtc    2700
ttcagctccc cagtagaggg caaccgcact ccagattctc aatggagagt gtttacacaa    2760
tcgttgcggg tttgtgtgag cgcgcccgct tccagagaca cttcttcttt ttcttttttc    2820
catttcatcc cagtggcaac gcagagtgcc agatcattca ggccgtttgc agggcaagcc    2880
gtgggagctt ggcaagcaag gccccatttc ctagggaacc cgtgcctggc gcttcaggaa    2940
agcacgggaa cctggcactg tgactctgcg ggtattattt tgcagaactc tttattaaac    3000
gggagtttca gtccagctg gagacgacca ggcagcgcct ttaaccccag agtcacacac    3060
aggtgccttt tcttggggcc agattggggt tgtgtggcag acctgcgacc agcttgacaa    3120
ctcttctgcc aggccacaaa atggtgttgg ctgtaagagg tgacaccagg gacagggaag    3180
atcgctgcta ttctcctgag ctctccaaag acccacacca gtctgtcccc ctttcctcct    3240
gctcttcccc tgtatcgccc cctcaccatc tcccccaacg agactcttgg catctcctcg    3300
gcacaaggat ttgaaaatag atgcttgggg gtgagaagaa gaagagagaa agagagagaa    3360
ggaaggaagg atatatagat gatacagacg catacaggtg acatgtagct aatcattttt    3420
aattaaaaaa taaattaaaa gcaaatcaag gatatatatg ataccccttag agcaagtgtc    3480 tcatacacac acaaacacac acacacaata tatatatata tatatatata tatatatata    3540
tatatatata ttatacttgg aacaagtgtc cagaagggct ggggactcta aagtgcttgt    3600
caaagccagc ctcacatcag taatcttatc acctggtaga ctgagacagg aggatttgta    3660
tgagttcagg cccagcctga gctgcagaat gtgattctat cccaaaaaag taaaataaaa    3720
taaaattcaa aatacacgaa aagagtattt gctgaacaaa caagcctaaa gccctggatc    3780 ccttcccca tgtcctaaga aaataagttt cttgaagctg gagggatggc tcagaggtta    3840 agagcccag ctgcacttgc ggaacactaa gacccagttc ccagaccca cactgtgggt    3900 cacaactgtc tcaaacgcca gctccggagg atccatgccc tctcctggcc tccaccggca    3960
ccaagaacac atacagtgcc catacattta tgcaagcaag gtattcacgc acataaaact    4020
aaaagaatat ttaataaaga tataacaaaa tagcatgaag cccagctggt acagaggttc    4080 aaactcatc ccaggttcat ccctctgcct ttgctctcag ttggcttggg taggtctctt    4140
ctctgaactg gcgccctgcg ggttccacat tgagaccctc tcattttaa acctacttct    4200 tctgggcggg gttaattgct gccagggctc aagccaacgc ttcctcttct ccacagcaat    4260
cttccaagtt tcacgagata accaggaact gctaagttca tgtgaacctt agtgaagaac    4320
```

-continued

| | |
|---|---|
| ctgagtcttc ccatgtgatt ggtgtgtgca tgtgtgcata cacaaatgta tgtgtgtgct | 4380 |
| ctatgtgtgc ctatgtatgt gtgcatgcat gtgtgcatat acaaatgcat atatgtctat | 4440 |
| gtagtgtgcg tacacaaatg tatgtgtgtg ctcaatgtgt gcctatgtgt gtgtatgcat | 4500 |
| gtgtgcgtac acaatgcatg tgtgtggtgt ctgtgtgcct gtgtgtgtat gcatgtatgc | 4560 |
| atacacaaat gtatatgtgt ggtgtgtgaa tgtgtgccta tgtatgtgtg tgctgtgtgt | 4620 |
| gggtgtggta tgtgtgtgat gtgtggaggg gtgtgtatgt gtggtatgta taggtgatac | 4680 |
| gtttggggtg taatatgcgt atgtggtttg tgaaatgtag ttcgtgtgtg tgcatgtgtg | 4740 |
| cgtgcgtgcg tgcgtgcgtg cgtgtgtgtg tgtgtgtgtg tgtgtgtgtt ggatatagta | 4800 |
| tgtgtgaggt gtgtgtactc accatggcct ccctcacttg ggggagtgaa gtcagcagcc | 4860 |
| tggaccactc agggacatga gatactcaga cacatcttga tttccacccc tcttttcctg | 4920 |
| atcctccttc acgtgtcact ttcccaaaca ctggacaaca gtttgggggc atctgattcc | 4980 |
| actaatgaca gggacatcac atgtctccag agggaacacc ttctgtgtca catgtcatct | 5040 |
| gagaatgtag cagagtcaca gagaaatgtc acagaaacca aaatgcagag taccaaggta | 5100 |
| tagctaggca cagagcagag gggaagccgc tgaatttatt aaaaatgtca gaatcgtaaa | 5160 |
| agacagggga cagcggtggg gacattcagg gtccagtagc acacaggcag tccaaacctg | 5220 |
| atcactggaa ggtagtaggt aaggaaaggc tgcacacaga ttattcacac agtttataca | 5280 |
| tgtacacaga ttattcacat ggtttgtgta tgtgcacaga ttattcacac agtttataca | 5340 |
| tgtgtggctt cgtggtaact ttgagcttac tttcaattta aaaggatctc tctcacaagc | 5400 |
| tggggccggg aatggctgca gtcaacactc catcacttag tcacactgtg caaacagcac | 5460 |
| ctcctgactc atggtgactt gtagtaaaat gaagaggcca catttgcatc caagacagct | 5520 |
| catcagtacc tagtgaagaa tctgtccctg agtatttgca tgaatggacc cgggtccagg | 5580 |
| gcctggctgg gagtctccag gtgttgcagc cagaatgtca ttgtgttttt tcaggatccc | 5640 |
| agaagtttct aaaatacagg ccaagtactc atttgtgtta caaagtatct gactaataga | 5700 |
| agtgattagg taacacaaag ccttttaaaa accgagatca cccttgtcat gtccctggcc | 5760 |
| tcttagaaca agatccaagc ttttgctggt tgacaagtgg ggccatccag tgcgtctccg | 5820 |
| ttcctgctac ttcatctgga agacctctcc cactaacttg cccctgaccc ctcacacctg | 5880 |
| ctgtttcctt tccacccgga agtgcttgtc taggctttca tggccatctg actgagcatc | 5940 |
| taggcctcag tccagtggtc cctcagctct ctctagtcac tgtactaatg gaaacggcca | 6000 |
| ctaactacat tttcaaatatg gaagcctcct cctcaggaac ctccaagggc agaagcctcc | 6060 |
| agagaaccac tcctgacccc ctggagttct gagtgcttct ggccctctct gtgtctgcag | 6120 |
| gactattcac cacttgtgtt gaatggttca gtcctcacct cctctggcat gtgctcagtt | 6180 |
| ctcatctcat tggggagtcc ttcccaggtc actcttctct cctgtctttg aagtgttttt | 6240 |
| ttccttcatg gtatttctgt ctgggcacac acacagacac acatacacac acatacacac | 6300 |
| ccatgcagta tggcagatac atcacctatg tttcagattt ttattctacc atcacccaat | 6360 |
| acctgaatcc ccgaaaaagc cttagaaagc caggaatttg tgtattttttg tcagcactcc | 6420 |
| accccagcac ctgaagccaa gcctgactta atattttttgg ttttgtttct aga | 6473 |

<210> SEQ ID NO 4
<211> LENGTH: 7045
<212> TYPE: DNA
<213> ORGANISM: Cricetulus griseus

<400> SEQUENCE: 4

-continued

| | |
|---|---|
| caattgatta tagatggatg atagatagat agatagatag atagatagat agatagatga | 60 |
| tggatagaca gatgatggat agttagagga tagataatga ctgaataata agtacataaa | 120 |
| tagatgatag agcggggcgt tggtggtgca cgtctttaac cccagcacca gagaggcaga | 180 |
| ggcagttgga tctctgtgag tttgaggaca gcctggttac agaatgggtt ccaggacagc | 240 |
| caaggctgtc actcagagaa atactgtctc aaataaaaaa agtaagtaaa caaataaata | 300 |
| aatgataact agttagaaga tagatgattg aatgataggt agataaatag aagatagata | 360 |
| gatagatgat tgatagatga tagacagata gacagacaga cagacagaca gacagcagaa | 420 |
| agataatgca cggtgaaaca tggtctgatt tagttagcaa gatcagagaa gccttctttg | 480 |
| aaagtgacat ttgagagcat ttcaaacgct gttcatgtca ggcatgccaa tggggagaga | 540 |
| agggcttgca gaaagcaggc ccggcaagcc atggggagca agctaggagg cagcattcct | 600 |
| tgcatttgcc tctgcctcag ctgcttcctg gagttccccg gttttttatca caacagtaga | 660 |
| aataaaacca ggacaatgtt gtttccatgc atacatctgc aagaacttac tccggttcaa | 720 |
| tagacagacc aaggcacctg tgtttgctca agaagcacgg agggaggtgt gtgcacctgc | 780 |
| tgggtgctgg tgctctggct gtgccagaca gagagcaaga caggaaagtt cctggtggcc | 840 |
| tagagcacac agcccagccc aggaagtcat gtctctctct gtctctgtct ctgccccacc | 900 |
| cccaccccat ttaggccaga gaacagctgt ggcaagcttt gggtttgggt gagtcattcc | 960 |
| tcaagagcca agagccgccc accttgtatg gggtagtttg ttgttgttgt tgttgttatt | 1020 |
| atttgtttgt ttgtttgttt ggtaaaggtt tttcaatagg agttggaatt tggcaattca | 1080 |
| gctaggctgg ctgagcagcc agctagcccc gggcactcat ccgtctctac ctccccagtt | 1140 |
| ctgggatttc gggtacatgc tgccacatcc gacttttttc ccctgctcca gttcttaaga | 1200 |
| ccaagtcttc atgtcaaaca cttcaccacc ttagccatct ttctgggtca gaagttagat | 1260 |
| cttcaggaag acaaggagtg tatcaggaca tgagcgtgcc ccaactctgc tcagaccttc | 1320 |
| tgatagagaa aatgggggga ggggtgtcag aggctgccgg agaaagacaa gtccaggtta | 1380 |
| aggaggacga ccctgggctc tgaatccaag ggtgattccc tcaccttgta cacttggcat | 1440 |
| tttgggaagg aagcatcaga taaaagcagt gcagacatag tcaggaatat ttacacgtgt | 1500 |
| gagtcaacct gggagtgagt ctgtgtacaa ctgaacatga agcaagtttt gaagcttcat | 1560 |
| ttccagacta ttcccagggt gcaataactt cctgttttcg ttgcagcctt cccagtctct | 1620 |
| gccactgcca tctctacttc agtctggaat ggtgggcaca cagaaaaagt ctatggcaat | 1680 |
| cctgcgagaa gacaagtggg cgcctgactt cgggctcctg ttacaagaga ggaatccagg | 1740 |
| agtttatttt gcagctgatt cagtgttgac caagagtcca gctctggggg agtgggaagc | 1800 |
| aaccaaagca gagacaggtc ccagcacaat ttttggtttt caagacagca cttctctgtg | 1860 |
| gctttgaagg ctatcctaga actgttcttt gtatatcctt ccttgcaact agctcttata | 1920 |
| gaccaggctg tccttgaact cacagagatc catctgcctc tgcctcccaa gtgctgggat | 1980 |
| taaaggcgtg cacctcggct gccaccaccc agctacatac ataatttaca ataataaaaa | 2040 |
| taaaatactt taaagtgtta tagcagtttg aatgtaattg gccctgtcat ctcataggga | 2100 |
| gtggcactat taggaggtat ggctttgttg aaggaaatat gtcactgtga gggtgggctg | 2160 |
| tgaggttttcc tatgctcagg gtaccagcca gtgtctcagc tgaggtcctg ttgcctgcaa | 2220 |
| gatgtaggac tctcatccct ttctccagca ccatgtctgt ctgcatgcca tcatgttccc | 2280 |
| agccatgatg acaatgtact aaaacctctg aaactgccac ccaactaaat gttttccttt | 2340 |
| ataagagttg ccatgctcat ggtgtctctt cacagcaata gaaaccctaa ctaagataag | 2400 |

-continued

```
tgtattctcc cctactcccc atgatttaaa atttaggaag gcaggtaggc aggcaggcag    2460
gctggtatag tggttcattc tagcacctga gacctggaat gggaggattg tgagttagtt    2520
ctaggccatt ctggtgccta gaaaccagag ccgggggttg gcccaatgca gagcacttgc    2580
tctacgtatg gcccagcaca ataagtcaat ttcctcacct taaaggcttg acaatttaaa    2640
aacactggtt tttagttagt ccgtgtctgc tccacagatg gagacagcta atcacagatg    2700
catcaggggc cttcctgagt gctaaacatc aaacagcctt ctcccctcct gagccttttgt   2760 gtgcagaatg tgtccatcgc aagaagcaaa cagtcttgct tgcccaccaa cttccttcct    2820
gcatcagaag agctgggtgc aaactgcaag agtagcctca ccttagagat gggtcccatt    2880
gctctacatg ggagcattac cttccaagaa ggcaaaaatg tctcctggtt gagcttttt     2940 tgtcacctgt taaaggcaaa tcaacagaga ggctttgtct cacccactaa catcttggaa    3000
acaaatacca acgaacgctg gggaggatgt ggggaaagca gagccctcat gctctccgag    3060
ggaaaatcac acccactgtg gaacagtgtg gaaacctcaa agactgggat tacaagcagc    3120
acacaagcca gccacgctac tcctggtcac acaccacaaa gacgcttgca cattcacgct    3180
tacgctgcga acactagcaa cgttcccact gcctcctttg agcccgcc   ccgcccctg    3240 cccccgccc cgcccctgtg gtctatgttc ctcttcccta aagtcagctt ccacttctct    3300
gtctccatct tcgccccacc ctccctcctc gctacataat tgtctctatt ccatttctct    3360
gctttgaaac agcttttgc aaagcatcaa atctattgtc ctatgcccca aatcaacctc    3420
cagtttcaca agtgatacag gaaatcgttt tcctaattaa aaatcccccc tttgaccatt    3480
tattcccact cttggaacat cttccccttg aggaaagtta cagaatgagg tggctctcct    3540
cttcctattc gaggtgtttc cttcagactt tgtccgtgtc taatcttttt aactgttggc    3600
caggcctcca ccacggcaca gatgaactgt ggggttcatt tacctgaaac tctatggaag    3660
gatgtttatt tctccttcac tttagcaaat gataaagggc accattcact ctgtctattc    3720
tgcaggggcc attcctttct ctaggccaga tactgagaat tgctcccaga atcaatgtgg    3780
tatacatatt tccccttcaa cattgatagg cattgatcac acacacacac acacacacac    3840
acacacacac acacagtagc acaaatgtat tccctagcc cgcttccatc ttgccacagg     3900
actccagagt ggccctggat agcaagcttc ctgttttgtt tctctgttcc tgctgctttt    3960
ccaccctcca gtctatcttt tctaagtcct tctgccattg tcctcttccc aactgtcctg    4020
agatgcagtc attgtctggg attcagacct tctctctctg cccaagtgag tatattgacc    4080
cccacggttt gtacaaccat aacttcaggg agcccgacaa aaactgtttt atgagccaag    4140
tagtcccagg acttgagagg tagaggcggg aagatcagca gtttgaggcc agcctggaga    4200
gcataagagc cggtctcaaa acaacaatgg aaactagata ctaagtaaaa atcctggggt    4260
gtttcatcat gaatgtctgt tcttctagta ccacgctgaa ctccgtacac agctccagct    4320
gttacggctt tcttagaatc catactcttt tttttttttt tttttttttt ttttttttgg    4380
tttttcgaga cagggtttct ctgtggcttt ggaggctgtc ctggaactag ctcttataga    4440
ccaggctggt ctcgaactca cagagatcca cctgcctctg cctccagagt gctgggatta    4500
aaggcgtgcg ccaccaacac ccggcagaat ccatactctt tttaaaaaaa gatttatcaa    4560
tttactatgt atacagcttt ctgcctgcat gtatccatgc atgtcagaag atggcaccag    4620
gtcgcattac agatggttgt gagccaccat gtggttgctg ggaattgaac tcagaatgtc    4680
tagaagagca accagttctc ttaacctctg agccatctct ccggcccccca gaaatccata    4740 ttcttgagga tttttttacac cccccccacc aaaagacgta tatctaaatt ttaatgtgag    4800
```

```
aattcacatt ttcttaagag ttgaacatag atttagagga aaatcagatc ccacatgatt    4860
aacaaagcat gcttgtgggc aggtctgcta ccaagaggtg ggccgtagct tctagctcag    4920
acaaactcac tcccttcctc gtggcctctt cgccctcaag tcagaaactc accctgtgat    4980
tctgccccag aagttgctct agagcacagt gcatccttcc gtcttcactc tgtggcttga    5040
attgtgtcca tcgcttatga ttacaacccc tcacagagca tcctaactgg tttctttgca    5100
tgcctatggg cactcctcca ttctagaaca cccttgccat caatactatg aaaggagggg    5160
tggaggagga agagcaggaa gaggaggggg aagcgaggga agaggaagac acggatggca    5220
atgaggaggg gggagcaccc aagtcctccc tggatgagag tctcactggg agacttaata    5280
ttaattataa atgcttggtc agcagctggg caggataagg ttaggcagga gaaccagact    5340
aaggactctg ggaagcagaa gggcagagtc agacaaggag aggaaacagg aagtacaagg    5400
taaagtcacg tggcagaatg tagataatag aaatggggttc atttaagttg gaagagttag    5460
ctagtaacaa gcctgagcta tcagccgagc atttataatt aatattgagc ctccatattg    5520
gttatctggg aattggcggg cagaaaaaaa aaagtctgcc tacaagtcaa tgtcatgtag    5580
ctcccaaagc caaggtacct ttgttcagtg cttgactgag ccagcattat aaattttctc    5640
cagatgtacc gaatcacatt tcatagcaac atgcagacat caagttttcc ctgaagctct    5700
aaccagctgg ttgcatgctg tccggagtct cagctataac ccagaagtga cctgggtcgg    5760
ggaagaggtg gtactttgcc ttctttgcac tctctgtgtt gcctcaccca ttcagcttca    5820
agcaatgtga ctgcctgacc ctgagggcgt ttacaacgcc tgaccacag accacaagtc     5880
aaccagctgg tgtgctcacg atacctagtc tgaaccatag ccctgctccc accctgcctc    5940
catctccacc ctttcttcac tgctcatcac agctggctag caaagactgc ctcagacctg    6000
agcacaggct ccactccaca gccgtgactg ttcgagccac ttaaatcaaa gagcgcttgt    6060
cttccgctca gtaaatctct cctcagctca ctgatgacgt tgactttctc tagacagcac    6120
atttgggttt aagacactgc tacttgagct cttcattcag ttcctcagaa tacctcattt    6180
gggtcagatt cccaaagagg aagatagggt tcctggcaga cagacatgtc tcattccttt    6240
gaaatccttc agagaaatgc agtgactatg gcaccttctt aaaaagcaca cacacaaata    6300
acacacacac acacacacac acacacacac acacacacac atatcccct cactgtcatc     6360
cttgatatgt atatgatata tataaaatca ttgtttata ctgtgataat tgattatgaa     6420
taaaatttac taaaatgaac aattaaaatt atgggggggg ctggagagat ggctcatcag    6480
ttaagagaac agttgctgct cttgcagaac acgagagttc agttcccagc acccacatca    6540
ggcagctcat aaccatgtgt ggtgtcagtt ccaggagatc tggtgccctc ttctggcctc    6600
ctccagcacc tgctacatgt ggttcacaca cacacacaca cacacacaca cacacacaca    6660
cacacacaca caaataaata taaagattat tttttttcaaa actgagttaa aaataggttc   6720
tatctgattc atactaaggc ttttcacagt ggttaagtct attagatatg tctagccata    6780
tcctttctcc cttctttctt gaggagaggc ttttaaagct acaagttaca gccttctttg    6840
caaataagag taccatttaa caggcctctg accaatgaga tgccagaatc ggttgcccag    6900
gagcttccca acagtccat tatagggaaa ggtggtacaa accagtagat taggcatgtt     6960
ccacttccta agtgccgtgc caaataagga aatggcctca aatgtttgcc ttttatcttc    7020
acccacctct gaattgcacg ctagt                                          7045
```

<210> SEQ ID NO 5
<211> LENGTH: 13515
<212> TYPE: DNA

<213> ORGANISM: Cricetulus griseus

<400> SEQUENCE: 5

```
tctagaaaca aaaccaaaaa tattaagtca ggcttggctt caggtgctgg ggtggagtgc      60
tgacaaaaat acacaaattc ctggctttct aaggcttttt cggggattca ggtattgggt     120
gatggtagaa taaaaatctg aaacataggt gatgtatctg ccatactgca tgggtgtgta     180
tgtgtgtgta tgtgtgtctg tgtgtgtgcc cagacagaaa taccatgaag gaaaaaaaca     240
cttcaaagac aggagagaag agtgacctgg gaaggactcc ccaatgagat gagaactgag     300
cacatgccag aggaggtgag gactgaacca ttcaacacaa gtggtgaata gtcctgcaga     360
cacagagagg gccagaagca ctcagaactc caggggtca ggagtggttc tctggaggct     420
tctgcccttg gaggttcctg aggaggggc ttccatattg aaaatgtagt tagtggccgt     480
ttccattagt acagtgacta gagagagctg agggaccact ggactgaggc ctagatgctc     540
agtcagatgg ccatgaaagc ctagacaagc acttccgggt ggaaaggaaa cagcaggtgt     600
gaggggtcag gggcaagtta gtgggagagg tcttccagat gaagtagcag gaacggagac     660
gcactggatg gccccacttg tcaaccagca aaagcttgga tcttgttcta agaggccagg     720
gacatgacaa gggtgatctc ggttttaaa aggctttgtg ttacctaatc acttctatta     780
gtcagatact ttgtaacaca aatgagtact tggcctgtat tttagaaact tctgggatcc     840
tgaaaaaaca caatgacatt ctggctgcaa cacctggaga ctcccagcca ggccctggac     900
ccgggtccat tcatgcaaat actcaggac agattcttca ctaggtactg atgagctgtc     960
ttggatgcaa atgtggcctc ttcatttac tacaagtcac catgagtcag gaggtgctgt    1020
ttgcacagtg tgactaagtg atggagtgtt gactgcagcc attcccggcc ccagcttgtg    1080
agagagatcc ttttaaattg aaagtaagct caaagttacc acgaagccac acatgtataa    1140
actgtgtgaa taatctgtgc acatacacaa accatgtgaa taatctgtgt acatgtataa    1200
actgtgtgaa taatctgtgt gcagcctttc cttacctact accttccagt gatcaggttt    1260
ggactgcctg tgtgctactg gaccctgaat gtccccaccg ctgtcccctg tcttttacga    1320
ttctgacatt tttaataaat tcagcggctt ccccctctgct ctgtgcctag ctataccttg    1380
gtactctgca ttttggtttc tgtgacattt ctctgtgact ctgctacatt ctcagatgac    1440
atgtgacaca gaaggtgttc cctctggaga catgtgatgt ccctgtcatt agtggaatca    1500
gatgcccccca aactgttgtc cagtgtttgg gaaagtgaca cgtgaaggag gatcaggaaa    1560
agaggggtgg aaatcaagat gtgtctgagt atctcatgtc cctgagtggt ccaggctgct    1620
gacttcactc ccccaagtga gggaggccat ggtgagtaca cacacctcac acatactata    1680
tccaacacac acacacacac acacacacac acgcacgcac gcacgcacgc acgcacacat    1740
gcacacacac gaactacatt tcacaaacca catacgcata ttacacccca aacgtatcac    1800
ctatacatac cacacataca cacccctcca cacatcacac acataccaca cccacacaca    1860
gcacacacat acataggcac acattcacac accacacata tacatttgtg tatgcataca    1920
tgcatacaca cacaggcaca cagacaccac acacatgcat tgtgtacgca cacatgcata    1980
cacacacata ggcacacatt gagcacacac atacatttgt gtacgcacac tacatagaca    2040
tatatgcatt tgtatatgca cacatgcatg cacacataca taggcacaca tagagcacac    2100
acatacattt gtgtatgcac acatgcacac accaatcaca tgggaagact caggttcttc    2160
actaaggttc acatgaactt agcagttcct ggttatctcg tgaaacttgg aagattgctg    2220
tggagaagag gaagcgttgg cttgagccct ggcagcaatt aaccccgccc agaagaagta    2280
```

```
ggtttaaaaa tgagagggtc tcaatgtgga acccgcaggg cgccagttca gagaagagac    2340
ctacccaagc caactgagag caaaggcaga gggatgaacc tgggatgtag tttgaacctc    2400
tgtaccagct gggcttcatg ctattttgtt atatctttat taaatattct tttagtttta    2460
tgtgcgtgaa taccttgctt gcataaatgt atgggcactg tatgtgttct tggtgccggt    2520
ggaggccagg agagggcatg gatcctccgg agctggcgtt tgagacagtt gtgacccaca    2580
gtgtggggtc tgggaactgg gtcttagtgt tccgcaagtg cagctgggc  cttaacctc    2640 tgagccatcc ctccagcttc aagaaactta ttttcttagg acatggggga agggatccag    2700
ggctttaggc ttgtttgttc agcaaatact cttttcgtgt attttgaatt ttattttatt    2760 ttacttttt  gggatagaat cacattctgc agctcaggct gggcctgaac tcatcaaaat    2820
cctcctgtct cagtctacca ggtgataaga ttactgatgt gagcctggct ttgacaagca    2880
ctttagagtc cccagcccct ctggacactt gttccaagta taatatatat atatatatat    2940
atatatatat atatatatat atatattgtg tgtgtgtgtt tgtgtgtgta tgagacactt    3000
gctctaaggg tatcatatat atccttgatt tgcttttaat ttatttttta attaaaaatg    3060
attagctaca tgtcacctgt atgcgtctgt atcatctata tatccttcct tccttctctc    3120
tctttctctc ttcttcttct caccccccaag catctatttt caaatccttg tgccgaggag    3180
atgccaagag tctcgttggg ggagatggtg agggggcgat acaggggaag agcaggagga    3240 aaggggggaca gactggtgtg ggtctttgga gagctcagga gaatagcagc gatcttccct    3300
gtccctggtg tcacctctta cagccaacac cattttgtgg cctggcagaa gagttgtcaa    3360
gctggtcgca ggtctgccac acaacccccaa tctggcccca agaaaaggca cctgtgtgtg    3420
actctggggt taaaggcgct gcctggtcgt ctccagctgg acttgaaact cccgtttaat    3480
aaagagttct gcaaaataat acccgcagag tcacagtgcc aggttcccgt gctttcctga    3540
agcgccaggc acgggttccc taggaaatgg ggccttgctt gccaagctcc cacggcttgc    3600
cctgcaaacg gcctgaatga tctggcactc tgcgttgcca ctgggatgaa atggaaaaaa    3660
gaaaaagaag aagtgtctct ggaagcgggc gcgctcacac aaacccgcaa cgattgtgta    3720
aacactctcc attgagaatc tggagtgcgg ttgccctcta ctggggagct gaagacagct    3780
agtgggggcg gggggaggac cgtgctagca tccttccacg gtgctcgctg gctgtggtgc    3840
atgccgggaa ccgaaacgcg gaactaaagt caagtcttgc tttggtggaa ctgacaatca    3900
acgaaatcac ttcgattgtt ttcctctttt tactggaatt cttggatttg atagatgggg    3960
gaggatcaga gggggagggg agggggcggg agacggaggg aggagggga gaggggagga    4020 ggggaggagg ggaggagggg aagggatgga ggaaaatact aacttttcta attcaacatg    4080
acaaagattc ggagaaagtg caccgctagt gaccgggagg aggaatgccc tattgggcat    4140
tatattccct gtcgtctaat ggaatcaaac tcttggttcc agcaccaagg attctgagcc    4200
tatcctattc aagacagtaa ctacagccca cacggaagag ctatacaac  tgaagaaata    4260 aaattttcac tttatttcat ttctgtgact gcatgttcac atgtagagag ccacctgtgt    4320
ctaggggctg atgtgctggg cagtagagtt ctgagcccgt taactggaac aacccagaac    4380
tcccaccaca gttagagctt gctgagagag ggaggccctt ggtgagattt ctttgtgtat    4440
ttatttagag acagggtctc atactgtagt ccaagctagc ctccagctca cagaaattct    4500
cctgttccgg tttccaaagt actggagtta tgagtgtgtg ttaattgaac gctaagaatt    4560
tgctgattga agaaacctc  aagtgggttt ggctaatccc cacgacccca gaggctgagg    4620
caggaggaat gagagaattc aaggtttgcc agagccacag ggtgagctca atgtggagac    4680
```

```
tgtgagggtg agctcaatgt ggagactgtg agggtgagct caatgtggag actgtgaggg    4740
tgagctcaat gtggagactg tgagggtgag ctcaatgtgg agactgtgag ggtgagctca    4800
atgtggagac ctgtatcaag ataataatag tagtagtaac aatgcaggcg agggtgtggt    4860
tgagtggtag agcagttagt tgatttgaca tgcttgaggt ctcccggtcc atctgtggcc    4920
ctgcaacagg aagggaggga ggaaggggg gaacgagaga gaggaaagag agacagaagc     4980 taagatagg aatgagagag gaaggaagaa acgggaagaa attcagactc cttcctgagt     5040
tccgccaacg cctagtgaca tcctgtgcac accctaaggt ggcctttgtg tggcactggc    5100
ttgggtggtc gggaaaggca ttttcagctt gttgcagaac tgccacagta gcatgctggg    5160
tccgtgaaag tttctgcccg ttaacaagaa gtctctacta cttgtgacct caccagtgaa    5220
aatttcttta attgtctcct ggtgttctgg gttttgcatt tttgtttcta aggatacatt    5280
cctgggtgat gtcatgaagt ccccaaagac acagtggggc tgtgttggat tgggaaagat    5340
gatttatctg gggtgtcaaa aggaaaagaa gggaaacagg cacttgggaa aatgtcctcc    5400
cgcccacccg aattttggct tggcaaccgt ggtggaggag caagaaacac gtggacgttt    5460
gaggaggcat ggggtcctag gaggacagga agcagaagga gagagctggg ctgacagcct    5520
gcaggcattg cacagtttca gaaggagatt acagcatgac tgagttttta gggatccaac    5580
agggacctgg gtagagattc tgtgggctct gaggcaactt gacctcagcc agatggtatt    5640
tgaataacct gctcttagag ggaaaacaga catagcaaac agagccacgt ttagtgatga    5700
aactctcact ttgcctgagt catgtgcggc catgcccagg ggtcaggctg acactcaact    5760
caaaaacaag tgagaaattg aagacaatcc gtggtggcag ctactggaag ggccaccaca    5820
tccccagaaa gagtggagct gctaaaaagc catttgtgat aggcacagtt atcttgaatg    5880
catggagcag agattacgga aaaatcgaga atgttaatga ggcaacattc gagttgagtc    5940
attcagtgtg ggaaacccag acgcttccat cccctaaaag gaacatcttg ctctcagtca    6000
aaatggaaat aaaaattggg gcttgaattt ggcaaatgat tcagaactct gtgtaggtat    6060
tttcacacgc acagtggata attttcatgt tggagtttat ttgtgctaaa aggcagaaaa    6120
gggtaaaaag cacatcttaa gagttatgag gttctacgaa taaaaataat gttacttaca    6180
gctattcctt aattagtacc cccttccacc tgtggtaatt tcctgagata gtcagtgggg    6240
aaaagatctc tccttctctt ttttctcccc ctccctcct ctccctccct ccctccctcc     6300
ctccctcctc tccctccctc cccctttcct tctttctttg ctccttctcc tctgcctcct    6360 tctcccttc ttcttcattt attctaagta gcttttaaca gcacaccaat tacctgtgta     6420
taacgggaaa acacaggctc aagcagctta gagaagattg atctgtgttc actagcgtgc    6480
aattcagagg tgggtgaaga taaaaggcaa acatttgagg ccatttcctt atttggcacg    6540
gcacttagga agtggaacat gcctaatcta ctggtttgta ccacctttcc ctataatgga    6600
ctgtttggga agctcctggg caaccgattc tggcatctca ttggtcagag gcctgttaaa    6660
tggtactctt atttgcaaag aaggctgtaa cttgtagctt taaaagcctc tcctcaagaa    6720
agaagggaga aaggatatgg ctagacatat ctaatagact taaccactgt gaaaagcctt    6780
agtatgaatc agatagaacc tattttaac tcagttttga aaaaaataat ctttatattt     6840
atttgtgtgt gtgtgtgtgt gtgtgtgtgt gtgtgtgtgt gtgtgtgtgt gaaccacatg    6900
tagcaggtgc tggaggaggc cagaagaggg caccagatct cctggaactg acaccacaca    6960
tggttatgag ctgcctgatg tgggtgctgg gaactgaact ctcgtgttct gcaagagcag    7020
caactgttct cttaactgat gagccatctc tccagcccc cccataattt taattgttca     7080
```

```
ttttagtaaa ttttattcat aatcaattat cacagtataa aacaatgatt ttatatatat    7140
catatacata tcaaggatga cagtgagggg gatatgtgtg tgtgtgtgtg tgtgtgtgtg    7200
tgtgtgtgtg tgtgttattt gtgtgtgtgc ttttaagaa ggtgccatag tcactgcatt     7260
tctctgaagg atttcaaagg aatgagacat gtctgtctgc caggaaccct atcttcctct    7320
ttgggaatct gacccaaatg aggtattctg aggaactgaa tgaagagctc aagtagcagt    7380
gtcttaaacc caaatgtgct gtctagagaa agtcaacgtc atcagtgagc tgaggagaga    7440
tttactgagc ggaagacaag cgctctttga tttaagtggc tcgaacagtc acggctgtgg    7500
agtggagcct gtgctcaggt ctgaggcagt cttttgctagc cagctgtgat gagcagtgaa    7560
gaaagggtgg agatggaggc agggtgggag cagggctatg gttcagacta ggtatcgtga    7620
gcacaccagc tggttgactt gtggtctgtg ggtcaggcgt tgtaaacgcc ctcagggtca    7680
ggcagtcaca ttgcttgaag ctgaatgggt gaggcaacac agagagtgca aagaaggcaa    7740
agtaccacct cttccccgac ccaggtcact tctgggttat agctgagact ccggacagca    7800
tgcaaccagc tggttagagc ttcagggaaa acttgatgtc tgcatgttgc tatgaaatgt    7860
gattcggtac atctggagaa aatttataat gctggctcag tcaagcactg aacaaaggta    7920
ccttggcttt gggagctaca tgacattgac ttgtaggcag actttttttt ttctgcccgc    7980
caattcccag ataaccaata tggaggctca atattaatta taaatgctcg gctgatagct    8040
caggcttgtt actagctaac tcttccaact taaatgaacc catttctatt atctacattc    8100
tgccacgtga ctttaccttg tacttcctgt ttcctctcct tgtctgactc tgcccttctg    8160
cttcccagag tccttagtct ggttctcctg cctaaccta tcctgcccag ctgctgacca    8220
agcatttata attaatatta agtctcccag tgagactctc atccagggag gacttgggtg    8280
ctcccccctc ctcattgcca tccgtgtctt cctcttccct cgcttccccc tcctcttcct    8340
gctcttcctc ctccacccct cctttcatag tattgatggc aagggtgttc tagaatggag    8400
gagtgcccat aggcatgcaa agaaaccagt taggatgctc tgtgagggt tgtaatcata     8460
agcgatggac acaattcaag ccacagagtg aagacggaag gatgcactgt gctctagagc    8520
aacttctggg gcagaatcac agggtgagtt tctgacttga gggcgaagag gccacgagga    8580
agggagtgag tttgtctgag ctagaagcta cggcccacct cttggtagca gacctgccca    8640
caagcatgct ttgttaatca tgtgggatct gattttcctc taaatctatg ttcaactctt    8700
aagaaaatgt gaattctcac attaaaattt agatatacgt cttttggtgg gggggtgta     8760
aaaaatcctc aagaatatgg atttctgggg gccggagaga tggctcagag gttaagagaa    8820
ctggttgctc ttctagacat tctgagttca attcccagca accacatggt ggctcacaac    8880
catctgtaat gcgacctggt gccatcttct gacatgcatg gatacatgca ggcagaaagc    8940
tgtatacata gtaaattgat aaatcttttt ttaaaagag tatggattct gccgggtgtt     9000
ggtggcgcac gcctttaatc ccagcactct ggaggcagag gcaggtggat ctctgtgagt    9060
tcgagaccag cctggtctat aagagctagt tccaggacag cctccaaagc cacagagaaa    9120
ccctgtctcg aaaaccaaa aaaaaaaaa aaaaaaaaa aaaaaaaga gtatggattc        9180
taagaaagcc gtaacagctg gagctgtgta cggagttcag cgtggtacta aagaacaga    9240
cattcatgat gaaacacccc aggattttta cttagtatct agtttccatt gttgttttga    9300
gaccggctct tatgctctcc aggctggcct caaactgctg atcttcccgc tctacctct    9360
caagtcctgg gactacttgg ctcataaaac agttttgtc gggctccctg aagttatggt     9420
tgtacaaacc gtgggggtca atatactcac ttgggcagag agagaaggtc tgaatcccag    9480
```

```
acaatgactg catctcagga cagttgggaa gaggacaatg cagaaggac ttagaaaaga      9540 tagactggag ggtggaaaag cagcaggaac agagaaacaa aacaggaagc ttgctatcca    9600
gggccactct ggagtcctgt ggcaagatgg aagcgggcta ggggaataca tttgtgctac    9660
tgtgtgtgtg tgtgtgtgtg tgtgtgtgtg tgtgtgtgat caatgcctat caatgttgaa    9720
ggggaaatat gtataccaca ttgattctgg gagcaattct cagtatctgg cctagagaaa    9780
ggaatggccc ctgcagaata gacagagtga atggtgccct ttatcatttg ctaaagtgaa    9840
ggagaaataa acatccttcc atagagtttc aggtaaatga accccacagt tcatctgtgc    9900
cgtggtggag gcctggccaa cagttaaaaa gattagacac ggacaaagtc tgaaggaaac    9960
acctcgaata ggaagaggag agccacctca ttctgtaact ttccctcaagg ggaagatgtt   10020 ccaagagtgg gaataaatgg tcaagggggg gattttttaat taggaaaacg atttcctgta   10080
tcacttgtga aactggaggt tgatttgggg cataggacaa tagatttgat gctttgcaaa    10140
aagctgtttc aaagcagaga aatgaataga agacaattat gtagcgagga gggagggtgg   10200
ggcgaagatg gagacagaga agtggaagct gactttaggg aagaggaaca tagaccacag    10260
gggcggggcg gggggcaggg gcggggggcg gggctcaaag gaggcagtgg gaacgttgct    10320
agtgttcgca gcgtaagcgt gaatgtgcaa gcgtctttgt ggtgtgtgac caggagtagc    10380
gtggctggct tgtgtgctgc ttgtaatccc agtctttgag gtttccacac tgttccacag    10440
tgggtgtgat tttccctcgg agagcatgag ggctctgctt tccccacatc ctccccagcg    10500
ttcgttggta tttgtttcca agatgttagt gggtgagaca aagcctctct gttgatttgc    10560
ctttaacagg tgacaaaaaa agctcaacca ggagacattt ttgccttctt ggaaggtaat    10620
gctcccatgt agagcaatgg gacccatctc taaggtgagg ctactcttgc agtttgcacc    10680
cagctcttct gatgcaggaa ggaagttggt gggcaagcaa gactgtttgc ttcttgcgat    10740
ggacacattc tgcacacaaa ggctcaggag gggagaaggc tgtttgatgt ttagcactca    10800
ggaaggcccc tgatgcatct gtgattagct gtctccatct gtggagcaga cacggactaa    10860
ctaaaaacca gtgtttttaa attgtcaagc ctttaaggtg aggaaattga cttattgtgc    10920
tgggccatac gtagagcaag tgctctgcat tgggccaacc cccggctctg gtttctaggc    10980
accagaatgg cctagaacta actcacaatc ctcccattcc aggtctcagg tgctagaatg    11040
aaccactata ccagcctgcc tgcctgccta cctgccttcc taaattttaa atcatgggga    11100
gtagggagaa atacacttat cttagttagg gtttctattg ctgtgaagag acaccatgag    11160
catggcaact cttataaagg aaaacattta gttgggtggc agtttcagag gtttttagtac   11220 attgtcatca tggctgggaa catgatggca tgcagacaga catggtgctg gagaaaggga    11280
tgagagtcct acatcttgca ggcaacagga cctcagctga gacactggct ggtaccctga    11340
gcataggaaa cctcacagcc caccctcaca gtgacatatt tccttcaaca aagccatacc    11400
tcctaatagt gccactccct atgagatgac agggccaatt acattcaaac tgctataaca    11460
ctttaaagta tttattttt attattgtaa attatgtatg tagctgggtg gtggcagccg      11520
aggtgcacgc ctttaatccc agcacttggg aggcagaggc agatggatct ctgtgagttc    11580
aagaccagcc tggtctataa gagctagttg caaggaagga tatacaaaga acagttctag    11640
gatagccttc aaagccacag agaagtgctg tcttgaaaac caaaaattgt gctgggacct    11700
gtctctgctt tggttgcttc ccactccccc agagctggac tcttggtcaa cactgaatca    11760
gctgcaaaat aaactcctgg attcctctct tgtaacagga gcccgaagtc aggcgcccac    11820
ttgtcttctc gcaggattgc catagacttt ttctgtgtgc ccaccattcc agactgaagt    11880
```

```
agagatggca gtggcagaga ctgggaaggc tgcaacgaaa acaggaagtt attgcaccct   11940
gggaatagtc tggaaatgaa gcttcaaaac ttgcttcatg ttcagttgta cacagactca   12000
ctcccaggtt gactcacacg tgtaaatatt cctgactatg tctgcactgc ttttatctga   12060
tgcttccttc ccaaaatgcc aagtgtacaa ggtgagggaa tcacccttgg attcagagcc   12120
cagggtcgtc ctccttaacc tggacttgtc tttctccggc agcctctgac accccteccc   12180 ccattttctc tatcagaagg tctgagcaga gttggggcac gctcatgtcc tgatacactc   12240
cttgtcttcc tgaagatcta acttctgacc cagaaagatg gctaaggtgg tgaagtgttt   12300
gacatgaaga cttggtctta agaactggag caggggaaaa aagtcggatg tggcagcatg   12360
tacccgaaat cccagaactg ggaggtagga acggatgag tgcccggggc tagctggctg   12420
ctcagccagc ctagctgaat tgccaaattc caactcctat tgaaaaacct ttaccaaaca   12480
aacaaacaaa caaataataa caacaacaac aacaacaaac taccccatac aaggtgggcg   12540
gctcttggct cttgaggaat gactcaccca aacccaaagc ttgccacagc tgttctctgg   12600
cctaaatggg gtgggggtgg ggcagagaca gagacagaga gagacatgac ttcctgggct   12660
gggctgtgtg ctctaggcca ccaggaactt tcctgtcttg ctctctgtct ggcacagcca   12720
gagcaccagc acccagcagg tgcacacacc tccctccgtg cttcttgagc aaacacaggt   12780
gccttggtct gtctattgaa ccggagtaag ttccttgcaga tgtatgcatg gaaacaacat   12840
tgtcctggtt ttatttctac tgttgtgata aaaaccgggg aactccagga agcagctgag   12900
gcagaggcaa atgcaaggaa tgctgcctcc tagcttgctc cccatggctt gccgggcctg   12960
cttcctgcaa gcccttctct ccccattggc atgcctgaca tgaacagcgt ttgaaatgct   13020
ctcaaatgtc actttcaaag aaggcttctc tgatcttgct aactaaatca gaccatgttt   13080
caccgtgcat tatctttctg ctgtctgtct gtctgtctgt ctgtctatct gtctatcatc   13140
tatcaatcat ctatctatct atcttctatt tatctaccta tcattcaatc atctatcttc   13200
taactagtta tcatttattt atttgtttac ttactttttt tatttgagac agtatttctc   13260
tgagtgacag ccttggctgt cctggaaccc attctgtaac caggctgtcc tcaaactcac   13320
agagatccaa ctgcctctgc ctctctggtg ctggggttaa agacgtgcac caccaacgcc   13380
ccgctctatc atctatttat gtacttatta ttcagtcatt atctatcctc taactatcca   13440
tcatctgtct atccatcatc tatctatcta tctatctatc tatctatcta tctatcatcc   13500
atctataatc aattg                                                     13515
```

<210> SEQ ID NO 6
<211> LENGTH: 14553
<212> TYPE: DNA
<213> ORGANISM: Mus musculus

<400> SEQUENCE: 6

```
cttgaagaac acatgttttc caagagggag cacccatgtt ggaatgacaa tgtagttagt     60
gctcctctcc tgtaggttag tgctcctttg ctataggtaa gtgctcctct cctataggtc    120
agtgctcctc tcctataggt tagtgctcct ctcctataggt ttagtgctcc tctcctacag   180
gttagtgctc ctctgctcta ggttagtcct gctctcctat agtacctaga gagctagggc    240
aaatgggcta ggcccgaagt gcagagacaa acagctatgg aagactgggt aagcacttcc    300
aagctacgaa agagcagtgt gaagggtcag ggcttgtgca gttagtaggg gagatcttcc    360
agttgaagaa acagaagaac tgagagccac tgggtatcat cctcctgcgc catgccttcc    420
tggatactgc catgctccca ccttgatgat aatggaatga acctctgaac ctgtaagcca    480
```

```
gccccaatga aatattgttt ttatgagagt tgccttggtc atgctgtctg ttcacagcag    540 taaaaccccta aataaggcag aagttggtac cagtattgct gtgatagacc tgaccatgct    600
ttcctttgaa agaatgtgga tttggtgact ttggatttgc aacacagtgg aatgctttaa    660
atggagatta atgggtcatc aattcctagt aggaatatgg aagactttgt tgctgggagt    720
atttgaactg tgttgacctg gcctaagaga tttcaaagga gaagaatttc agaatgtggc    780
ataaagacag ttttttgtggt atttttggtga agaatgtggc tacttttttgc ccttgtctga    840 aaagtctgcc tgagactaaa gtgaagagaa tcagattaat tgcattgaca agggaagttt    900
gtggctgcgc tatctggaaa cttacagcca gcctcttgga cctcgggtga cttacgcaaa    960
tactcaggga cagagatgct tgactctgta ctgatgagtt gtcttggatg caaatatggg   1020
ctcttcattt gactacatgt cacgatgagt caggagctgc tctctccaga gtgtgacaaa   1080
gcgaggggat gctgacggta gctgttctag cttgaaggt aagcctgcac ttatgctaaa   1140
gtcacacata cacgagccgg gtggagaacc tgtctgtgtg gagacacctt tcattacctg   1200
tggcatccag cctctcaagc ttggactgcc tgtgtgctcc tggactctgg aggtcccact   1260
gctctgtcct ctgctgctta tgatactgac attttaaag aatccagtgg ttccccctg   1320 tactcggtgt ctacttctac ctggatgttc ctcatttatg ttctgtgaca cttctctgtg   1380
actctgctgc attcctgggt gacatgtgga caccctgtcc ctttgcagac catgatgtca   1440
ctgtcactag tggaatcaga tgccccaagt gttgtcctgt gtttgggaac gtgacaggca   1500
gtacagaagc agaagaggaa gggtgaaaac ggaaatgtca cagcagcatc tgatgtgtgc   1560
ctcagtcacg catgctgctg attggaacta ctcagcatga gagagggcca tggtgaatac   1620
acaaccctat acacactgtg tccatttctc tctctctctt acacagagag agagggagga   1680
gggggagggg gaggcggagg gggaggggga gggagggga gtgggagagg gagagggaga   1740
gggagaggga gagggagagg gagagggaga gggagagttt aatgtctgtg aagagatacc   1800
atgaccaaag caactcttat aaaggacaac atttaattgg ggctggctta caggttcaga   1860
aattcagtcc attctcacca tggtgggaag catgcaggta gatgtggtgc tggaggaacc   1920
aagagttcta tatcctgatc tgaaggcagc caggagaaga ctgcctcttc tgcacagggc   1980
agagcttgag catagaacat caaagcccctt ccccacactt cctccaacaa ggtcatacat   2040
acttcaacaa agacacacct cctaacggtg ccactccctg tggaccaacc atttaaacgc   2100
atgagtctat gagggtcaaa gctcttcaaa ccaccacact catgtacaca cacacacaca   2160
cacacacaca ctctcataca cacacacaca cacactcaca cacacacaca cacacacaca   2220
cacacacaca ccacacacac acacacacac agagttctat tttgcactgt tcactgtca   2280 caaggttcta cttatctcag acacactgcc aggaattgtg tgggaagact ttcagtttct   2340
ttgggttcac atggacttag cagttcttgg tgatcctgaa agatttctgc agaaagaagc   2400
caaagtgttg agcccaaggc ctggccacac attagtcctg tctagatgaa caggggttta   2460
aaaataaggg ggcatcaagg tgaagccagc aggggctgac ttagagagga gacccaccca   2520
agccaactgc tcgaagtcaa aagcgatgaa tccccatatc cagctgtgcc cggtgctgtc   2580
ttgctacatc tttagtaaat gttcttttag ttgtatgcgt atgaatattt tgcttgcata   2640
tatttgtgta caccataggt gttcctaggg cctatggagg ccagaagagg gcatcagatc   2700
ctttggaact ggaattatag acacttgtta cccatagagt agattgtggg aaatgagcct   2760
ttagtcttcg agagcggcca gtgctcttaa cctttggtcg tttctccagg tctttgagac   2820 tttatttct tggacatcag gacaggatcc agggctttga gcttgtttct tcagccagct   2880
```

```
ttcttttcat gtatattaaa ttttatgtta ttttgctttc ttttccccca agacagaatc    2940
acactctata tagctcaggc tgggtttgaa ttcagtttcc ctgtctcagt ctaccgggta    3000
atatgattac agatgtgagt ctgactttgg tatcaaagtc cccagcccct ctggatatgt    3060
gttttaagga tatcagatat atccttgatt tgctttgaat tttcttttta gttacaacat    3120
aattagttcc gtgtcacctg aatatgtgta tgtcacctac atagtcttcc ttcttctctt    3180
cttccctctc ccaccttccc aggtacctgt ctgtcttcat atccttgtgc tgagagtctt    3240
gttgagggag atgatgaccg agacagagcc actggggaag ggagatgggc tagtgcaggt    3300
cttcagagag gagctcgtga atattgtagc ccctttagtc cctggcatgt cctcttgtat    3360
agccaccgcc atgctgtggc ctggcagaag tgaataagtt gtccagctgt tgacaggcct    3420
gccctccaga cccagtctga tcccaagaaa gggcatctgt gtctgtctct gaggccgtaa    3480
gtgctgcctg gttgtctcca gcttgacttg acactccctc cttaataaga gtaccacaga    3540
acagggtctg cagagtccct gggccaggtc cctgtgctgt cctggaatgc caggcgtgaa    3600
tttcctgtga agtaggactt tgctcgccaa gctcccacgg cttgcccttc agatagccag    3660
aattatctgg taccctgcat tgccgttcaa tacgcagagt atcactggaa gcgcgcgcgc    3720
gcacacacac acacacacac acacacacac acacacacac acacgcccac tccatcttta    3780
aaccccaccc cccagcaacg gcggtgtaaa cactctccat caggaagctg aaacgcagtt    3840
gccctctgct ggggagatga aggcagcttg ctggggcgga ggaccgtgct agcaaccttc    3900
cctggtgcac acgggctctg gtgcatgacg ggaacggaaa cgcggaacta agtcagtcc     3960 tgctttttt tttttttttt tttttttttt tttttttttt tttttttttt ggcgttggtg     4020
gtggactgag tgacaatcag tgaaatcact taggttgttt ttctcttctt cgttgggttt    4080
gatagacggt gggagagggt cagaggagaa ggggagggat ggggagagag ggaggaggga    4140
ggggcgggag gcgggggggcg aggaaaacgt gctaacttct ccaatcctac aagacaaagg   4200
tttggagaaa gccgcactga gtgacccagc agaaggaatc caggaatgtc cgctggaatc    4260
tgactgttga ttccagcgcc atgcagagaa tctaggctgg taggaacatt ctttgtccta    4320
tccgacataa taactccaac caacacgaaa agaaaggct atacaagtga agaaatggca     4380
ttttcacttt catgactata caatcacttc caggtagtaa cacgtgtcta gcacagcggt    4440
tctcaacctg ggggtcacga tcccccactt ttctgcatat cagacatttt tacgttgtta    4500
ttcataacag tagcaaaatt gcagctatga agtaacaatg aaatgcattt atggtgcgtg    4560
tgtgtgtgtg tgggggggta tcaccttaac atttactgta agaaggttga gaatactgct    4620
ccagcagcta gtgtgttgga cttaggttct gggtatatta ttagcaatag ccaaccagaa    4680
tccccaccca ccacagcatt gaggccccat gcagggcttg ctgggagagg cactgataag    4740
acttctttat gtatttattt agagacgaat actcattagg taggccaagc tagcgtcaaa    4800
ctcatggcaa ttctcctcct ccagtttcct aagtactgga ctcaggagtg tgttgccatc    4860
atatacagta aggatttatt gactgaagaa atctcaagt ggctttggtt aatccctact      4920
acgccagagg ctgaggcagg aggcgcgcaa ggtcaaggct tgcctgggct acatatagag    4980
tgagctcaat tttgacactt ggtgcggtgt tagtagtaat agtaaagatg aaggtgtggc    5040
tcaggtgggg ccggtgattg gacacacttg gggtctcctg gtccatctgc agctgtgcaa    5100
caggaagagc ggagaatgag aggaaagaga gaaagacag aatgagagag agggaggaag     5160
agagaaaaag gaaagagag aggaaaggaa aaggaaaaat gaggaaagcg agaaagaaga     5220
aatgagaaag aggaaaggga gaaagaaatg agagagagaa aagaaaagac agaatgcgag    5280
```

```
agagggagga agagagaaaa aggaaaagag agaggaaagg aaaaaggaaa atgaggaaag      5340
cgagaaagaa gaaatgagaa agaggaaagg gagaaagaaa tgagagagag aaaagaaaag      5400
acagaatgcg agagagggag gaagagagaa aaaggaaaag agagaggaag ggaaaaagga      5460
aaatgaggaa agcgagaaag aagaaatgag aaagaggaaa gggagaaaga aatgagagag      5520
agaaaagaaa agacagaatg cgagagaggg aggaagagag aaaaaggaaa agagagagga      5580
agggaaaaag gaaaatgagg aaagcgagaa agaagaaatg agaaagagga aagggagaaa      5640
gaaatgagag agagaaaaga aaagacagaa tgcgagagag ggaggaagag agaaaaagga      5700
aaagagagag gaagggaaaa tggaaaatga ggaaagcgag aaagaagaaa tgagaaagag      5760
gaaagggaga agaaatgag cgagataaaa gacagaattt gagagaggga ggaagaaata      5820
ggaaaagaga ggaaaggatg gagaaagag agaaagaaag agatgaaa gagagaaagg      5880 agaaatgaaa tgagagagag agagagacac aaagagccag agagagaaga aaaagggga      5940 aagagaaaga gaaagaggaa ggctcctctt ggacacatct tcctttatct ttccctgggg      6000
accgccaaag cctggtggca tactgtacat tctgtacact gttcattcaa aacaggctct      6060
gtcttaaaga tggtctgagc ggtcagaaaa gggtattgtt aacttgtttg caaaactgcc      6120
tcaggagagt gctgagtgcg tgaaagttgc tgcccgttaa ggagaagtct ctactacttg      6180
tgatctcacc atcgaaaatt tctttaattg tctcctggtg ttctgggttt tgcagttttg      6240
tttctaagga tacattcttg ggtgatgtca caaagtcccc aaagacacgg tggagctgtg      6300
ttagatgggg aaagacagtc tgctgaggat ttatctggaa ctgtcagaag gaaaagaagg      6360
taaatggggc acttgggaaa gtggcctcta gtttgacttc tggcttagca aaggttgtgg      6420
ggagataagg catacacagt agttagcagg aggcaacagg gtcctgggag gacgcgaggc      6480
agaaggagag gctgggctga cagcatgcaa tcattgcata gtctccaaag gagattgcaa      6540
catggctgag ttttcagagg tcctacagag cccgtggtag agattctgtg ggttctgaga      6600
caacttgact ttagccagat ggtatttgag taatctggga gagagaaaac agctacagca      6660
aacagggcca catttagtga cgaaactctc actttgactg ttgagtcatt tgcagtgggc      6720
cctgaggtca ggctggccct cagctcaaaa acaagcgagg aactgaagca attactcaga      6780
taatccacag ccacagccac tggaaagggc cacatcccca gagacagcac agcaggggtg      6840
ggggtggggc tatgagaaag ttagtgattg tagcagttat ctagaatgtg cggagcagag      6900
gaggttacac aaaaacctag aatgtcattc aatgtgggaa accgagaggc tcccaagccc      6960
taaaaggaac agtttgcttt cagccaaaat ggaaataaaa tttggggctt aaatctggca      7020
aatgattcag accttctgtg taggtgtctt taaatgcaca gcagattgat tttcatgttg      7080
gagtttattt gaactaaaag acagaaatgg tgaaaagcac acctgaagaa attgagatgc      7140
tatgaataaa atcatttact tacagctatc acttaattag tacctccttc caccttgctg      7200
atttattggg ctagtcaagg aagaaaagat cttccctcct ccttctctcc tcctcccct      7260 cctctcctcc tcccctcccc tccttgacct tcctctcctc cttttccctc ctcccctct      7320 tcttctcttc accccctcct cccctcccct cctctgtact cctccccttt cctcccaatc      7380
tcttttttct ccccttcctt ctctttctcc ccctcctct tcctcctct tcctccctcc      7440 ctccctcctc ctcctcatcc tcctcttcct cttcatcctc ttctccttcc tccctctcct      7500
cctcctcctt ttccagccct acctaccttc cctttcttct tcatttattc aaagtagctt      7560
tgaacagcac tactcggttt agttgtgtat aaaaggaaaa tgcaggtcca agcagcttgg      7620
ggaagattgc ttttgctct ctggaggcag atgatgacag ttcaagatca ttcctttgc      7680
```

```
tccatgtcac aggaaggggg acatgccgaa tctaccagtt tgcagccacc tacacaggat    7740
ccaccttcac ttctaaggaa atgtttggga agctacctac caaccacttc tggcatctca    7800
tgggctagag gactcttaaa tggcactctt atttgtttaa taaaggaggt tgtgacgtgt    7860
agttttaaat cccttccaca caacaattgc tactctctga ccaaaaaaga agggagacag    7920
gatacggcta ggtgtctagt agactttacc actttgaaaa gccttaatat aaatcaggta    7980
gatacatctt tttaacttat tcttgtaaag acaaaaacaa aactttattt ttatttgtgt    8040
gtatgcttgt gtgtgtgtgc ctgtgtgtat accacatgtc gctggtgccg gagaacacca    8100
gaagagggga cctgatctcc tggagctaaa gctatccatg gttctgagct gcctgatgtg    8160
ggtgctggga acagaactct ggtcttctgc aagagcaaca agcctcctct taactacgaa    8220
tctcctcccc atcccccaa atacatttaa ttattcattt tagcagcttt atttcgtaac    8280
tacttatcac agcataaaac aaggattta tatatattac atgcaatcga ggataagagt    8340
tgaggggaga tgcgtgtgct ccttctgggt gtctgtgctt ttgaagaatg taagcagtgc    8400
acaagggacc gaggcgtgcc tgtctgccag gagctgtctt cttcccttgg actctgagct    8460
gagtgcagtg ctccgaagaa gtaaaagacg acctcatgaa gcaatgtctt caacccaaac    8520
atgctgtcca gacaaagtcc agcttcatta gtgctctgag gagagactta ctgagcctca    8580
ggaaagcccc cctcagcatg gcgaaagtcc actttgattg aagtgactcg aaagccatgg    8640
cagtgcggcg gcggccgcgt ggagcttgtg ctcgagtcgg aagcggcatc tttgtcaggc    8700
ggctgtgatt agcacgggga ggcaggactg gagtgaagga agagttgggg gcggggctta    8760
gcgctctggt ctcctaagct gtagtcagcg cctcaagatt tgtaacctgc cttctgcctt    8820
cccagccagg cagtcaagtg gctccaagct gaagactgca aagtgcccct aaccttttgg    8880
ttatagcgag gctgaagaca ccgtgctctt tcatgaaagc cggatgtctg aaatccgatt    8940
tgataaatat ggataaaacg tataacgctc gatcaatcga atcgaaggag ctcacgattg    9000
gcaccacggc tttggggaca acagagtact gactcgttgg gaggacttgg atacttcccc    9060
tcctcttcca tctcttcccc tttcctcact tcctcctcct tccttctcca ttttctccct    9120
cttcactgtt tcttactatt tttacaaaag attttattta tttatttatt tatttattta    9180
tttatttatt tatttattta tttatttaat gtatgcgagt acactgtagc tgtcttcaga    9240
cacaccagaa gagggcgtca agttccatta gagatggttt cgagccacca tgtggttgct    9300
ggggcctctg gaaggaccgc cagtgctctt aaccctgag ccatttctcc agtacccttc    9360
tcaccgtttc tcttcaatct tcttcctctt ccttctccac tttccttgtc ttcttggttt    9420
cattatcttt ctccctttct tcctcttctc cccttcttcc tcctccactg tagttttcct    9480
tccctactct tttcctgcct ccctcctcct ccccctctcat tcccctcct ctttcctcct    9540 tctccctcct cctccttcct tctccctctc ccctctcccc tctcccttct cccttctccc    9600
cctcctcttc ctctttctcc ttctccaccc ctcctgtcac agtatcaatg gcaagggtgt    9660
tctagaatgg aggagtgtcc cctaggcact aacgaaagcc agttaggatg ctctgagacg    9720
ggtacaattc agggagggcc gtggggatgg aagggttgtg ctgcgattca ttctggagca    9780 accccccaggc agaatcatga ggttggttcc ggattcgcag ggcacaattc agaagaggaa    9840
ggtttcagga aggacgagtt tgtctgagat aggagttaca tctgatgtct tggcagcaga    9900
gccactgtac aagcgtgctt tattaaccac gtgggattaa atcttctttt aaatttattt    9960
tcaactctta aggaaacgtg aactttcaca ttcaaattta gacttgcagc tcttatgggg   10020
aaaaaaaggg gatcttaaga atattaagca taggcggctg gagagatggc tcagcggtta   10080
```

```
agagcactct ctgctctccc agaggtcctg agttcaattc ctagcaacca cataatagtt    10140
aacaacagtc tttaatgaat tctaatgccc tcttctggtg tgtctgaaga cagttacagt    10200
gtactcatat aaataaaata aagaaattta aaaaaatgaa tattaggcat agattcctgg    10260
atcctaagaa agccatcaga gctggagcca tgtgtgggat cctgcttggt gctggagggg    10320
cagagttcat gcccccgggg tttttactta ttatcacatt ttcatcgttg ttttgaaaca    10380
gggtcttgtg tggtccaggc tggccttgaa ctcatctttc agcctctacc tcacaggttc    10440
tgggattact tggttcctaa agtatctccc gtcaagctcc ctggtgttat ggctgtgcca    10500
accaggaggg tctatacact cgctcaggta gagggagaag atccgaatct ctgacaggga    10560
ctgctgcctc tcggggcaaa tggagtgaag acagcggca aaggattta ggaaagatgg    10620 acggagagt ggaaatgctg cagaagccag aaaacaaagc aggaagcctg ctgtccagtg    10680
gggctcaaga gcggagggat gcgaggggc tgcgcaggaa catttagcgt ctgcgtctat    10740
gggggtaggg gcggggtgcc agcacctagt cacctgaagg ggaaatgctt gcccaggag    10800 caggtctcag tagctgacct agagaaagga gcggccccta cagaggagac acgggtcact    10860
gtttgttaaa gtgaaggaga aataaatatt ctttcaaaga atcttaggtg agcccagttc    10920
atctgcgctg tggaggcctg gggaacagtt aaaaagaccc tgacacacac ccaaggcaaa    10980
caagcaacac acggctcctt ccgtaagggt ccatgattct ctgaagaatc agccccggaa    11040
tcagccccgg aatcaggtag tccgtaaaca caatgagtgt tttactctgc agaagtccag    11100
cctgctggcg tctcccatta ccaaaataga gggatagtca cgtgagctca ccggctcgat    11160
ttaaggcacg tggttttcca gggtagatga gctttggctt ctggaaccat tatggggcac    11220
gaaggatgga gccaggattt ttttttttt ttttttttc tattagcaat tgatttgctt    11280
gggcttggct ggacttgccc agttcttagg cccagtcttc ttaactgccg atctgaagtc    11340
tgtcatggag tcagcctagc cttctcactt cccttcagct cgaataggaa gaggaggtgc    11400
acaccagatg gtctgagagc agggataaat ggtgtgcctt tgtctttcag tatttcgtta    11460
ttttaagtag gaagatgctt ttctgtatta cattgcttgt gaaaccggaa gttgattcgg    11520
ggcacaggac aatggatttg gtgttttgca aggactgttt cagaagagag aggagtggaa    11580
gggtggttag agtgaggagt ggggtgggac gggatggggg aagagaagga agggccagac    11640
aggctaggta gggctgagag gaggcggtgg gaacttcttg agttagcgca gcagtaaact    11700
tggatgtgcg tgtatctttg tgatatatga cccggagccg tgtagctggc tccgatagta    11760
ctgctaatgt cagtgtcggg ggggggggt cccatactgt tccacagggg ctgcacattc    11820
ccatcgagag caggagggct cctctctcca tacatcctcg ccagcattcc ttgttgtttc    11880
tgtgatgaca ggggtggga tgaaatctct ctgttggttt gagagaccgt gaagaagctc    11940
aaccccagga cattttgcag tcttggaagg cagtgcctcc atgtggagcc gtggagccca    12000
tctctgagtc caggtcactc ttgcagttcg cactcagctc ttcagatgca ggagagacgt    12060
tggtgggaaa gcaagattgt ttgcttgttg agatagacac attctccaca caaaggctca    12120 cgtgggcaa aggctgattg acgtacagcg ttcaggaacg cctgtggtag agctatgatt    12180
agctgtctcc atctatgaag cagacaaaga gttataaaaa aaatcaatgt tttcaaattg    12240
tcaaactttt aacccgacag caagcgctct gtccctgggc taatccctag ccctggtttc    12300
ttgagatggg gtcttttgtg cactagactg gcctagaact cacgatctta gtgttccagc    12360
ctcccagctg ctgggatgag ccgctataac cagtctgcct gccttcctaa atttaagtg    12420 atgggaagtg ggggagaata cagtttaaag tatgcagatc tgagagcagg aacctggcaa    12480
```

| | | | | |
|---|---|---|---|---|
| agccaagggg | ccggagttac | aggcggctaa | catgggtgct | gggaactgac ccaggtcctt | 12540 |
| gagaggagca | gtgtgtactc | ttgaccaaac | aggtccgtct | ctccagtccc cgtagtatta | 12600 |
| aaaataggta | ctacgggcat | ggtggtgcac | acctttaatc | ccagcactag ggaggcagag | 12660 |
| gcaggtggat | ttctgagttt | gaggccagcc | tggtctacaa | aatgagttcc aggacagcca | 12720 |
| cggctataca | gagaaaccct | gtcttgaaaa | caaacaaca | acaaatagg tactacaaag | 12780 |
| cgatgtaatt | gtgctcaaac | atgcaaaccg | aggggactgt | atgcataaga aagagaaaga | 12840 |
| cggccacact | ggttctatct | gggtgacagg | aaatcagtat | ttttatttt cacattcatt | 12900 |
| ttttgttgt | tgttgttgac | acagtgattt | ttctatcaaa | aacattattt cttttatagt | 12960 |
| tcccctgagg | agctgttttt | aaagccgtgc | tttgaaaaac | cattgaagga gcagaggcag | 13020 |
| ggagactcct | gtgtggcagt | cggtgaagca | ggccctctgc | aggcaggctg ccctggact | 13080 |
| tgggagtctc | tttccctccc | tcctgtgctc | aaatagcaaa | tgtcaggctt caatgtagct | 13140 |
| agaaggttct | agaatgatta | agtttccaag | gctgaagagc | ttccctgttt gcctttcact | 13200 |
| tccctggaga | ggtcgttgtg | tgttccggag | tctgcaaggt | gcctttggtg atgcgggtgg | 13260 |
| ttcatctcgg | gagattccgc | ctggaggacc | caagttcaag | ccctgcctga gctacagagt | 13320 |
| gactttcagg | tcttctgcgc | aattcagtga | gacccagtct | acaaataaaa agtaaaaaga | 13380 |
| aggctgtgga | tggaactcgg | tggtagagtt | ctgggtttac | tccctagagg aggggagaag | 13440 |
| gaggaggagg | gaggaggaag | aggaagaaag | aagaagagaa | gggaagagga gaaggaaggg | 13500 |
| agggaagggg | ctgacaagaa | gagagaagag | ggagggaggg | gagggaaagg aaggggaaag | 13560 |
| gaagggaggg | aaggggctga | caagaagaga | gaagagggag | ggggaggg gaaaggaagg | 13620 |
| ggaaagaaga | gaagggtaag | aagaaactgt | tccaatggtc | tgggccacag agtgatggcc | 13680 |
| ttttgtggtg | atcagctgta | atccttgatt | tgacacaacc | tagaatctgg gaagcgagtt | 13740 |
| tctgtgaagg | agcattcaca | ctggctggcc | tgtgggcgtg | catgtgggag actgtcataa | 13800 |
| ttaggttcat | taatacagga | agtcccagcc | cactacaaat | ggcttcgttc catacccaag | 13860 |
| agatgctaac | tgtagacggt | tggagaaagc | aagcaagctg | tggataccc acgctctttc | 13920 |
| acctcggctc | ctgggggggtg | ggtgcactgt | gtctcttggt | attttaaagt cctgccttga | 13980 |
| cgtccctgct | gtgacagact | gtaactggaa | ttgtgagctt | tagtccttta gttttctacg | 14040 |
| ttggtttttc | tcaggatatt | ttatcgcagt | aacagaaaca | agaccaggac acttgatctc | 14100 |
| ctctgatcaa | cactgaagag | ttacaaaaca | ggctgaggaa | acaaacttc ttctccctct | 14160 |
| ccccttctg | tccctcccct | tcttctcgc | tccctccctt | gccccctctc tcctgtctc | 14220 |
| tgtctctgtc | tctgtctctg | tctctgtctc | tgtctctgcc | tctccctcc cctcccctcc | 14280 |
| ctctgtctct | gtctctgtct | ctgtctctgt | tctgtctct | gtctctgtcc ctttctcctc | 14340 |
| tatctcctaa | atggctggag | gccatgctag | ctcaatgttg | aactttgaac acgtatttag | 14400 |
| gaaatctttg | ttcttaacag | ttctgaagtg | ctgaagtggt | ggtttagtct ctcggcctga | 14460 |
| caagctcact | tcctctcact | ctgtcttaat | gaccaaatct | gccatttccc taaaacagca | 14520 |
| caggctccag | ctccaggttg | ctccggagcg | gag | | 14553 |

<210> SEQ ID NO 7
<211> LENGTH: 34
<212> TYPE: DNA
<213> ORGANISM: Artificial sequence
<220> FEATURE:
<223> OTHER INFORMATION: synthetic

<400> SEQUENCE: 7

```
ataacttcgt ataatgtatg ctatacgaag ttgt                                34
```

<210> SEQ ID NO 8
<211> LENGTH: 34
<212> TYPE: DNA
<213> ORGANISM: Artificial sequence
<220> FEATURE:
<223> OTHER INFORMATION: synthetic

<400> SEQUENCE: 8

```
ataacttcgt ataatgtata ctatacgaag ttag                                34
```

<210> SEQ ID NO 9
<211> LENGTH: 60
<212> TYPE: DNA
<213> ORGANISM: Artificial sequence
<220> FEATURE:
<223> OTHER INFORMATION: synthetic

<400> SEQUENCE: 9

```
agattctgtg ggctctgagg caacttgacc tcagccagat ggtatttgaa taacctgctc    60
```

<210> SEQ ID NO 10
<211> LENGTH: 54
<212> TYPE: DNA
<213> ORGANISM: Rattus norvegicus

<400> SEQUENCE: 10

```
agattctgtg ggttctgaga caacttgact tcagccagat ggcatttgaa taac          54
```

<210> SEQ ID NO 11
<211> LENGTH: 59
<212> TYPE: DNA
<213> ORGANISM: Mus musculus

<400> SEQUENCE: 11

```
agattctgtg ggttctgaga caacttgact ttagccagat ggtatttgag taatctggg     59
```

<210> SEQ ID NO 12
<211> LENGTH: 59
<212> TYPE: DNA
<213> ORGANISM: Homo sapiens

<400> SEQUENCE: 12

```
agattcagtg ggctttggga cagcttgact tcaactagat ggtatttgaa taatctgct     59
```

<210> SEQ ID NO 13
<211> LENGTH: 624
<212> TYPE: DNA
<213> ORGANISM: Artificial sequence
<220> FEATURE:
<223> OTHER INFORMATION: synthetic

<400> SEQUENCE: 13

```
ttcttgagtt ccgccaacgc ctagtgacat cctgtgcaca ccctaaggtg gcctttgtgt    60
ggcactggct tgggtggtcg ggaaaggcat tttcagcttg ttgcagaact gccacagtag   120
catgctgggt ccgtgaaagt ttctgcccgt taacaagaag tctctactac ttgtgacctc   180
accagtgaaa atttctttaa ttgtctcctg gtgttctggg ttttgcattt ttgtttctta   240
aggatacatt cctgggtgat gtcatgaagt ccccaaagac acagtggggc tgtgttggat   300
tgggaaagat gatttatctg gggtgtcaaa aggaaaagaa gggaaacagg cacttgggaa   360
aatgtcctcc cgcccacccg aatttttggct tggcaaccgt ggtggaggag caagaaacac   420
```

```
gtggacgttt gaggaggcat ggggtcctag gaggacagga agcagaagga gagagctggg    480
ctgacagcct gcaggcattg cacagtttca gaaggagatt acagcatgac tgagttttta    540
gggatccaac agggacctgg gtagagattc tgtgggctct gaggcaactt gacctcagcc    600
agatggtatt tgaataacct gctc                                           624

<210> SEQ ID NO 14
<211> LENGTH: 665
<212> TYPE: DNA
<213> ORGANISM: Rattus norvegicus

<400> SEQUENCE: 14
tttatctttc cctggggaca gccaaagcct ggtggcatcc tctgtgaagt gttcattcaa     60
gacaggctct gtcttaaagg tggccttcgc atggcgctgg cactggccgg ggcagtcagg    120
agagggtatt tttagcttct tgcagaatg gcctcaggag cgtgctgagt ctgtgaaagt     180
tgctgccagt taaggagaag tctctaccac tcgtgacctc accattgaaa atttctttaa    240
ttgtctcctc gtgttctggg ctttgcagtt ttgttcctaa ggatacattc ttgggtgatg    300
tcacgaagtc cccaaagaca cagtggggct gtgttagatc gggacagaca atattgctga    360
ggatttatct gaaggtgtca aaggagaag aagggaaaca gggcactcag ggaaatggcc     420
tctagtctga gttctggctc agcaacagag gtggggagat aaggcacaca cagtggttag    480
aaggagtcat cagggttctg gaggacagg aggcaggaga ggcagggctg acagtgtgca     540
atcattgtgt agtctcccaa ggagattaca acatggctga attttcaggg gtccaacgga    600
gactgtagtg gagattctgt gggttctgag acaacttgac ttcagccaga tggcatttga    660
ataac                                                                665

<210> SEQ ID NO 15
<211> LENGTH: 655
<212> TYPE: DNA
<213> ORGANISM: Mus musculus

<400> SEQUENCE: 15
tttatctttc cctggggacc gccaaagcct ggtggcatac tgtacattct gtacactgtt     60
cattcaaaac aggctctgtc ttaaagatgg tctgagcggt cagaaaaggg tattgttaac    120
ttgtttgcaa aactgcctca ggagagtgct gagtgcgtga agttgctgc ccgttaagga     180 gaagtctcta ctacttgtga tctcaccatc gaaaatttct ttaattgtct cctggtgttc    240
tgggttttgc agttttgttt ctaaggatac attcttgggt gatgtcacaa agtccccaaa    300
gacacggtgg agctgtgtta gatggggaaa gacagtctgc tgaggattta tctggaactg    360
tcagaaggaa aagaaggtaa atggggcact gggaaagtg gcctctagtt tgacttctgg     420
cttagcaaag gttgtgggga gataaggcat acacagtagt tagcaggagg caacaggtcc    480
tgggaggacg cgaggcagaa ggagaggctg ggctgacagc atgcaatcat tgcatagtct    540
ccaaaggaga ttgcaacatg gctgagtttt cagaggtcct acagagcccg tggtagagat    600
tctgtgggtt ctgagacaac ttgactttag ccagatggta tttgagtaat ctggg         655

<210> SEQ ID NO 16
<211> LENGTH: 706
<212> TYPE: DNA
<213> ORGANISM: Homo sapiens

<400> SEQUENCE: 16
agaaacacaa cttctcccag ggagagtcaa gagagcagtg tcatttccta taaaatgtcc     60
```

```
aaggccaatc ccaggtcccg gtgtcagccc ttgcgtgtgg cactggcacc agcagccaga     120
aaggttactt gtgacttgtt ttcagtgctt tcctgggagt gtcctgaaag ctggcagtgt     180
ttctgcctcg tcagaagagg cctcattcat ttggggttgt accagcaact taaaaagttt     240
ttttttttct tccctcttcc agtgttaata gattttgaaa gaggcatttt tgtttctaat     300
tacaaattcc tgggtgatgt cattaagccc tcaaacaccc ggtgagggcg gcactgaatg     360
gggaaagaca atatgctaac aagttatctg agggtgtcag aaagaaatga tgaaaaacag     420
tacagttggg ggaaatgttt tccagcctgc tttctggttt tagcgactgc atgggaagag     480
ataagacaca catggctttt ataaggagcc atcgggatct ctaggggaca tgaggcagga     540
gaaaagaatt gggctgaaag catccaatca tcacatattc acggagaaag agattacaat     600
atagcagagg aagctcttcc agggctccta cagggacctt tgggcaaaga ttcagtgggc     660
tttgggacag cttgacttca actagatggt atttgaataa tctgct                   706
```

<210> SEQ ID NO 17
<211> LENGTH: 268
<212> TYPE: DNA
<213> ORGANISM: Artificial sequence
<220> FEATURE:
<223> OTHER INFORMATION: synthetic

<400> SEQUENCE: 17

```
ttagagggaa aacagacata gcaaacagag ccacgtttag tgatgaaact ctcactttgc      60
ctgagtcatg tgcggccatg cccaggggtc aggctgacac tcaactcaaa aacaagtgag     120
aaattgaaga caatccgtgg tggcagctac tggaagggcc accacatccc cagaaagagt     180
ggagctgcta aaaagccatt tgtgataggc acagttatct tgaatgcatg gagcagagat     240
tacggaaaaa tcgagaatgt taatgagg                                        268
```

<210> SEQ ID NO 18
<211> LENGTH: 265
<212> TYPE: DNA
<213> ORGANISM: Rattus norvegicus

<400> SEQUENCE: 18

```
agctccagca agcacagcca catttaggga tgaaactctc actttgactg tgagtcacgt      60
gtagctgtgt cccgaggtca ggctggcccct cagctcaaaa acaagtgagg gattgaagca    120
attactcaga taattcacag ccacagctac ggggagggcc gcatcccccag aaacatcggg    180 gttactataa agctagtggt ggtcacagtt atcttgaatg tatggagcag aggagattac    240
agaaaaacct agaatgttaa tgagg                                          265
```

<210> SEQ ID NO 19
<211> LENGTH: 284
<212> TYPE: DNA
<213> ORGANISM: Mus musculus

<400> SEQUENCE: 19

```
agagagaaaa cagctacagc aaacagggcc acatttagtg acgaaactct cactttgact      60
gttgagtcat ttgcagtggg ccctgaggtc aggctggccc tcagctcaaa aacaagcgag     120
gaactgaagc aattactcag ataatccaca gccacagcca ctggaaaggg ccacatcccc     180
gagacagcac agcaggggtg gggtggggc tatgagaaag ttagtgattg tagcagttat     240
ctagaatgtg cggagcagag gaggttacac aaaaacctag aatg                      284
```

<210> SEQ ID NO 20

```
<211> LENGTH: 287
<212> TYPE: DNA
<213> ORGANISM: Homo sapiens

<400> SEQUENCE: 20
ggagagaaaa cagatatagc acacactgtc acatttagcg ttgaaactct cggtttgact        60
atgagtaatg ttcagccatg cccaagggtc aggcctacac tcactcagaa acaagtgggg       120
aattgaagca attattcaga taatccatag acatagctac tggccagtgc tgcacccctg       180
atttagccca gaaacagtaa tgctattata agctgttggt gatttgtgga gcaatcttga       240
atttattaag gaaaggagat tatagaaaaa tccagaatgc caatggg                    287
```